(12) United States Patent
Welti et al.

(10) Patent No.: US 12,371,424 B2
(45) Date of Patent: *Jul. 29, 2025

(54) PROCESSES FOR THE PREPARATION OF FURAZANOBENZIMIDAZOLES AND CRYSTALLINE FORMS THEREOF

(71) Applicant: Glioblastoma Foundation, Inc., Durham, NC (US)

(72) Inventors: Gregor Welti, Basel (CH); Markus Heubes, Basel (CH); David Tagliaferri, Basel (CH)

(73) Assignee: Glioblastoma Foundation, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/390,071

(22) Filed: Dec. 20, 2023

(65) Prior Publication Data

US 2024/0352007 A1    Oct. 24, 2024

Related U.S. Application Data

(63) Continuation of application No. 16/606,397, filed as application No. PCT/EP2018/060454 on Apr. 24, 2018, now Pat. No. 11,891,382.

(30) Foreign Application Priority Data

Apr. 26, 2017   (EP) ..................................... 17168283
May 24, 2017   (EP) ..................................... 17172753

(51) Int. Cl.
| | | |
|---|---|---|
| *C07D 413/04* | (2006.01) | |
| *C07C 269/06* | (2006.01) | |
| *C07C 271/06* | (2006.01) | |

(52) U.S. Cl.
CPC .......... *C07D 413/04* (2013.01); *C07C 269/06* (2013.01); *C07C 271/06* (2013.01); *C07B 2200/13* (2013.01)

(58) Field of Classification Search
CPC ........................... C07D 413/04; A61K 31/4245
See application file for complete search history.

(56) References Cited

U.S. PATENT DOCUMENTS

| | | | | |
|---|---|---|---|---|
| 8,802,858 B2 * | 8/2014 | Pohlmann | ............ | C07D 413/04 |
| | | | | 546/269.4 |
| 11,891,382 B2 * | 2/2024 | Welti | .................... | C07C 271/06 |
| 2012/0264792 A1 * | 10/2012 | Pohlmann | ............ | A61P 35/00 |
| | | | | 514/364 |

FOREIGN PATENT DOCUMENTS

WO    WO-2015173341 A1 *  11/2015   ......... A61K 31/4245

OTHER PUBLICATIONS

Berges et al. Mol. Cancer Ther. 2016, 15, 2740-2749 (Year: 2016).*

(Continued)

*Primary Examiner* — Matthew P Coughlin

(57) ABSTRACT

The present invention provides processes for preparing a compound of formula I and pharmaceutically acceptable salts thereof, comprising deprotecting a compound of formula II wherein each $R^3$ independently represents a tertiary alkyl group, preferably wherein each $R^3$ is tertiary butyl. The (Continued)

invention also provides intermediates useful for preparing compounds of formula I and processes for preparing these intermediates. Additionally the invention provides polymorphic forms of the dichloride salt of the compound of formula I and their use in the treatment of proliferative disorders.

20 Claims, 38 Drawing Sheets

(56) References Cited

OTHER PUBLICATIONS

The English translation of the Japanese Office Action, mailed on Dec. 12, 2023, in related Japanese Appl. No. 2022-187098.

* cited by examiner

PROCESSES FOR THE PREPARATION OF FURAZANOBENZIMIDAZOLES AND CRYSTALLINE FORMS THEREOF

This application is a Continuation of application Ser. No. 16/606,397, filed Oct. 18, 2019, which is a National Stage Application of PCT/EP2018/060454, filed Apr. 24, 2018, which claims priority from European Patent Application No. 17168283.4, filed on Apr. 26, 2017 and European Patent Application No. 17172753.0, filed on May 24, 2017. The priority of said PCT and European Patent Applications are claimed. Each of the prior mentioned applications is hereby incorporated by reference herein in its entirety.

The present invention relates to processes useful for the preparation of certain compounds that have use in the treatment of proliferative disorders, as well to intermediates useful in the processes. The invention also relates to a crystalline salt of the compound of formula I as described herein, methods for the preparation thereof, pharmaceutical compositions thereof, and its use in the treatment of proliferative disorders and diseases.

WO 2011/012577, WO 2012/098207, WO 2012/098203, WO 2012/113802, WO 2012/130887, WO 2015/173341 and WO 2017/068182 describe a compound with the following structure (designated here as formula I) and its use in the treatment of proliferative disorders such as cancer, as well as processes for its preparation.

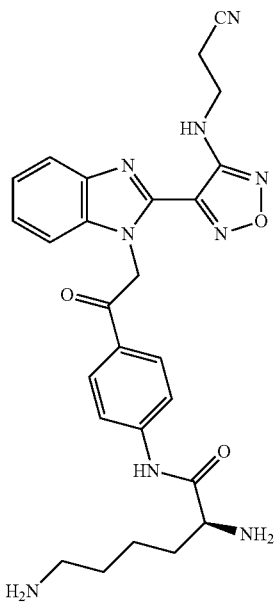

(I)

The compound is a prodrug of the active moiety shown below as the compound of formula B.

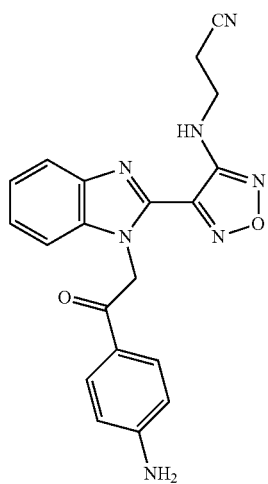

(B)

WO 2011/012577 describes processes for the production of the compound of formula I in which benzyloxy carbamate groups are used to protect the amino groups on the lysine moiety. It has now been found that use of other carbamate protecting groups, in particular tert-butyl carbamate (BOC) instead of benzyloxy carbamate protecting groups leads to surprising advantages for commercial production.

In addition, when synthesized according to the general procedures described in WO 2011/012577 the compound of formula I as a dichloride salt is isolated as an amorphous solid. It has now been found that the dichloride salt of the compound of formula I can be isolated in crystalline form, thereby providing advantages for pharmaceutical processing.

In a first aspect the invention provides processes for preparing a compound of formula I or a pharmaceutically acceptable salt thereof

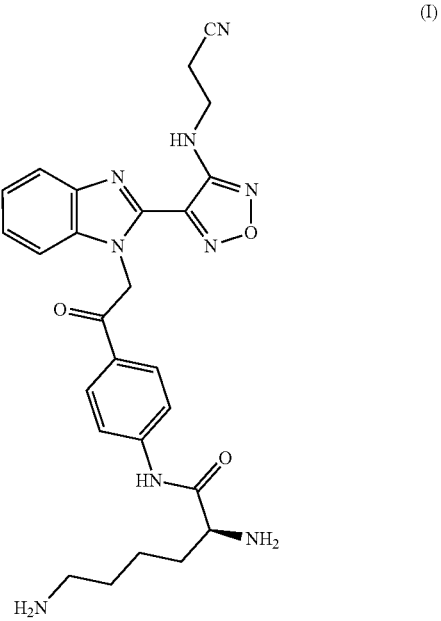 [SMILES: N#CCCNc1nonc1-c1nc2ccccc2n1CC(=O)c1ccc(NC(=O)[C@@H](N)CCCCN)cc1]

(I)

comprising deprotecting a compound of formula II

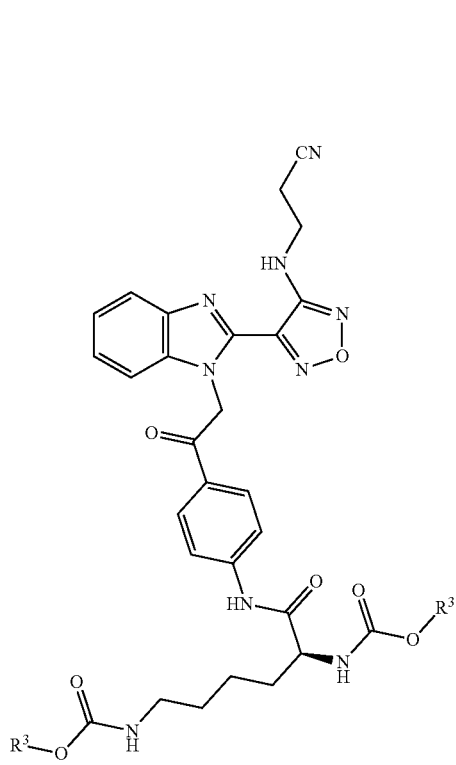

(II)

wherein each R³ independently represents a tertiary alkyl group.

Compounds of formula II may be prepared by reacting a compound of formula III

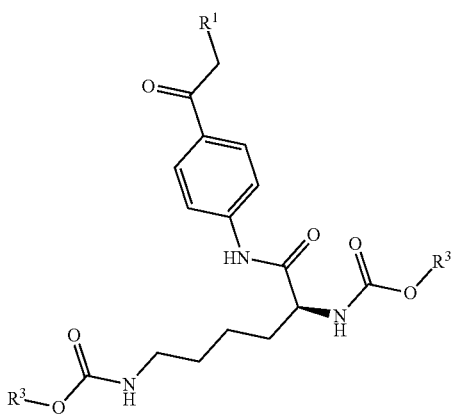

(III)

wherein R¹ represents a leaving group; and
wherein each R³ independently represents a tertiary alkyl group;

with a compound of formula IV

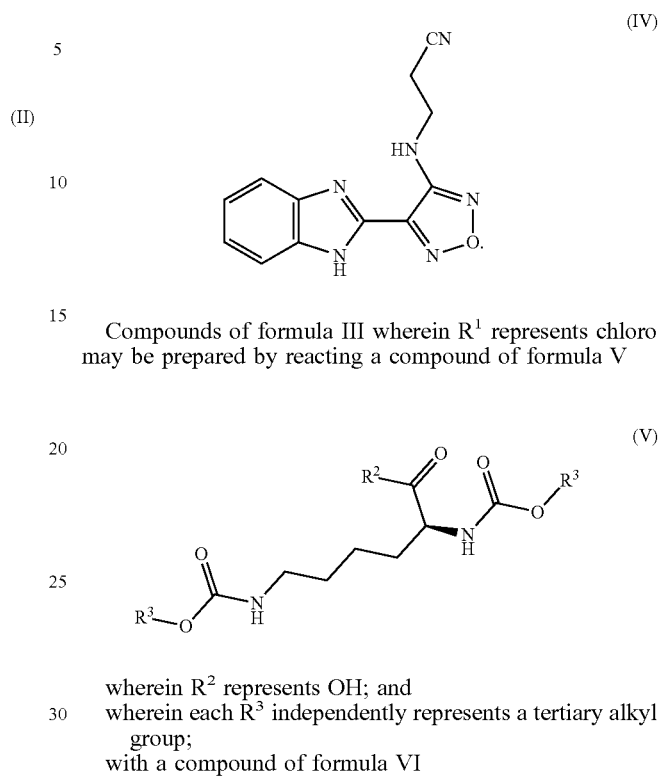

Compounds of formula III wherein R¹ represents chloro may be prepared by reacting a compound of formula V wherein R² represents OH; and
wherein each R³ independently represents a tertiary alkyl group;
with a compound of formula VI wherein R¹ᵃ represents chloro.

In a further aspect the invention provides a process for preparing a compound of formula II comprising reacting a compound of formula III with a compound of formula IV.

In a further aspect the invention provides a process for preparing a compound of formula III wherein R¹ represents chloro comprising reacting a compound of formula V with a compound of formula VI.

In a further aspect the invention provides a compound of formula II.

In a further aspect the invention provides a compound of formula III.

R¹ represents a leaving group which is selectively substitutable by the benzimidazole nitrogen atom of the compound of formula IV. Such leaving groups include chloro, bromo, iodo, activated OH groups such as sulfonic esters (e.g. mesylate, triflate, tosylate, esylate, besylate), carbonyls e.g. trifluoroacetate, other reactive esters such as nitrate esters and perchloric esters, nitrophenyl ether, alkylphosphites and alkylphosphates. Preferably R¹ is chloro, bromo or a sulfonate ester, more preferably bromo or chloro, most preferably chloro.

Each $R^3$ independently represents a tertiary alkyl group, e.g. —$C(R^4)_3$, wherein each $R^4$ represents independently $C_1$-$C_8$alkyl. Preferably each $R^4$ independently represents methyl, ethyl or propyl, more preferably methyl. Most preferably each $R^3$ represents tertiary butyl.

In one embodiment each $R^3$ represents tertiary butyl and $R^1$ represents chloro, bromo or a sulfonic ester.

In a further embodiment each $R^3$ represents tertiary butyl and $R^1$ represents chloro.

Step 1: Acylation of Amino Compound VI with Alkyl Carbamate Protected Compound V

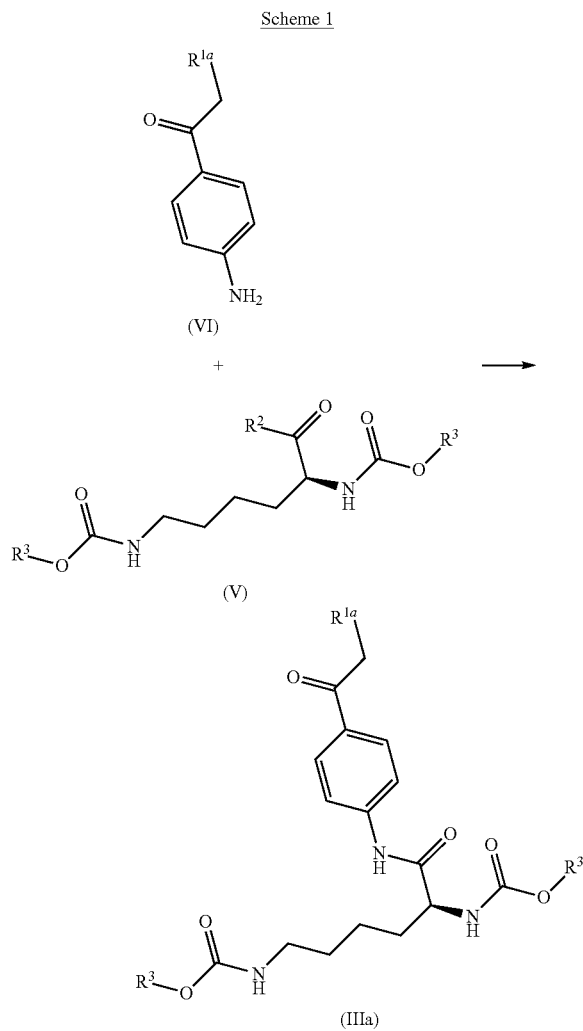

Suitable reaction conditions for acylation of primary amines to form amides are well known to the person skilled in the art. The reaction usually involves "activating" a carboxylic acid with suitable activating reagents, see e.g. Montalbetti et al., Tetrahedron 61 (2005), 10827-10852. Generally formation of an amide from a carboxylic acid may proceed via an acyl halide, an acyl azide, an acyl imidazole, an anhydride or an active ester such as an aromatic or phospho ester. The reaction may proceed via two steps comprising activation of the carboxylic acid followed by coupling to the amide, or, depending on the reagents, via a one-pot process.

Suitable acyl halides include acyl chlorides, acyl fluorides and acyl bromides, with acyl chlorides being generally preferred. Suitable reagents for the formation of an acyl chloride include thionyl chloride, oxalyl chloride, phosphorus trichloride, phosphorus oxychloride, phosphorus pentachloride, cyanuric chloride, pivaloyl chloride and isopropyl chloroformate. Suitable reagents for the formation of an acyl fluoride include cyanuric fluoride in the presence of pyridine and N,N-tetramethylfluoro-formamidinium hexafluorophosphate (TFFH) in the presence of Hünig's base, and suitable reagents for the formation of acyl bromides include 1-bromo-N,N-trimethyl-1-propenylamine.

Suitable reagents for the formation of anhydrides include dicyclohexyl carbodiimide (DCC), diisopropyl carbodiimide (DIC) and 1-ethyl-3-(3'-dimethylamino) carbodiimide (EDC).

Suitable reagents for the formation of active esters include phosphonium reagents such as benzotriazol-1-yl-oxy-tris-(dimethylamino)-phosphonium hexafluorophosphate (BOP) or benzotriazol-1-yl-oxy-tris-pyrrolidino-phosphonium hexafluorophosphate (PyBop®), uronium salts such as O-(1H-benzotriazol-1-yl)-N,N,N'N'-tetramethyluronium hexafluorophosphate (HBTU), its tetrafluoroborate equivalent (TBTU) or the pyridinium analogue (HATU), and 2,4,6-tripropyl-1,3,5,2,4,6-trioxatriphosphorinane-2,4,6-trioxide (T3P®).

Hydrazine is generally used for the formation of acylazides and carbonyl diimidazole (CDI) is generally used for the formation of acylimidazoles.

Preferred activating agents are DIC, DCC and T3P®.

The reaction may include an auxiliary such as 4-(N,N-dimethylamino)pyridine (DMAP) or a hydroxybenzotriazole. For example when anhydrides or T3PR are used as activating agents DMAP may also be included in the reaction and may improve conversion, particularly when mixed anhydrides are used. Generally the skilled person is able to determine whether or not an auxiliary is useful, and select suitable alternatives.

The reaction may be performed in a suitable solvent, usually an organic solvent including ketones, such as acetone, methylethyl ketone (2-butanone) or cyclohexanone, tetrahydrofuran (THF) or 2-methyltetrahydrofuran, formamides such as dimethylformamide (DMF), haloalkanes such as dichloromethane (DCM), esters such as ethylacetate, ethers such as diisopropylether (DIPE), aromatic solvents such as p-xylene and toluene, or mixtures thereof. In the context of the invention it is preferred that the solvent is ethyl acetate/DIPE, DMF, toluene or DCM. Generally the person skilled in the art is able to select a suitable solvent.

In one preferred embodiment the activating agent is DCC, preferably wherein the solvent is DCM, optionally with DMAP as an auxiliary. In another preferred embodiment the activating agent is T3P®, preferably wherein the solvent is toluene, optionally with DMAP as an auxiliary.

The reaction may be performed in the presence or in the absence of a suitable base, such as 2,4,6-trimethylpyridine (TMP), or a tertiary amine such as diisopropylethylamine (DIPEA) or triethylamine (TEA). When the activating agent is an anhydride such as DCC a base may be optional, on the other hand, when the activating agent is a phosphonium reagent such as T3PR the presence of a base can be beneficial, and in this case the base is preferably TEA.

When the activating agent is an anhydride such as DCC the reaction generally proceeds via two steps (activation and coupling). Usually the reaction product from the first step is treated e.g. by filtration in order to remove the resulting urea. In the first step the reaction is usually performed at ambient temperature, but may be for example −20° C. up to the boiling point of the solvent. Preferably the temperature is −10° C. to 50° C., more preferably 15° C. to 25° C. In other words the temperature is usually at least −20° C., preferably at least −10° C., more preferably at least 15° C. The temperature will not be higher than the boiling point of the solvent and is preferably up to 50° C., more preferably up to 25° C. The time needed to achieve the desired level of conversion will vary depending on the temperature used, e.g. from 15 minutes up to several hours. In the second step the range of possibilities of temperature and reaction time are the same as for the first step. Generally the pressure is ambient pressure.

When the activating agent is a phosponium reagent such as T3P® the reaction can be performed via a one-pot reaction. This can lead to reduced processing costs and is therefore advantageous from the perspective of commercial production. Generally the reaction is performed at a temperature of e.g. −20° C. to 20° C., e.g. at least −20° C., e.g. up to 20° C. When not using an auxiliary the reaction is preferably performed at the lower end of this range, e.g. −20° C. to 0° C., preferably −15° C. to −5° C., more preferably about −10° C., which can improve reaction selectivity. In other words the temperature is usually at least −20° C., preferably at least −15° C. Likewise the temperature is usually up to 0° C., preferably up to −5° C. When using an auxiliary such as DMAP the reaction is preferably performed in the higher end of the range, e.g. 0° C. to 20° C., preferably 5° C. to 15° C., more preferably about 10° C. In other words the temperature is usually at least 0° C., preferably at least 5° C. Likewise the temperature is usually up to 20° C., more preferably up to 15° C. The time needed to achieve the desired level of conversion will vary depending on the temperature used and may vary e.g. from one hour to 24h. When an auxiliary is used the reaction time will usually be shorter and when an auxiliary is not used the reaction time will usually be longer. Generally the pressure is ambient pressure.

Compounds of formula V and VI are commercially available. The compound of formula V has the CAS registry number 2483-69-8 ($R^2$ is OH, $R^3$ is tert-butyl). The compound of formula VI has the CAS registry number 2631-71-2 ($R^{1a}$ is chloro) and 23442-14-0 ($R^{1a}$ is bromo).

Step 2: Nucleophilic Substitution of Leaving Group $R^1$ on Compound III by the Benzimidazole Moiety of Compound IV

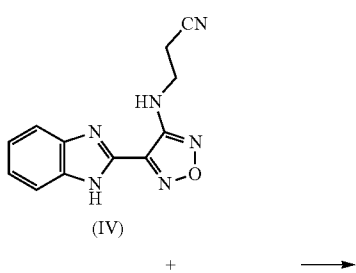

Scheme 2

(IV)

+

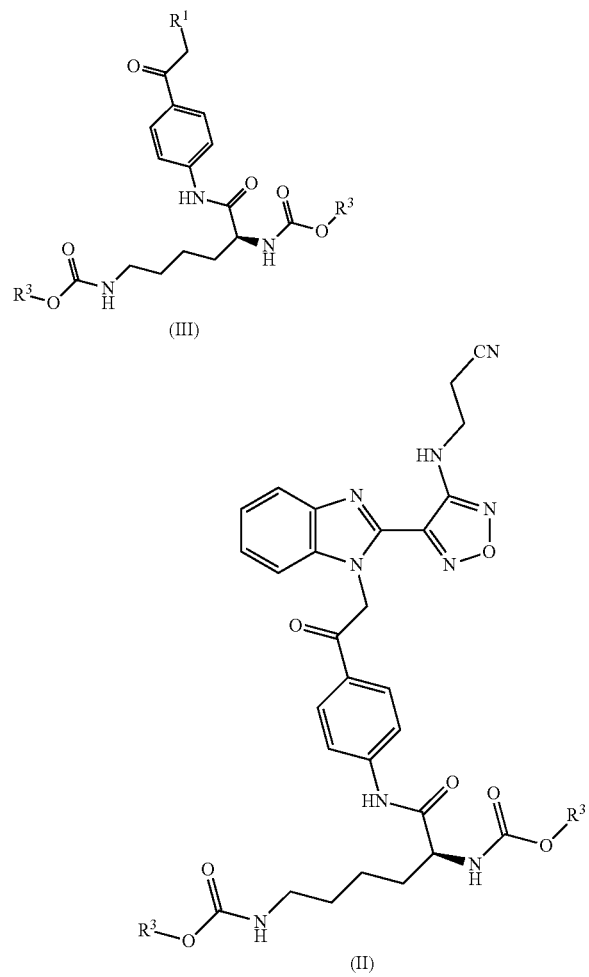

(III)

(II)

Note that it is difficult to prepare compounds of formula III wherein $R^1$ is other than chloro via coupling of compound VI with compound V according to Scheme 1 due to intramolecular coupling. However, compounds of formula III wherein $R^1$ is bromo can be prepared via bromination following the methodology described in WO 2011/012577, e.g. in Example 1. Likewise, the skilled person can prepare compounds of formula III wherein $R^1$ is a leaving group such as iodo, activated OH groups, carbonyl reactive esters, nitrophenyl ether, alkylphosphites and alkylphosphates using standard techniques.

Suitable reaction conditions for the nucleophilic substitution of leaving group $R^1$ by the compound of formula IV are well known to the person skilled in the art.

The reaction is usually performed in the presence of a suitable base, although neutral conditions may be also used and in some cases acidic conditions. Basic conditions are preferred, wherein the base is usually an inorganic base such as a carbonate, preferably potassium carbonate. Note that use of a nucleophilic base may lead to undesired hydrolysis of the nitrile group unless conditions are carefully controlled and therefore non-nucleophilic bases are preferred. Generally the skilled person is able to determine whether or not a base is useful, to select a suitable base and to find suitably mild basic conditions to minimize and preferably avoid hydrolyzing the nitrile group.

The reaction may be performed in a suitable solvent, usually an organic solvent, preferably an aprotic solvent such as acetone, DMSO or DMF, preferably DMF.

The reaction parameters can be optimized by the person skilled in the art, but generally the temperature is e.g. 25° C. to 45° C., preferably 35° C. to 42° C., e.g. generally at least 25° C., preferably at least 35° C., e.g. generally up to 45° C., preferably up to 42° C. The time needed to achieve the desired level of conversion will vary depending on the temperature used, which may be e.g. 1 hour to 24 hours. Conversion will usually be faster when higher temperature is used. Generally the pressure is ambient pressure.

The compound of formula IV can be obtained using method described in WO 2011/012577 and WO2004/103994.

Step 3: Cleavage of the carbamate protecting group of compound II to obtain compound I

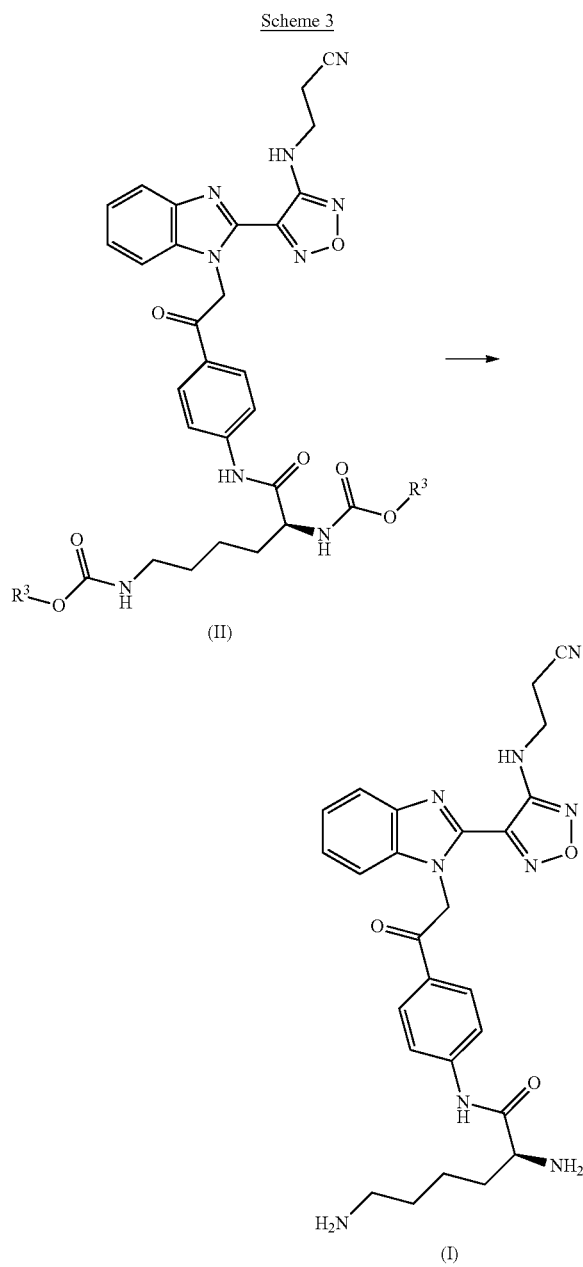

Deprotection of the compound of formula II involves removing the —C(=O)OR$_3$ protecting groups to leave primary amine groups, without modifying any other part of the molecule. Suitable conditions and reagents for removing carbamate protecting groups from primary amino groups, including tert-butylcarbamate, are described in detail in the protecting group manual Greene's Protective Groups in Organic Synthesis, 5th Ed. by Peter G. M. Wuts (John Wiley & Sons, Inc., Hoboken, New Jersey, USA, 2014). In view of the extensive knowledge in the art the skilled person is able to select suitable conditions, solvents and reagents to perform this deprotection step.

Usually the reaction includes a nucleophilic reagent that is able to cleave the carbonyl-nitrogen bond. Deprotection is commonly performed under acidic conditions, but suitable non-acidic conditions are also described in the above-mentioned manual. Suitable acids include hydrochloric acid, trifluoroacetic acid, trimethylsilyl iodide, zinc bromide, preferably hydrochloric acid. Deprotection may occur via hydrolysis of the carbamate, although deprotection under anhydrous conditions is also described in the above-mentioned manual.

The reaction may be performed in a suitable solvent, usually an organic solvent such as an aprotic solvent, preferably acetone or tetrahydrofuran.

The temperature may be between −20° C. and the boiling point of the solvent, e.g. 0° C. to 50° C. Usually the temperature is e.g. 20° C. to 30° C., e.g. at least 20° C., e.g. up to 30° C. The time needed to achieve the desired level of conversion will vary depending on the temperature used and may be e.g. up to 25 hours. Generally the pressure is ambient pressure.

Compounds of formula I may be converted into pharmaceutically acceptable salts of the compound of formula I following the methodology described in WO 2011/012577. Such salts are formed, for example, as acid addition salts, preferably with organic or inorganic acids. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid. A preferred pharmaceutically acceptable salt is a chloride salt, in particular the dichloride salt of the compound of formula I.

The processes of the invention may also include using salts of compounds of formula II, III, IV, V and VI where applicable and reference to compounds of formula II, III, IV, V and VI includes salts thereof.

In WO 2011/012577 a process for the production of compounds of formula I is described in which benzyl ester groups are used to protecting the amine groups on the lysine moiety. The process disclosed provides the compound of formula I with a purity of ca. 90% (area), enantiomeric excess of ca. 81% ee and yield of ca. 50% as shown in Comparative Example 1. Surprisingly, it has now been found that compounds of formula I can be obtained in high purity and in significantly higher yield by the use of tert-butyl oxycarbonyl esters to protect the amino group.

TABLE 1

Data comparison

|  | Yield | Purity | Optical purity |
|---|---|---|---|
| Comparative Example 1 | 50% | 90-91% | 81% ee |
| Example 3 | 83% | 99.6% | >99.6% ee |

It has also been found that the compound of formula II can be deprotected and crystallized as the dichloride salt into an advantageous crystalline form (termed here "Form E") in a one-pot reaction. This can be achieved by performing the deprotection step using HCl and methanol as the solvent, followed by stirring at a temperature of 0 to 10° C., preferably 3 to 8° C., more preferably about 5° C. In other words the temperature is generally at least 0° C., preferably at least 3° C. Likewise the temperature is generally up to 10° C., preferably up to 8° C.

In a further aspect the invention provides a crystalline dichloride salt of the compound of formula I. Crystalline forms of the compound of formula I can be characterized by various techniques including X-Ray Powder Diffractometry (XRPD) using CuKα radiation.

Form E

One polymorphic form that has advantageous physical properties for formulating the dichloride salt into a solid formulation for administration to patients is the polymorphic form termed here "Form E". Form E has been found to show high polymorphic stability at normal temperatures (see Example 5a), it shows 1% water absorption for the compound up to 85% RH (see Example 5f) and good solubility (see Example 5g). Many other polymorphic forms (including Form F and Form G described in the Examples) do not show polymorphic stability and are generally not easily usable for pharmaceutical processing.

Accordingly, in one embodiment the crystalline salt (Form E) of the compound of formula I has an XRPD pattern comprising a peak at 6.0 degrees 2θ (±0.2 degrees 2θ) when measured using CuKα radiation. Preferably the crystalline dichloride salt of the compound of formula I (Form E) has an XRPD pattern comprising peaks at 6.0, 9.4 and 9.9 degrees 2θ (±0.2 degrees 2θ). More preferably the crystalline salt of the compound of formula I (Form E) has an XRPD pattern comprising peaks at 6.0, 9.4, 9.9, 10.7, 17.4, 21.4, 25.8 and 28.4 degrees 2θ (±0.2 degrees 2θ). Even more preferably the crystalline salt of the compound of formula I (Form E) has an XRPD pattern comprising peaks at 6.0, 9.4, 9.9, 10.7, 11.6, 11.9, 17.4, 21.4, 22.4, 23.0, 24.2, 24.6, 25.8 and 28.4 degrees 2θ (±0.2 degrees 2θ).

Preferably the orthorhombic primitive cell parameters are defined to be a=4.813±0.001 Å, b=20.02±0.01 Å, c=59.40±0.02 Å, V=5724±5 Å$^3$.

The crystalline dichloride salt of the compound of formula I (Form E) may also be confirmed using IR and/or solid state NMR data in combination with one or more XRPD peaks. In this case the crystalline dichloride salt (Form E) preferably has an IR spectrum comprising peaks at 1701, 1665, 1335, 1241, 1170, 942, 924, 864, 699 and 628 cm$^{-1}$ (±2 cm$^{-1}$), which have been identified as peaks that differentiate Form E from other polymorphic forms. Likewise, the crystalline dichloride salt preferably has a 13C CP MAS (14 kHz) NMR spectrum referenced to external tetramethylsilane (TMS) standard measurement and/or a 13C NMR spectrum in [D6]-DMSO referenced to ([D6] DMSO, internal standard) as shown in the Table below (Table 5).

In a further embodiment the crystalline dichloride salt of the compound of formula I (Form E) is characterized by XRPD pattern comprising a peak at 6.0 degrees 2θ (±0.2 degrees 2θ) and the above IR spectrum peaks. In a further embodiment Form E is characterized by an XRPD pattern comprising a peak at 6.0 degrees 2θ (±0.2 degrees 2θ) and the above IR spectrum peaks and/or at least one of the two sets of NMR spectrum peaks in the table below (Table 5). In a further embodiment Form E is characterized by an XRPD pattern comprising peaks at 6.0, 9.4 and 9.9 degrees 2θ (±0.2 degrees 2θ) and the above IR spectrum peaks and/or at least one of the two sets of NMR spectrum peaks in the table below (Table 5). In a further embodiment Form E is characterized by an XRPD pattern comprising a peaks at 6.0, 9.4, 9.9, 10.7, 17.4, 21.4, 25.8 and 28.4 degrees 2θ (±0.2 degrees 2θ) and the above IR spectrum peaks and/or at least one of the two sets of NMR spectrum peaks in the table below (Table 5). In a further embodiment Form E is characterized by an XRPD pattern comprising peaks at 6.0, 9.4, 9.9, 10.7, 11.6, 11.9, 17.4, 21.4, 22.4, 23.0, 24.2, 24.6, 25.8 and 28.4 degrees 2θ (±0.2 degrees 2θ) and the above IR spectrum peaks and/or at least one of the two sets of NMR spectrum peaks in the table below (Table 5).

Likewise, any of the embodiments described above relating to different ways of characterizing Form E may be combined with each other in any combination.

Form E can be prepared by cooling crystallization, e.g. with stirring, from mixtures of 2-butanone/methanol, 1,4-dioxane/methanol or ethyl acetate/methanol. It can also be obtained by slurrying the compound of formula I in alcohols, such as methanol, ethanol or 2-propanol, ethyl acetate or acetonitrile, or mixtures of these solvents. It can also be obtained from solvent mixtures composed of one of the aforementioned solvents and another solvent such as ethers (e.g. tert-butyl methyl ether, 1,4-dioxane), ketones (e.g. 2-butanone), or halocarbons (e.g. 1,2-dichloroethane). It can also be obtained from the compound of formula I (free base) by treatment with hydrogen chloride in a suitable solvent. The conversion time depends on the temperature and generally the higher the temperature the faster the crystallization. For example at room temperature it may take several days, sometimes up to two weeks, whereas at reflux crystallization may be achieved within several hours.

In a further aspect the invention provides a process for preparing a crystalline salt of the compound of formula I (Form E), comprising the step of crystallizing the dichloride salt of the compound of formula I from a solvent, wherein said solvent is acetonitrile, methanol, ethanol, ethylacetate, isopropanol or mixture thereof, or a solvent mixture comprising acetonitrile, methanol, ethanol, ethylacetate and/or isopropanol. Preferably the solvent is acetonitrile, methanol, or ethanol or a mixture thereof, or a solvent mixture comprising acetonitrile, methanol and/or ethanol. Preferred solvent mixtures are mixtures of two or three of acetonitrile, methanol and ethanol, as well as methanol and methyl tert-butyl ether, methanol and toluene, methanol and acetonitrile, methanol and 2-butanone, methanol and dioxane, and methanol and ethyl acetate. More preferred solvent mixtures are mixtures of two or three of acetonitrile, methanol and ethanol, as well as methanol and methyl tert-butyl ether, methanol and toluene, and methanol and acetonitrile. In one embodiment the solvent is acetonitrile or a solvent mixture comprising acetonitrile. In another embodiment the solvent is methanol or a solvent mixture comprising methanol. In another embodiment the solvent is ethanol or a solvent mixture comprising ethanol. In another embodiment the solvent is acetonitrile, methanol or ethanol or mixture thereof.

The process may comprise the step of combining the solvent and the compound of formula I as the dichloride salt and allowing the dichloride salt of the compound of formula I to crystallize e.g. by allowing the mixture to stand. Alternatively the process may comprise the step of combining the solvent and the compound of formula I as the free base together with hydrochloric acid and allowing the dichloride salt of the compound of formula I to crystallize e.g. by allowing the mixture to stand.

In a further aspect the invention provides a pharmaceutical composition comprising a pharmaceutically effective amount of the crystalline dichloride salt (Form E) of the compound of formula I in combination with a pharmaceutically acceptable carrier, diluent or excipient.

In a further aspect the invention provides a crystalline dichloride salt of the compound of formula I (Form E) for use in the treatment of a proliferative disorder or disease.

In a further aspect the invention provides use of a crystalline dichloride salt of the compound of formula I (Form E) in the manufacture of a medicament for use in the treatment of a proliferative disorder or disease.

In a further aspect the invention provides a method of treating a proliferative disorder or disease comprising administering a crystalline dichloride salt of the compound of formula I (Form E) to a patient in need thereof.

System A+M

A further crystalline form of that may be used to formulate the dichloride salt into a solid formulation for administration to patients is the crystalline form termed here "System A+M".

This crystalline form of the dichloride salt of the compound of formula I (System A+M) is unusual in that it has the ability to take up water and change its polymorphic form in a reversible and predictable manner. In this sense the crystalline form is a polymorphic system, which exhibits specific polymorphic forms depending upon the degree of humidity that the polymorphic system is exposed to. In particular, the polymorphic system exhibits specific polymorphic forms at zero and 100 percent relative humidity (RH) (all references to relative humidity refer to relative humidity at 1atm/25° C. unless otherwise stated), with a continuum of reproducible polymorphic forms between the two extremes. Although System A+X exhibits different polymorphic forms (hydrates), the system itself has been found to be polymorphically stable in that the polymorphic changes are reversible and predictable. In addition it shows good solubility (see Example 8d). Many other polymorphic forms (including Form F and Form G described in the Examples) do not show polymorphic stability and are generally not easily usable for pharmaceutical processing.

The polymorphic system can be recognized by subjecting the crystalline form to zero humidity until the crystalline form contains essentially no moisture. The crystalline form will then exhibit the polymorph termed here Form A0. Alternatively the polymorphic system can be recognized by subjecting the crystalline form to high humidity (>95% RH) until the polymorphic form does not take up any further moisture. The crystalline form will then exhibit the polymorph termed here Mixture A2+M11, which is a mixture of the two polymorphic forms A2 and M11. Other polymorphic forms and mixture of forms exists between these two extreme forms, depending upon the amount of moisture present within the crystalline form.

Accordingly, in one embodiment the invention provides a crystalline dichloride salt of the compound of formula I (Form A0), having an XRPD pattern comprising a peak at 3.9 degrees 2θ (±0.2 degrees 2θ) when measured using CuKα radiation, when the crystalline salt contains essentially no moisture. Preferably, the crystalline dichloride salt of the compound of formula I (Form A0) has an XRPD pattern comprising peaks at 3.9, 7.9 and 9.7 degrees 2θ (±0.2 degrees 2θ). More preferably the crystalline dichloride salt of the compound of formula I (Form A0) has an XRPD pattern comprising peaks at 3.9, 7.9, 9.7, 11.2 and 23.9 degrees 2θ (±0.2 degrees 2θ). Even more preferably the crystalline dichloride salt of the compound of formula I (Form A0) has an XRPD pattern comprising peaks at 3.9, 7.9, 9.7, 11.2, 23.9, 25.0 and 25.5 degrees 2θ (±0.2 degrees 2θ).

"Essentially no moisture" means for example zero or negligible moisture, e.g. 0.1% moisture (w/w) or less, preferably zero moisture. This may be achieved by heating the crystalline form for e.g. at least 2.5 h at around 195° C., or longer, e.g. at least 4 h.

In a further embodiment the invention provides a crystalline dichloride salt of the compound of formula I (Mixture A2+M11), having an XRPD pattern comprising a peak at 2.7 degrees 2θ (±0.2 degrees 2θ) when measured using CuKα radiation, when the crystalline salt has been exposed to 100 percent humidity for a period of time such that it does not take up any additional moisture. Preferably, the crystalline dichloride salt of the compound of formula I (Mixture A2+M11) has an XRPD pattern comprising peaks at 2.7, 8.3 and 9.4 degrees 2θ (±0.2 degrees 2θ). More preferably the crystalline dichloride salt of the compound of formula I (Mixture A2+M11) has an XRPD pattern comprising peaks at 2.7, 8.3, 9.4, 14.8 and 19.7 degrees 2θ (±0.2 degrees 2θ). Even more preferably the crystalline dichloride salt of the compound of formula I (Mixture A2+M11) has an XRPD pattern comprising peaks at 2.7, 8.3, 9.4, 14.8, 19.7 and 24.1 degrees 2θ (±0.2 degrees 2θ).

Subjecting the crystalline form to high humidity (>95% RH) until the polymorphic form does not take up any further moisture may require subjecting the crystalline form to ≥95% RH for at least a week at 25° C. or even longer, e.g. 2 weeks or more.

Three common polymorphic forms within the system at intermediate levels of humidity are the forms termed here Mixture A1+M1 (which usually exists from ca. 1 to ca. 20% RH), Mixture A1+M4 (usually from ca. 10 to ca. 50% RH) and Form M3+M5 (usually from ca. 50 to ca. 90% RH).

Thus in a further embodiment the invention provides a crystalline dichloride salt of the compound of formula I (Mixture A1+M1), having an XRPD pattern comprising a peak at 3.6 degrees 2θ (±0.2 degrees 2θ) when measured using CuKα radiation. Preferably, the crystalline dichloride salt of the compound of formula I (Mixture A1+M1) has an XRPD pattern comprising peaks at 3.6, 4.0, and 8.1 degrees 2θ (±0.2 degrees 2θ). More preferably the crystalline dichloride salt of the compound of formula I (Mixture A1+M1) has an XRPD pattern comprising peaks at 3.6, 4.0, 8.1, 9.4, 11.0, 21.1 and 24.5 degrees 2θ (±0.2 degrees 2θ).

Likewise, in a further embodiment the invention provides a crystalline dichloride salt of the compound of formula I (Mixture A1+M4), having an XRPD pattern comprising a peak at 3.4 degrees 2θ (±0.2 degrees 2θ) when measured using CuKα radiation. Preferably, the crystalline dichloride salt of the compound of formula I (Mixture A1+M4) has an XRPD pattern comprising peaks at 3.4, 4.0 and 8.1 degrees 2θ (±0.2 degrees 2θ). More preferably the crystalline dichloride salt of the compound of formula I (Mixture A1+M4) has an XRPD pattern comprising peaks at 3.4, 4.0, 8.1, 11.1, 16.5 and 24.0 degrees 2θ (±0.2 degrees 2θ).

Likewise, in a further embodiment the invention provides a crystalline dichloride salt of the compound of formula I (Form M3+M5), having an XRPD pattern comprising a peak at 3.0 degrees 2θ (±0.2 degrees 2θ) when measured using CuKα radiation. Preferably, the crystalline dichloride salt of the compound of formula I (Form M3+M5) has an XRPD pattern comprising peaks at 3.0, 3.6 and 9.4 degrees 2θ (±0.2 degrees 2θ). More preferably the crystalline dichloride salt of the compound of formula I (Form M3+M5) has an XRPD pattern comprising peaks at 3.0, 3.6, 9.4, 11.1, 12.7, 15.3, 23.6 and 24.5 degrees 2θ (±0.2 degrees 2θ).

Other polymorphic forms within the system at intermediate levels of humidity are described and characterized in the Examples, together with characterizations of isolated components of the system. Note that Forms F and G are not part of System A+M, but can occur during isolation of individual components.

Any of the embodiments described above relating to different ways of characterizing System A+M may be combined with each other in any combination.

In a further aspect the invention provides a pharmaceutical composition comprising a pharmaceutically effective amount of the crystalline dichloride salt (System A+M) of the compound of formula I in combination with a pharmaceutically acceptable carrier, diluent or excipient.

In a further aspect the invention provides a crystalline dichloride salt of the compound of formula I (System A+M) for use in the treatment of a proliferative disorder or disease.

In a further aspect the invention provides use of a crystalline dichloride salt of the compound of formula I (System A+M) in the manufacture of a medicament for use in the treatment of a proliferative disorder or disease.

In a further aspect the invention provides a method of treating a proliferative disorder or disease comprising administering a crystalline dichloride salt of the compound of formula I (System A+M) to a patient in need thereof.

The term "treatment," as used herein in the context of treating a disease or disorder, pertains generally to treatment and therapy, whether of a human or an animal (e.g., in veterinary applications), in which some desired therapeutic effect is achieved, for example, the inhibition of the progress of the disease or disorder, and includes a reduction in the rate of progress, a halt in the rate of progress, alleviation of symptoms of the disease or disorder, amelioration of the disease or disorder, and cure of the disease or disorder. Treatment as a prophylactic measure (i.e., prophylaxis) is also included. For example, use with patients who have not yet developed the disease or disorder, but who are at risk of developing the disease or disorder, is encompassed by the term "treatment." For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The compound of formula I or a pharmaceutically acceptable derivative thereof may be administered in a pharmaceutical composition, as is well known to a person skilled in the art. Suitable compositions and dosages are for example disclosed in WO 2004/103994 A1 pages 35-39, which are specifically incorporated by reference herein. Compositions may be administered nasally, buccally, rectally, orally or parenterally. Parenteral administration includes for example intravenous, intramuscular and subcutaneous administration, to warm-blooded animals, especially humans. More particularly, compositions for intravenous or oral administration are preferred. The compositions comprise the active ingredient and one or more pharmaceutically acceptable excipients, if applicable.

Pharmaceutically acceptable excipients include diluents, carriers and glidants etc. as known by the person skilled in the art. An example of a composition for oral administration includes, but is not limited to, hard capsules containing 1 mg active ingredient, 98 mg diluent e.g. mannitol and 1 mg glidant e.g. magnesium stearate, or 5 mg active ingredient, 94 mg diluent e.g. mannitol and 1 mg glidant e.g. magnesium stearate. For intravenous application, for example, the active ingredient can be lyophilized and reconstituted with as suitable diluent e.g. saline solution immediately prior to administration.

A compound of formula I or a pharmaceutically acceptable derivative thereof can be administered alone or in combination with one or more other therapeutic agents. Possible combination therapy may take the form of fixed combinations, or the administration of a compound of the invention and one or more other therapeutic agents which are staggered or given independently of one another, or the combined administration of fixed combinations and one or more other therapeutic agents. A compound of formula I or a pharmaceutically acceptable derivative thereof can, besides or in addition, be administered especially for tumor therapy in combination with chemotherapy (cytotoxic therapy), targeted therapy, endocrine therapy, biologics, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemo-preventive therapy, for example in patients at risk.

The compounds according to formula (I) may be used for the prophylactic or especially therapeutic treatment of the human or animal body, in particular for treating proliferative diseases or disorders, such as a neoplastic disease. Examples of such neoplastic diseases include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and *glomus* tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non-Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

In an especially preferred embodiment the disease is cancer. Examples of cancers in terms of the organs and parts of the body affected include, but are not limited to, the brain, breast, cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis.

Preferably the cancer is selected from the group consisting of brain cancer (e.g. glioblastoma) breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas.

In one embodiment the cancer to be treated is a tumor, preferably a solid tumor.

In a further embodiment the neoplastic disease is a brain neoplasm, e.g. a brain tumor, which include but are not limited to glial- and non-glial-tumors, astrocytomas (incl. glioblastoma multiforme and unspecified gliomas), oligo-dendrogliomas, ependydomas, menigiomas, haemangioblastomas, acoustic neuromas, craniopharyngiomas, primary central nervous system lymphoma, germ cell tumors, pituitary tumors, pineal region tumors, primitive neuroectodermal tumors (PNET's), medullablastomas, haemangiopericytomas, spinal cord tumors including meningiomas, chordomas and genetically-driven brain neoplasms including neurofibromatosis, peripheral nerve sheath tumors and tuberous sclerosis. Preferably, brain neoplasm refers to glioblastomas (also referred to as glioblastoma multiforme).

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded or reduced when necessary.

The terms "dichloride salt of the compound of formula I" and "dihydrochloride salt of the compound of formula I" are used interchangeably and both refer to the 2xHCl salt of the compound of formula I.

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

The invention will now be described by way of non-limiting examples.

BRIEF DESCRIPTION OF THE FIGURES

FIG. 1 shows the atom numbering for NMR assignments.

FIG. 2 shows the X-ray powder diffraction (XRPD) diffractogram of the crystalline form E of the dichloride salt of the compound of formula I at room temperature.

FIG. 3 shows the graphical representation of the Pawley (WPPD) calculation for the crystalline form E of the dichloride salt of the compound of formula I. The graphical representation of the whole powder pattern decomposition calculation is presented, where the upper line shows observed data from a high resolution XRPD. The black middle line presents the calculated powder pattern and the black sticks at the very bottom of the figure are indicating the position of peaks with their h, k, 1 indices. The grey bottom line represents the difference between calculated and (baseline corrected) observed points.

FIG. 6 shows the cyclic DSC for the crystalline Form E of the dichloride salt of the compound of formula I using the temperature profile 25→200→25° C.; a heating rate of 10° C./min and fast cooling. The endotherm (130° C.±2° C.) indicates a solid-solid transition, which is reversible (exotherm at 97° C.±2° C. upon cooling).

FIG. 7 shows the XRPD diffractogram of the crystalline high temperature Form E1 of the dichloride salt of the compound of formula I at 180° C.

FIG. 8 shows the FTIR spectrum of the compound of formula I for the crystalline Form E of the dichloride salt of the compound of formula I.

FIG. 9 shows the zoom between 1830 and 400 cm-1 of the FTIR spectrum for the crystalline Form E of the dichloride salt of the compound of formula I.

FIG. 10 shows the magic angle spinning solid state carbon 13 {proton decoupled} nuclear magnetic resonance (13C {1H} MAS-NMR) spectrum for the crystalline Form E of the dichloride salt of the compound of formula I.

FIG. 11 shows the isothermic (24.1° C.) dynamic vapor sorption analysis for the crystalline Form E of the dichloride salt of the compound of formula I.

FIG. 12 shows the XRPD diffractogram of Form A0.

FIG. 13 shows the XRPD diffractogram of Form A1.

FIG. 14 shows the XRPD diffractogram of Mixture A1+M1.

FIG. 15 shows the XRPD diffractogram of Mixture A1+M4.

FIG. 16 shows the XRPD diffractogram of Mixture M3+M5.

FIG. 17 shows the XRPD diffractogram of Mixture A2+M4.

FIG. 18 shows the XRPD diffractogram of Mixture A2+M11.

FIG. 19 shows an overlay of XRPD diffractograms of (from bottom to top) F: Forms A1+M4, E: after 1 week at 40° C. 75% RH (M3+M5), D: after 2.5 weeks at 40° C./75% RH (M3+M5), C: after 4 weeks at 40° C./75% RH (M5), B: after 4 weeks at 40° C./75% RH and 2 days 25° C./95% RH (A2+M4), A: after 4 weeks at 40° C./75% RH and 1 week at 25° C./95% RH (A2+M11).

FIG. 20 shows the XRPD diffractogram of Form A2.

FIG. 21 shows the XRPD diffractogram of Mixture A2+A3.

FIG. 22 shows the XRPD diffractogram of Form M1.

FIG. 23 shows the XRPD diffractogram of Form M2.

FIG. 24 shows the XRPD diffractogram of Form M3+M5.

FIG. 25 shows the XRPD diffractogram of Form M4.

FIG. 26 shows the XRPD diffractogram of Form M5.

FIG. 27 shows the XRPD diffractogram of Form M8.

FIG. 28 shows the XRPD diffractogram of Form M9.

FIG. 29 shows the XRPD diffractogram of Mixture M10+M4.

FIG. 30 shows the XRPD diffractogram of Form M11.

FIG. 31 shows the XRPD diffractogram of Form M12.

FIG. 32 shows the XRPD diffractogram of Form M13.

FIG. 33 shows the XRPD diffractogram of Form F.

FIG. 34 shows the XRPD diffractogram of Form G.

FIG. 35 shows the isothermic (24.9° C.) dynamic vapor sorption measurement of the compound of formula I presenting the relative sample weight (%) versus the relative humidity. The starting form was Mixture A1+M4 and the humidity profile was 0→95→0% RH with steps of 10% RH until mass equilibration was achieved per step. The maximum mass change was 34% at 95% RH. No hysteresis was observed.

FIG. 36 shows the thermodynamic pH-dependent solubility of Form E.

FIG. 37A shows the thermodynamic pH-dependent solubility of Form A1+M4. FIG. 37B shows the thermodynamic pH-dependent solubility of Form A2+M11.

FIG. 38 shows the XRPD diffractogram of the dichloride salt of the compound of formula I produced according to the methodology of WO 2011/012577 and which is described on page 36, final paragraph, of WO 2011/012577. The upper XRPD plot is from sample stored at 5° C., the lower XRPD plot is from sample stored at −60° C.

EXAMPLES

Figure 1:
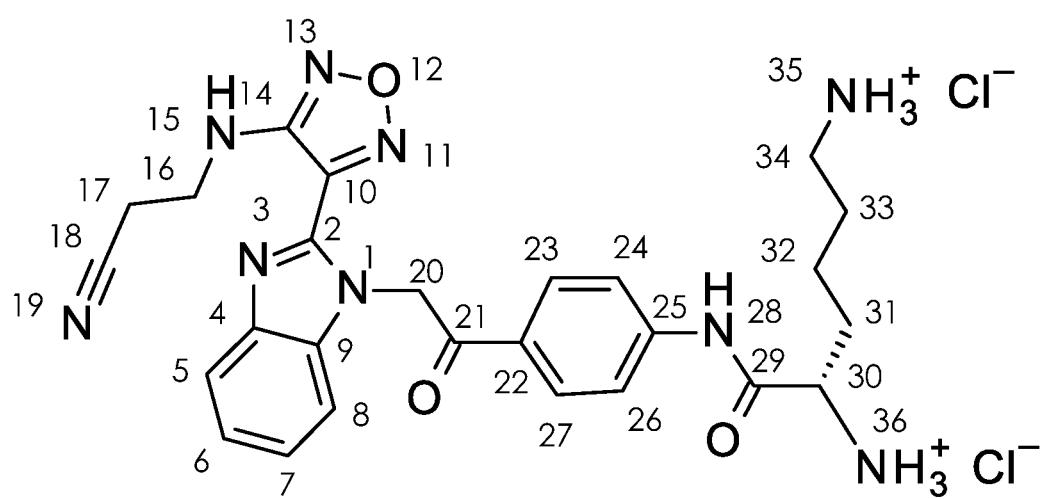
FIG. 1

Example 1—Synthesis of the Compound of Formula III

Example 1a: Synthesis of the compound of formula III ($R^1$=Cl, $R^3$=tert-butyl) by activation with DCC A solution of phosphoric acid (85%, 57 mL) in water (280 mL) was added to a suspension of N2,N6-bis(tert-butoxycarbonyl)-L-lysine dicyclohexylamine salt (438 g, 0.831 mol, 2.5 eq.) in diisopropyl ether (DIPE, 1 L) at room temperature and stirred until dissolution of the solids. The organic phase was washed with a mixture of phosphoric acid (85%, 20 mL) and water (160 mL), then with water (4×160 mL). After drying over anhydrous sodium sulfate the solution of bis(tert-butoxycarbonyl)-L-lysine (free acid) was concentrated. The concentrate was diluted with dichloromethane (DCM, 421 mL). A solution of dicyclohexylcarbodiimide (88.5 g, 0.429 mol, 1.25 eq.) in DCM (100 mL) was added at room temperature and the reaction mixture was stirred for 15 min. The resulting suspension was filtered, the cake washed with DCM (3×50 mL). 4-aminophenacyl chloride (56.2 g, 0.331 mol, 1.0 eq.) was added to the combined filtrates and the mixture was stirred for 4 h. Insoluble matter was filtered off and the filtrate was concentrated in vacuo. The concentrate was diluted with 4-methyl-2-pentanone (MIBK, 279 mL), heated to ca. 45° C. Heptane (836 mL) was added with cooling. The suspension was cooled to 10° C., stirred and filtered. The solid was washed with MIBK/heptane and heptane and dried. The crude product was crystallized from MIBK/heptane and dried to provide 119.4 g of the title compound (72%) in a purity of ≥99.5% and ≥99% ee.

Example 1b: Synthesis of the Compound of Formula III ($R^1$=Cl, $R^3$=Tert-Butyl) by Activation with T3P®

N2,N6-bis(tert-butoxycarbonyl)-L-lysine (85% w/w, 216 g, 531 mmol, 1.5 eq.) was dissolved in toluene (1500 g). A solution of 4-aminophenacyl chloride (60 g, 354 mmol, 1.0 eq.) and 4-(dimethylamino)-pyridine (DMAP, 4.32 g, 35.4 mmol, 0.1 eq.) in toluene (600 g) was added. The mixture was cooled to −15 to ~10° C. Triethylamine (143 g, 1.42 mol, 4.0 eq.) was added followed by dosing of a solution of 2,4,6-tripropyl-1,3,5,2,4,6-trioxatriphosphorinane-2,4,6-trioxide (T3P®, 495 g of a 50% solution in toluene, 778 mmol, 2.2 eq.) in toluene (360 g) over 2 h at −15 to −10° C. The mixture was stirred for 17 h and warmed to ca. −5° C. Water (1524 g) was added and phases were separated at room temperature. The organic phase was washed with hydrochloric acid (pH1.0), then with hydrochloric acid (pH=0.5, 5% w/w ethanol) and with saturated aqueous sodium bicarbonate solution. The solution was filtered and allowed to stand. The suspension was concentrated at 30-35° C., 50 mbar, cooled to ca. 20° C. and stirred. The solid was filtered, washed with toluene and dried to provide 138.5 g of the title compound (79%) in a purity of 99.3% and ≥99% ee.

Example 2-Synthesis of the Compound of Formula II ($R^3$ is Tert-Butyl)

3-{[4-(1H-Benzoimidazol-2-yl)-1,2,5-oxadiazol-3-yl]amino} propanenitrile (47 g, 185 mmol, 1.00 eq) was dissolved in DMF (1.6 L). N-[4-(2-chloroacetyl)phenyl]-

N2,N6-di-Boc-L-lysinamide (98 g, 197 mmol, 1.06 eq.) and potassium carbonate (49.5 g, 358 mmol, 1.94 eq.) was added. The mixture was heated to 40° C. for 5 h. The suspension was filtered and the filtrate was dosed to aqueous ammonium chloride solution (2.5% w/w, 7 L) at 0-5° C. The suspension was filtered and the solid was dried. The crude product was suspended in THF (188 mL) and water (100 mL). Methanol (3.4 L) was added at reflux (ca. 65° C.). The suspension was stirred for 1 hour and cooled to room temperature. The product was filtered, the solids washed with methanol and dried. The solids were heated to reflux in THF (188 mL) and methanol (3.4 L), and cooled to ca. 10° C. within 2 h. The suspension was filtered, washed with methanol and dried to provide 121 g of the title compound (91%) in a purity of 99.8%.

Example 3-Synthesis of the Compound of Formula I (Dihydrochloride)

The compound of formula II ($R^3$ is tert-butyl) (119 g, 166.4 mmol, 1.00 eq.) was suspended in tetrahydrofuran (785 mL) and heated to 30° C. Aqueous hydrochloric acid (30% w/w, 170 g) was added within 3 h. The mixture was stirred for 48 h, cooled to 10° C., and tetrahydrofuran (785 mL) was added. The resulting suspension was filtered, the cake is washed with tetrahydrofuran and dried at up to 55° C. to provide 95.8 g (97.8%) crude product. The crude product (75 g) was dissolved in water (75 mL) and tetrahydrofuran (112 mL) at ca. 43° C. Tetrahydrofuran (2.85 L) was added at ca. 40° C. and the suspension was stirred at ca. 50° C. for 1 hour. After cooling to 10° C. the product was filtered, washed with tetrahydrofuran and dried at ca. 50° C. to provide 68 g of purified product. The purified product (67 g) was dissolved in water (201 mL) and the resulting solution was filtered. Water was evaporated. The product was further dried at up to 50° C. to provide 62.9 g of the title compound (83%) in a purity of 99.6%.

Comparative Example 1 (According to WO 2011/012577)

S-{5-benzyloxycarbonylamino-5-[4-(2-{2-[4-(2-cyanoethylamino) furazan-3-yl]-benzoimidazo-1-1-yl}-acetyl)-phenylcarbamoyl]-pentyl}-carbamic acid benzylester was hydrogenated in a mixture of THF/MeOH/HCl with hydrogen in the presence of Pd/C 10% for ca. 5 h. After work-up, chromatography and salt formation this resulted in the dihydrochloride of the compound of formula I with a purity of 90-91%, 81% ee (yield: 50%).

Example 4-Preparation of the Crystalline Dichloride Salt (Form E) of the Compound of Formula I Some of the Examples below describe preparation of Form E using seed crystals. The main purpose of adding seed crystals was to speed up formation of the polymorph. It is believed that without seed crystals the Examples would have still resulted in Form E. Note that Examples 4d, 4f, 4 g, 4h, 4i and 4k did not use seed crystals, as well as 4l, 4m, 4n, 4o and 4p.
Crystallization by Slurry Example 4a: From Methanol/Methyl Tert-Butylether (MTBE)

0.20 g of the compound of formula I was dissolved in 8 mL methanol at 65° C., the solution was filtered. 10 mg seeds of Form E were added and the mixture was stirred over 30 min. 12 mL MTBE was added dropwise over 2-3 h, the mixture obtained was cooled to 5-15° C. and stirred for ca. 40 h at 5-15° C. The mixture was filtered and the cake was dried under vacuum, providing 0.18 g solid of Form E.

Example 4b: From Methanol/Acetonitrile 4 g of the compound of formula I (Mixture A1+M1) is dissolved in 40 mL methanol and 30-45° C. The solution was filtered and 200 mg seeds of Form E were charged into the solution. After stirring a suspension formed which was heated to reflux over ca. 15 h and concentrated to 12 mL. 20 mL acetonitrile was added, the suspension cooled slowly to 0-10° C. and filtered. The cake was dried at ca. 50° C. under vacuum, providing 3.4 g solid of Form E.

Example 4c: From Methanol/Toluene 2 g of the compound of formula I (Mixture A1+M1) was dissolved in 20 mL methanol and the mother liquid from last batch at 30-45° C. The solution was filtered, seeded with 100 mg Form E and added dropwise to 50 mL hot toluene (80-90° C.). The resulting suspension was concentrated (ca. 20 mL solvent distilled off), further heated to the boiling point and then slowly cooled to 0-10° C. The suspension was filtered and the cake was dried at 50° C. under vacuum, providing 1.5 g of Form E.

Example 4d: From Methanol (Room Temperature Slurry)

65 g of the compound of formula I (Mixture A1+M1) was dissolved in 485 mL methanol and stirred at 15-25° C. The solution was stirred for ca. 14 days. During stirring a suspension was formed. The suspension was filtered, the cake was washed with methanol and dried at ca. 50° C. under vacuum, providing 46 g of Form E.

Example 4e: From Methanol (Slurry at Reflux)

2 g of the compound of formula I (Mixture A1+M4) was dissolved in 20 mL methanol at 30-45° C. The solution was filtered, seeded with form E and refluxed for ca. 15 h. The suspension was concentrated to a volume of ca. 10 mL, cooled to 0-10° C. and filtered. The cake was dried at 50° C. under vacuum, providing 1.37 g of Form E.

Example 4f: From Ethanol 5 g of the compound of formula I (Mixture A1+M1) were refluxed in 100 mL ethanol for a total of 11 h. The mixture was cooled to room temperature, filtered and the cake was dried at 45° C. under vacuum, providing 4.45 g of Form E.

Example 4g: From Acetonitrile, Reflux 15 g of the compound of formula I (Mixture A1+M1) were refluxed in 300 mL acetonitrile for a total of 11 h. The suspension was cooled to room temp and filtered, filtered and the cake was dried at 65° C. under vacuum, providing 13 g of Form E.

Example 4h: From Ethyl Acetate, Slurry at Room Temperature (RT) and 50° C.

20.4 mg of the compound of formula I (Mixture A1+M1) were stirred for two weeks in 1 mL of ethyl acetate at room temperature. Afterwards the samples were centrifuged and solids and mother liquor were separated. The wet solid was analyzed to be a mixture of Form E and Form F as a minor polymorph. The wet solid was dried at room temperature under vacuum (5 mbar) for ca. 18 h and analyzed to be Form E.

28.4 mg of the compound of formula I (Mixture A1+M1) were stirred for two weeks in 1 mL of ethyl acetate at ca. 50° C. Afterwards the samples were centrifuged and solids and mother liquor were separated. The wet solid was analyzed to be a mixture of Form E and F as a minor polymorph. The wet solid was dried at room temperature under vacuum (5 mbar) for ca. 18 h and analyzed to be Form E.

Example 4i: From 2-Propanol 27.5 mg of the compound of formula I (Mixture A1+M1) were stirred for ca. two weeks in 0.9 mL of 2-propanol at 50° C. Afterwards the samples were centrifuged and solids and mother liquor were separated. The wet solid was analyzed to be Form E. The wet solid was dried at room temperature under vacuum (5 mbar) for ca. 18 h and analyzed to be Form E.

Example 4j: From Ethyl Acetate 19.8 mg of the compound of formula I (Mixture A1+M1) were stirred for ca. two weeks in 0.6 mL of ethyl acetate at 20° C. Afterwards the samples were centrifuged and solids and mother liquor were separated. The wet solid was analyzed to be Form E. The wet solid was further treated for 2 days at 40° C./75% RH and analyzed to be Form E.

Example 4k: From Acetonitrile, 20° C.

18.0 mg of the compound of formula I (Form A1+M1) were stirred for ca. two weeks in 0.6 mL of acetonitrile at 20° C. Afterwards the samples were centrifuged and solids and mother liquor were separated. The wet solid was analyzed to be Form E. The wet solid was further treated for 2 days at 40° C./75% RH and analyzed to be Form E.

In a second trial the wet solid was 18.0 mg of the compound of formula I were stirred for ca. two weeks in 0.6 mL of acetonitrile at 20° C. Afterwards the samples were centrifuged and solids and mother liquor were separated. The wet solid was analyzed to be Form E. The wet solid was dried at room temperature under vacuum (5 mbar) for ca. 18 h and analyzed to be Form E.

Example 4l from Acetonitrile, 50° C.

18.0 mg of the compound of formula I (Form A1+M1) were stirred for ca. two weeks in 0.6 mL of acetonitrile at 50° C. Afterwards the samples were centrifuged and solids and mother liquor were separated. The wet solid was analyzed to be Form E. The wet solid was further treated for 2 days at 40° C./75% RH and analyzed to be Form E.

Crystallisation by cooling

Example 4m: From 2-Butanol/Methanol 35.5 mg of the compound of formula I (Mixture A1+M1) were added in 1.2 mL of a mixture of 2-butanol/methanol resulting in a slurry which was stirred at ca. 60° C. for one hour. Afterwards the sample was held for one hour at 60° C. and allowed to cool down to ca. 5° C. with a cooling rate of ca. 1° C./h. The sample was kept at ca. 5° C. for ca. 24 h. The wet solid was filtrated and analyzed to be Form E.

Example 4n: From 4-Dioxane/Methanol 32.5 mg of the compound of formula I (Mixture A1+M1) were added in 0.5 mL of a mixture of methanol/1,4-dioxane resulting in a slurry which was stirred at ca. 60° C. for one hour. Afterwards the sample was held for one hour at 60° C. and allowed to cool down to ca. 5° C. with a cooling rate of ca. 1° C./h. The sample was kept at ca. 5° C. for ca. 24 h. The wet solid was filtrated and analyzed to be Form E.

Example 4o: From Ethyl Acetate/Methanol 32.5 mg of the compound of formula I (Mixture A1+M1) were added to 0.75 mL of a mixture of ethyl-acetate/methanol resulting in a slurry which was stirred at ca. 60° C. for one hour. Afterwards the sample was held for one hour at ca. 60° C. and allowed to cool down to ca. 5° C. with a cooling rate of ca. 1° C./h. The sample was kept at ca. 5° C. for ca. 24 h. The wet solid was filtrated and analyzed to be Form E.

One-Pot Deprotection of the Compound of Formula II and Crystallisation

Example 4p 0.5 g of the compound of formula II ($R^3$ is tert-butyl) was suspended in 5 mL methanol. 2.4 molar equivalents of HCl in MeOH was added at 20-25° C. and the suspension was stirred for ca. 9 days at ca. 5° C. The suspension was filtered and the cake obtained was dried under vacuum, providing 0.3 g of Form E.

Crystallisation from Free Base

Example 4q 76 g of the dichloride salt of the compound of formula I (Mixture A1+M4) was dissolved in a mixture of 280 mL water and 280 mL methanol. The solution was added to a solution of 24.2 g potassium carbonate, 140 mL water and 140 mL methanol at 10-15° C. The reaction mixture was stirred for ca. 2 hours at room temperature. The suspension was filtered, the cake was washed with methanol, and slurried in 350 mL of water and 350 mL of methanol. The suspension was filtered, the cake was washed with 70 mL of water and dried under vacuum at 45° C., providing 65 g of the compound of formula I (free base).

1 g of the compound of formula I (free base) was reacted with hydrochloric acid in methanol solution at 65° C. 10 mg seeds of Form E were added, the mixture was slowly cooled to 8-10° C., stirred for ca. 16 h filtered and the cake obtained was dried under vacuum to provide 0.44 g of Form E.

Example 5-Characterization of the Crystalline Dichloride Salt (Form E) of the Compound of Formula I Example 5a: Characterization by XRPD XRPD patterns were obtained using a high-throughput XRPD set-up. The plates were mounted on a Bruker GADDS diffractometer equipped with a Hi-Star area detector. The XRPD platform was calibrated using Silver Behenate for the long d-spacings and Corundum for the short d-spacings. Data collection was carried out at room temperature using monochromatic CuKα radiation in the 2θ region between 1.5° and 41.5°, which is the most distinctive part of the XRPD pattern. The diffraction pattern of each well was collected in two 2θ ranges (1.5° 2θ≤21.5° for the first frame, and 19.5°% 2θ≤41.5° for the second) with an exposure time of 90 s for each frame. No background subtraction or curve smoothing was applied to the XRPD patterns. The carrier material used during XRPD analysis was transparent to X-rays and contributed only slightly to the background.

Figure 2:
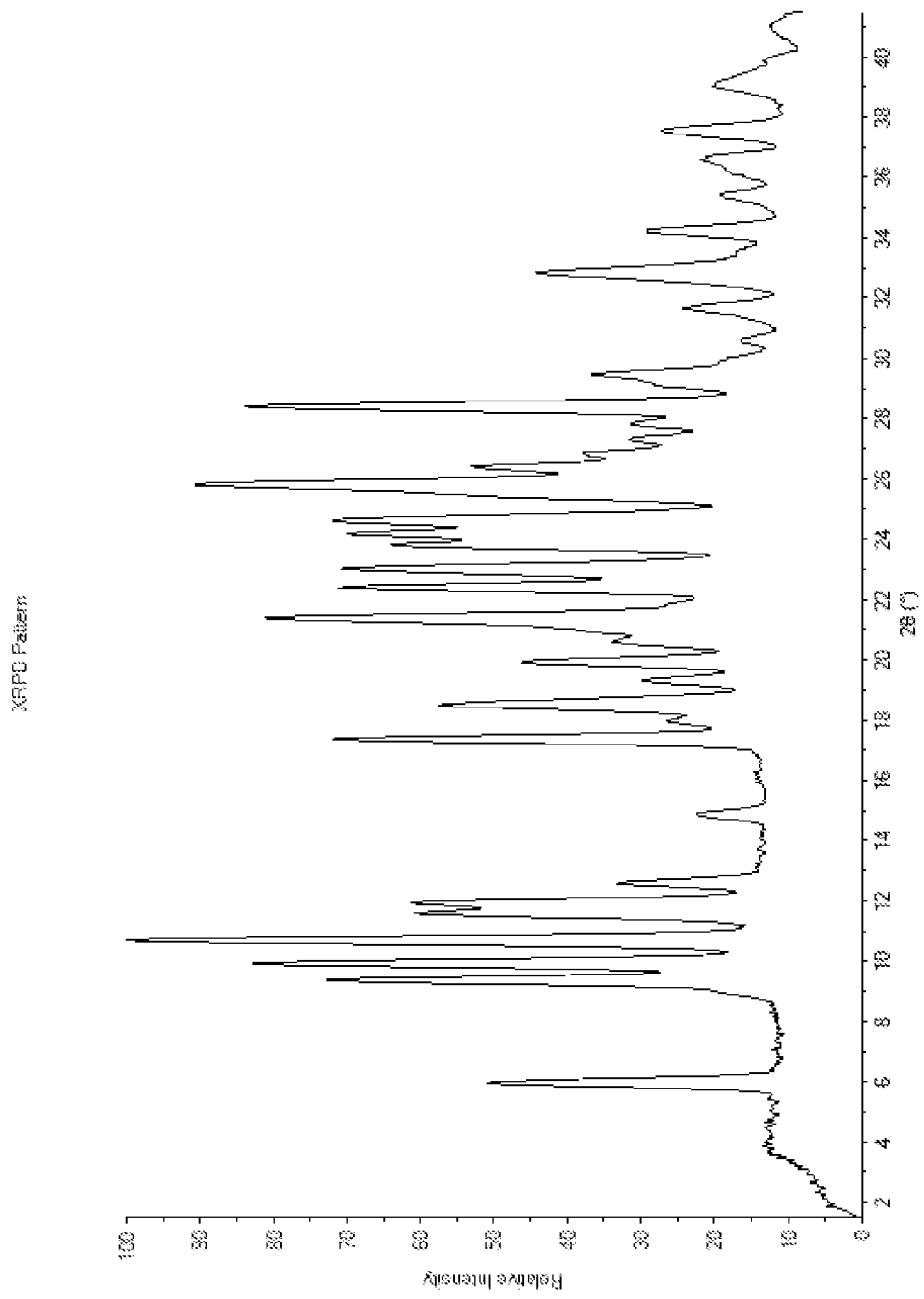
FIG. 2

The XRPD of the crystalline form of the dichloride salt of the compound of formula I (Form E) at room temperature is shown in FIG. 2 and its diffractogram peaks are shown in Table 2. The evaluation of the high-resolution XRPD pattern was indexed using a P222 space group. Indexing the intensities of reflections of the pure form resulted in an orthorhombic crystal system and allowed extraction of the cell parameters.

Figure 3:
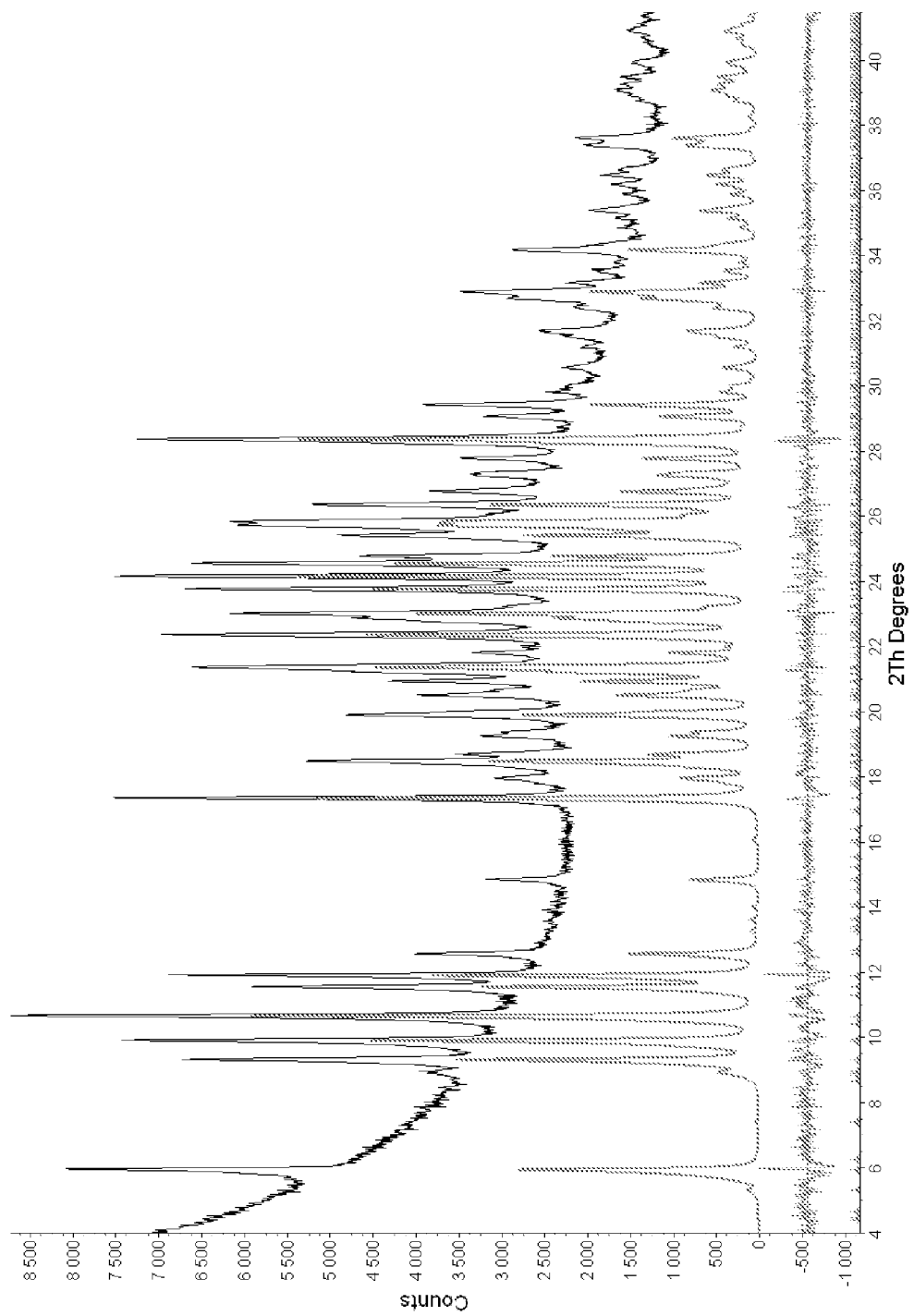
FIG. 3

The crystallographic parameters are based on a Pawley calculation (whole powder pattern decomposition, WPPD) for the crystalline form of the dichloride salt of the compound of formula I. All intensities and 2θ values for the peaks from the powder diffraction pattern could be assigned for the orthorhombic primitive cell (P), with the cell parameters: a=4.8 Å, b=20.02 Å, c=59.40 Å; V=5724 Å$^3$ (a=4.813±0.001 Å, b=20.02±0.01 Å, c=59.40±0.02 Å, V=5724±5 Å$^3$). The powder pattern of this form could also be indexed in the lower symmetries such as monoclinic (a=10.08 Å; b=59.42 Å; c=5.16 Å; beta=97.28 Å; V=3065 Å3) and several triclinic. However, as a general rule the highest symmetry is applied. In this case the highest symmetry is orthorhombic. A comparison of the calculated and measured diffractograms shows excellent agreement as depicted in FIG. 3.

TABLE 2

X-ray powder diffraction (XRPD) list of diffractogram peak positions, d-spacing, and relative intensities of the 27 most abundant peaks for the crystalline Form E of the dichloride salt of the compound of formula I

| Angle [2θ] | d-Spacing [Å] | Intensity [rel. %] |
|---|---|---|
| 6.0 | 14.76 | 49 |
| 9.4 | 9.42 | 69 |
| 9.9 | 8.89 | 81 |
| 10.7 | 8.26 | 100 |
| 11.6 | 7.61 | 55 |
| 11.9 | 7.43 | 56 |
| 12.6 | 7.03 | 25 |
| 17.4 | 5.10 | 64 |
| 18.5 | 4.79 | 46 |
| 19.9 | 4.45 | 31 |
| 21.4 | 4.15 | 68 |
| 22.4 | 3.96 | 53 |
| 23.0 | 3.86 | 54 |
| 23.8 | 3.73 | 45 |
| 24.2 | 3.68 | 51 |
| 24.6 | 3.61 | 56 |
| 25.8 | 3.45 | 79 |
| 26.4 | 3.37 | 35 |
| 28.4 | 3.14 | 75 |
| 32.8 | 2.73 | 42 |
| 34.2 | 2.62 | 25 |

Figure 10:
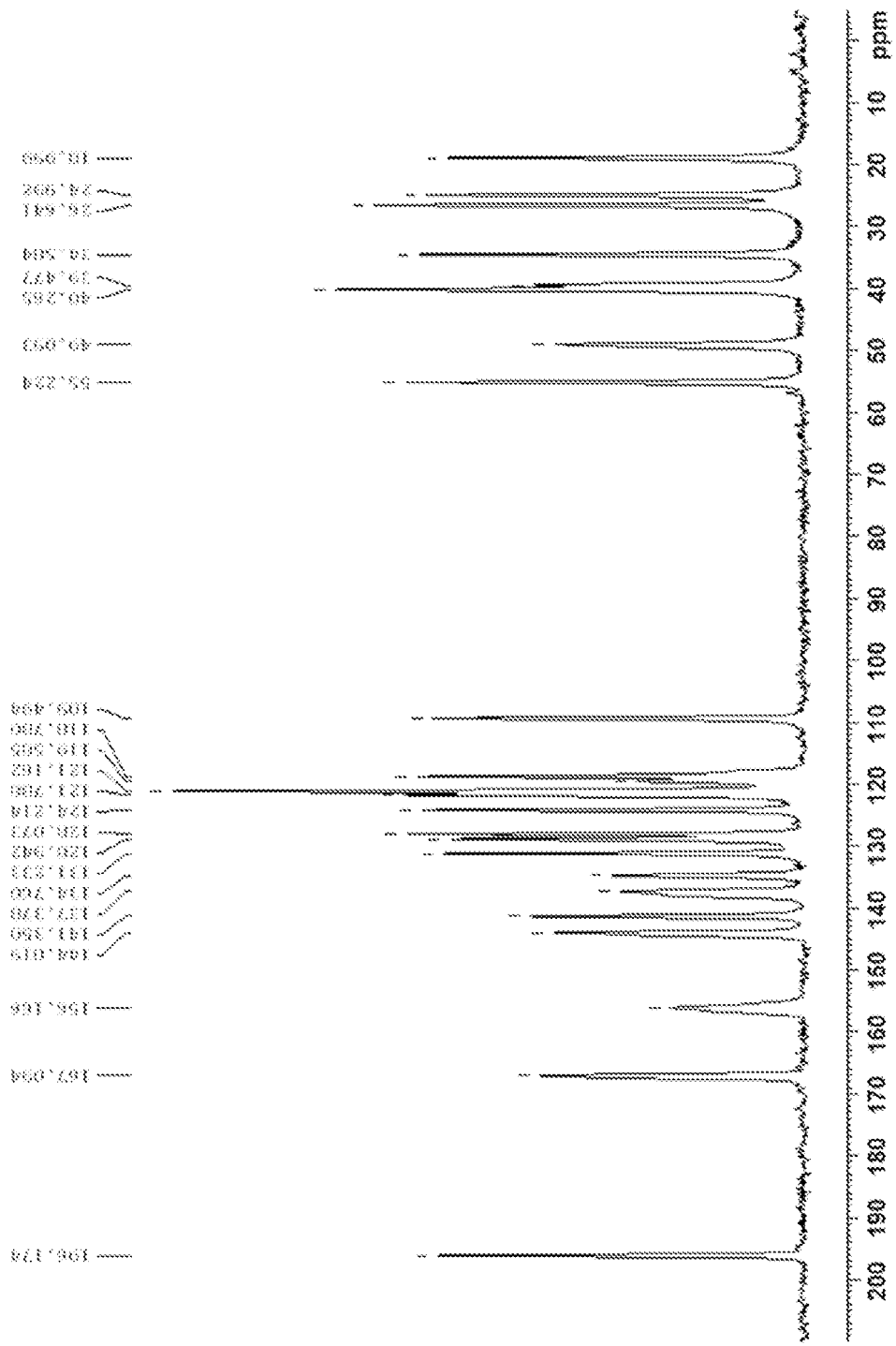
FIG. 10

The XRPD of the high-temperature polymorph form E1 was determined similarly to form E and the diffractogram peaks (FIG. 10) are shown in Table 3.

TABLE 3

X-ray powder diffraction (XRPD) list of diffractogram peak positions, d-spacing, and relative intensities for the crystalline high-temperature Form E1 of the dichloride salt of the compound of formula I

| Angle [2θ] | d-Spacing [Å] | Intensity [rel. %] |
|---|---|---|
| 6.0 | 14.79 | 55 |
| 9.0 | 9.85 | 9 |
| 9.4 | 9.46 | 57 |
| 9.9 | 8.91 | 77 |
| 10.7 | 8.29 | 100 |
| 11.6 | 7.64 | 53 |
| 11.9 | 7.41 | 72 |
| 12.6 | 7.02 | 24 |
| 17.4 | 5.10 | 89 |
| 18.5 | 4.79 | 50 |
| 19.9 | 4.45 | 42 |
| 20.5 | 4.32 | 26 |
| 21.0 | 4.23 | 30 |
| 21.2 | 4.18 | 42 |
| 21.4 | 4.15 | 70 |
| 22.4 | 3.97 | 78 |
| 23.0 | 3.86 | 65 |
| 23.8 | 3.74 | 72 |
| 24.2 | 3.68 | 84 |
| 24.6 | 3.62 | 77 |
| 24.8 | 3.59 | 39 |
| 25.4 | 3.50 | 46 |
| 25.8 | 3.46 | 67 |
| 25.9 | 3.44 | 65 |
| 26.4 | 3.38 | 51 |
| 26.8 | 3.32 | 27 |
| 27.8 | 3.21 | 25 |
| 28.4 | 3.14 | 86 |
| 29.1 | 3.07 | 20 |
| 29.5 | 3.03 | 33 |

Figure 4:
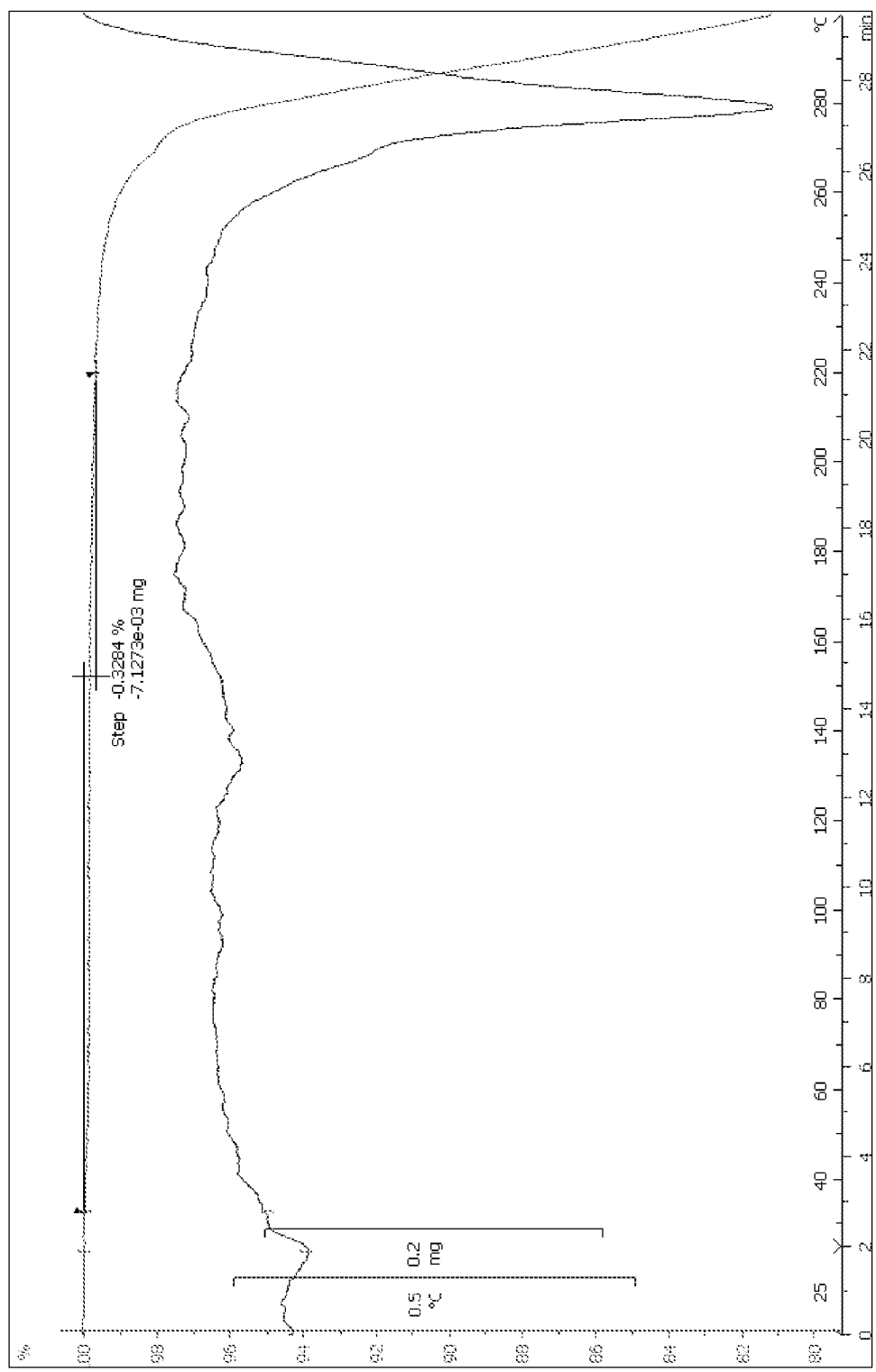
FIG. 4 shows the thermogravimetric analysis (TGA) of the crystalline Form E of the dichloride salt of the compound of formula I with endothermic peaks at about 130° C. (±2° C.) and 276° C. (±2° C.).
Figure 5:
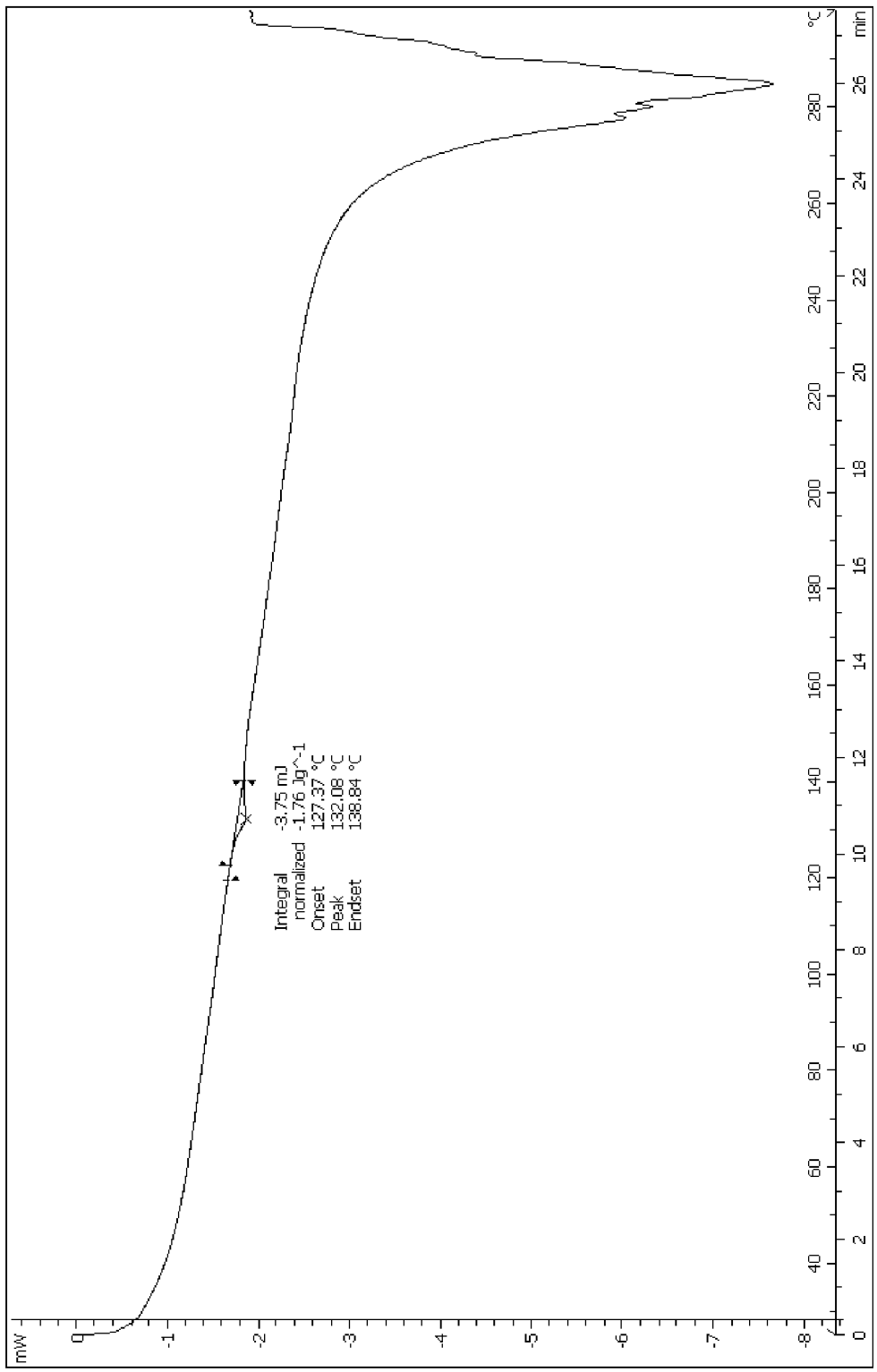
FIG. 5 shows the differential scanning calorimetry (DSC) of the crystalline Form E of the dichloride salt of the compound of formula I with endothermic peaks at about 130° C. (±2° C.) and 276° C. (±2° C.) as well as decomposition above this temperature.

Example 5b: Characterization by Differential Scanning Calorimetry (DSC), Thermogravimetric Analysis (TGA), and Variable Temperature XRPD The thermogravimetric analysis (TGA, FIG. 4) showed a large endotherm indicated a melting event at about 276° C. (±2° C.) accompanied by decomposition. A small endotherm at about 130° C. (±2° C.) implied that a solid-solid transition to a crystalline form variation, built reversibly at high temperatures, occurred prior to melting. This behavior was confirmed by differential scanning calorimetry (DSC, FIG. 5) as well as by variable temperature XRPD studies.

Figure 6:
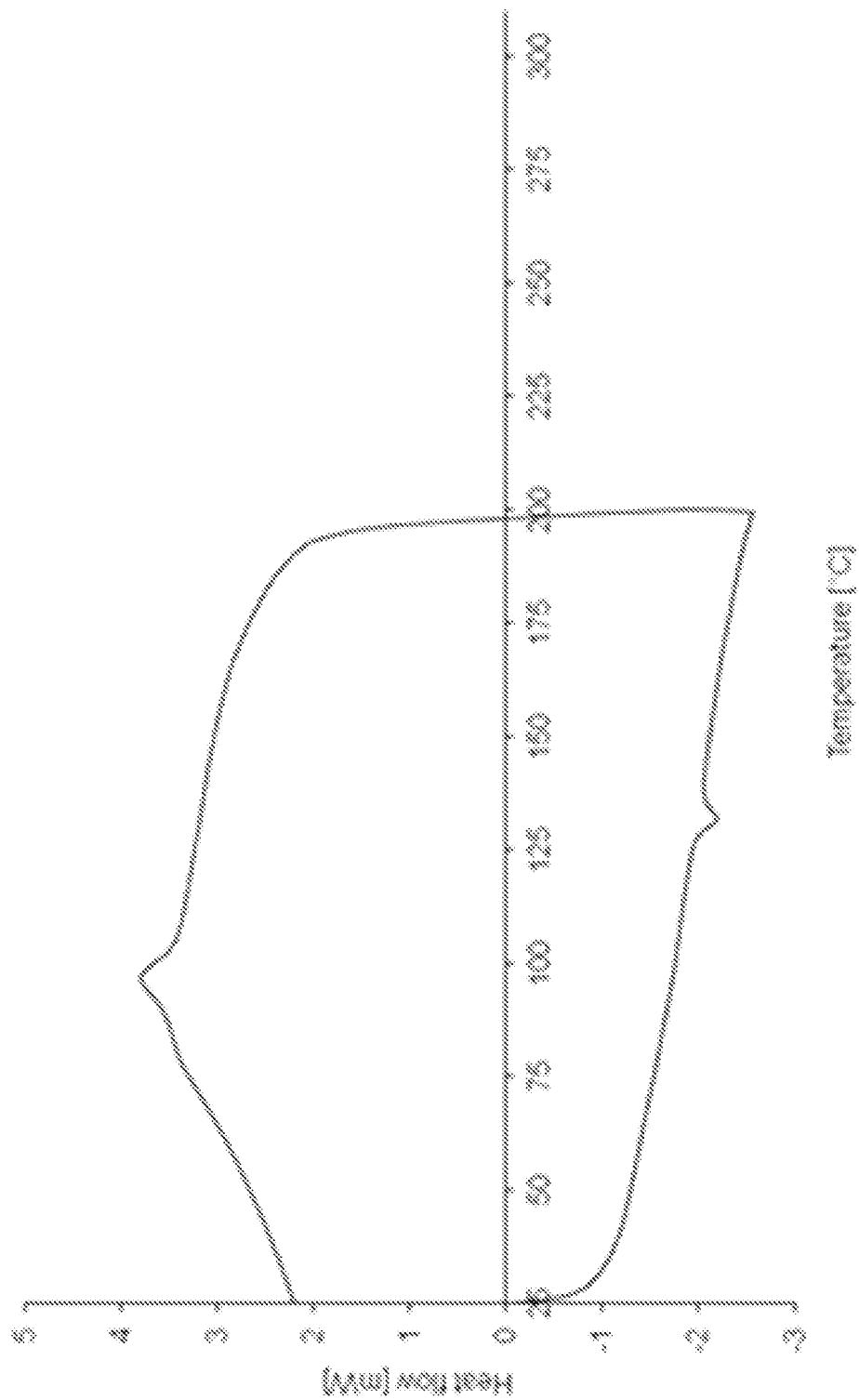
FIG. 6
Figure 7:
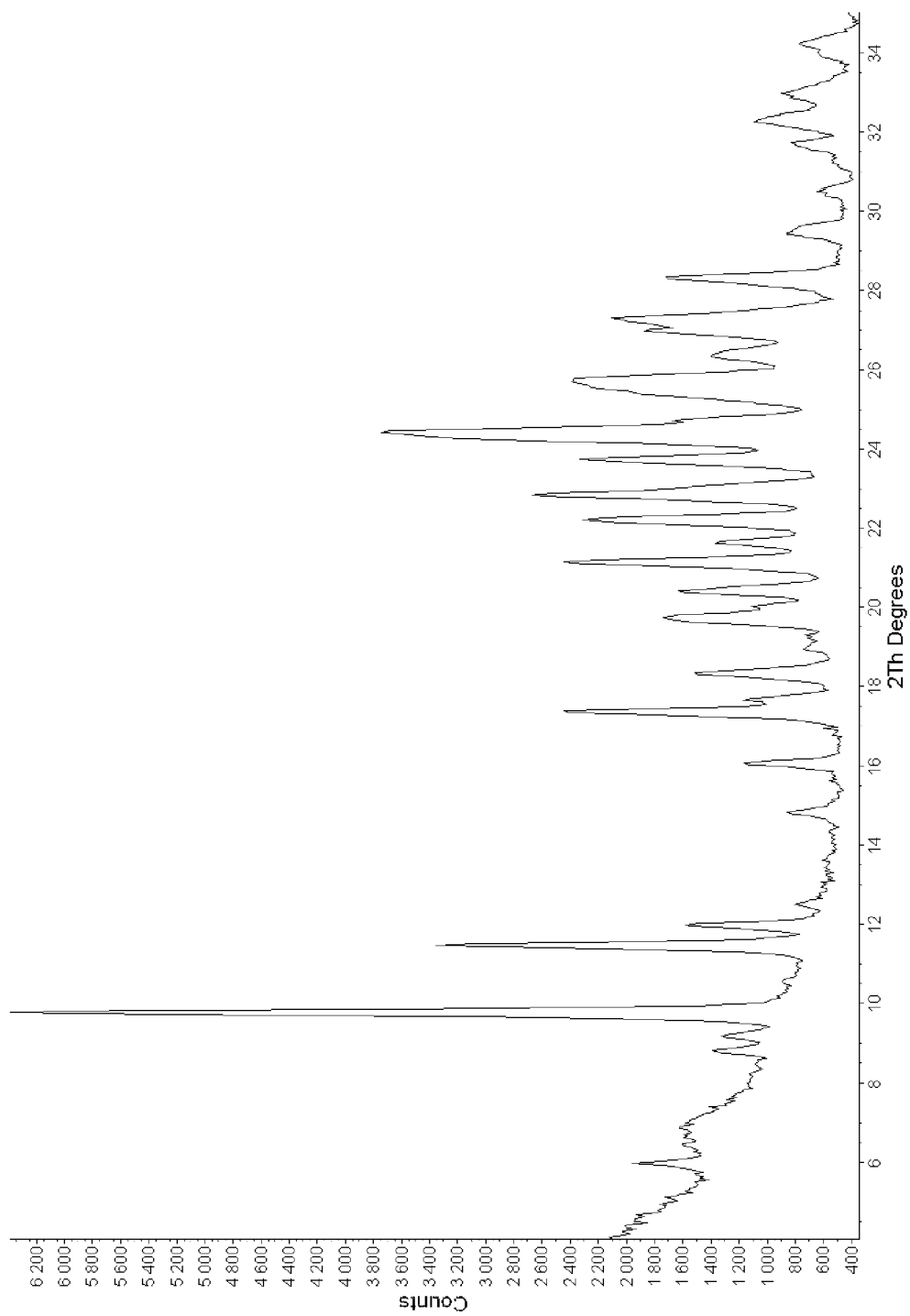
FIG. 7

A cyclic DSC (FIG. 6) was performed to investigate the nature of the endotherm at ca. 130° C. (±2° C.). Heating up to 200° C. was followed by fast cooling to room temperature (RT) (25° C.→200° C.→25° C.). The DSC thermogram upon cooling showed a small exotherm at ca. 97° C. (±2° C.), implying the reverse solid form transition to Form E1 (XRPD pattern FIG. 7). XRPD data of the solids showed no change of the solid form at 25° C., confirming that the exotherm upon cooling was the reverse solid transition. Variable temperature (VT) XRPD data (see Example 8a for VT XRPD experimental details) confirmed the above properties.

Example 5c: Experimental Thermal Analysis (Including DSC, TGA, TGA SDTA, TGA MS)

Melting properties were obtained from DSC thermograms, recorded with a heat flux DSC822e instrument (Mettler-Toledo GmbH, Switzerland). The DSC822e was calibrated for temperature and enthalpy with a small piece of indium (m.p. =156.6° C.; ΔHf=28.45 J.g$^{-1}$). Samples were sealed in standard 40 μL aluminium pans, pin-holed and heated in the DSC from 25° C. to 300° C., at a heating rate of 10° C./min. Dry N2 gas, at a flow rate of 50 mL/min was used to purge the DSC equipment during measurement.

Mass loss due to solvent or water loss from the crystals was determined by Thermo Gravimetric Analysis/Simultaneous Differential Temperature/Thermal Analysis (TGA/SDTA). Monitoring the sample weight, during heating in a TGA/SDTA851 instrument (Mettler-Toledo GmbH, Switzerland), resulted in a weight vs. temperature curve. The TGA/SDTA851 was calibrated for temperature with indium and aluminum. Samples were weighed into 100 µL aluminum crucibles and sealed. The seals were pin-holed and the crucibles heated in the TGA from 25 to 300° C. at a heating rate of 10° C./min. Dry N2 gas was used for purging.

The gases evolved from the TGA samples were analyzed by a mass spectrometer Omnistar GSD 301 T2 (Pfeiffer Vacuum GmbH, Germany). The latter is a quadrupole mass spectrometer which analyses masses in the range of 0-200amu.

Example 5d: Characterization by FTIR

FT-IR spectra were recorded using a Thermo Fischer Scientific FT-IR Nicolet 6700 spectrometer equipped with ATR probe.

Figure 8:
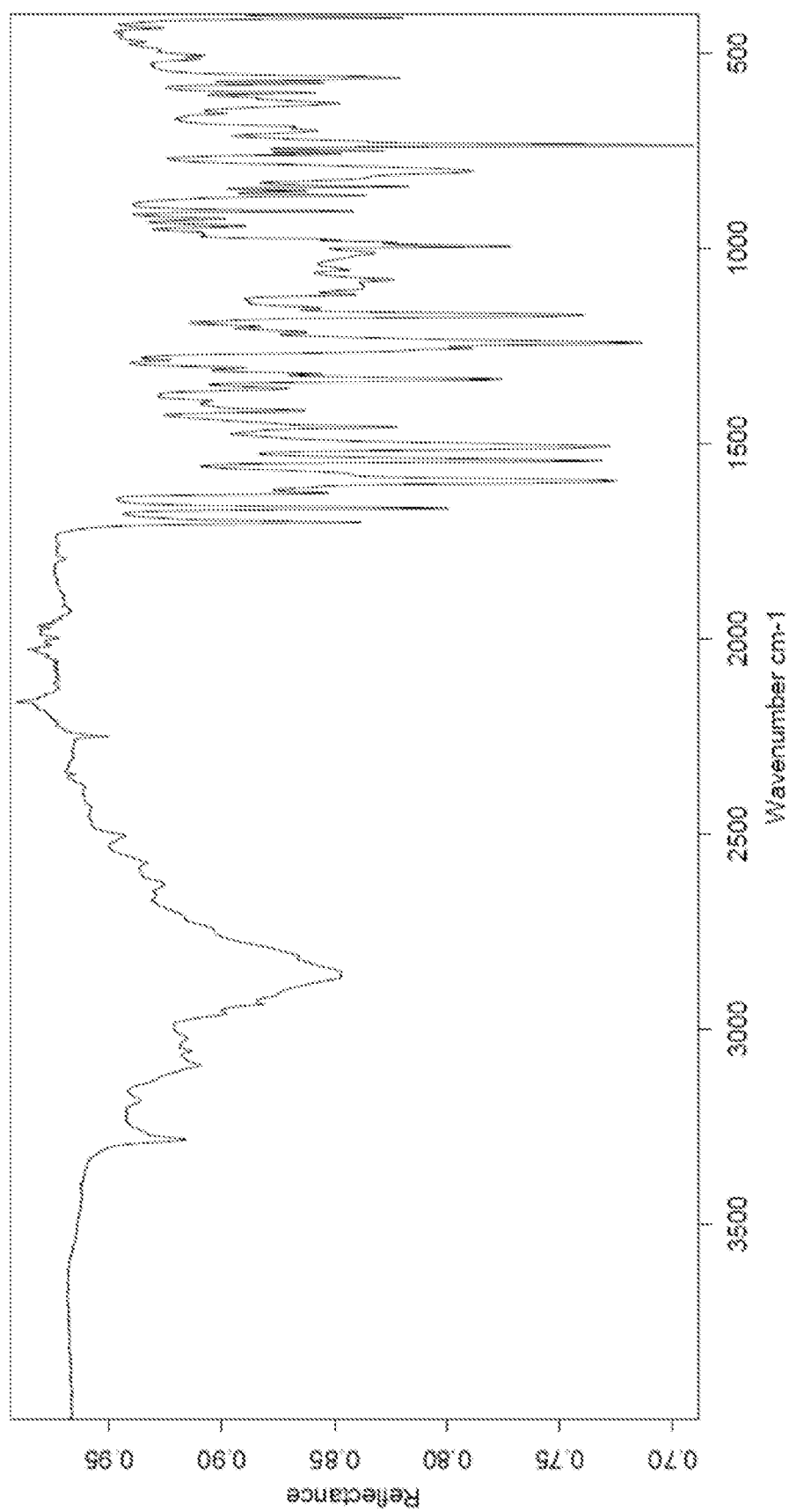
FIG. 8
Figure 9:
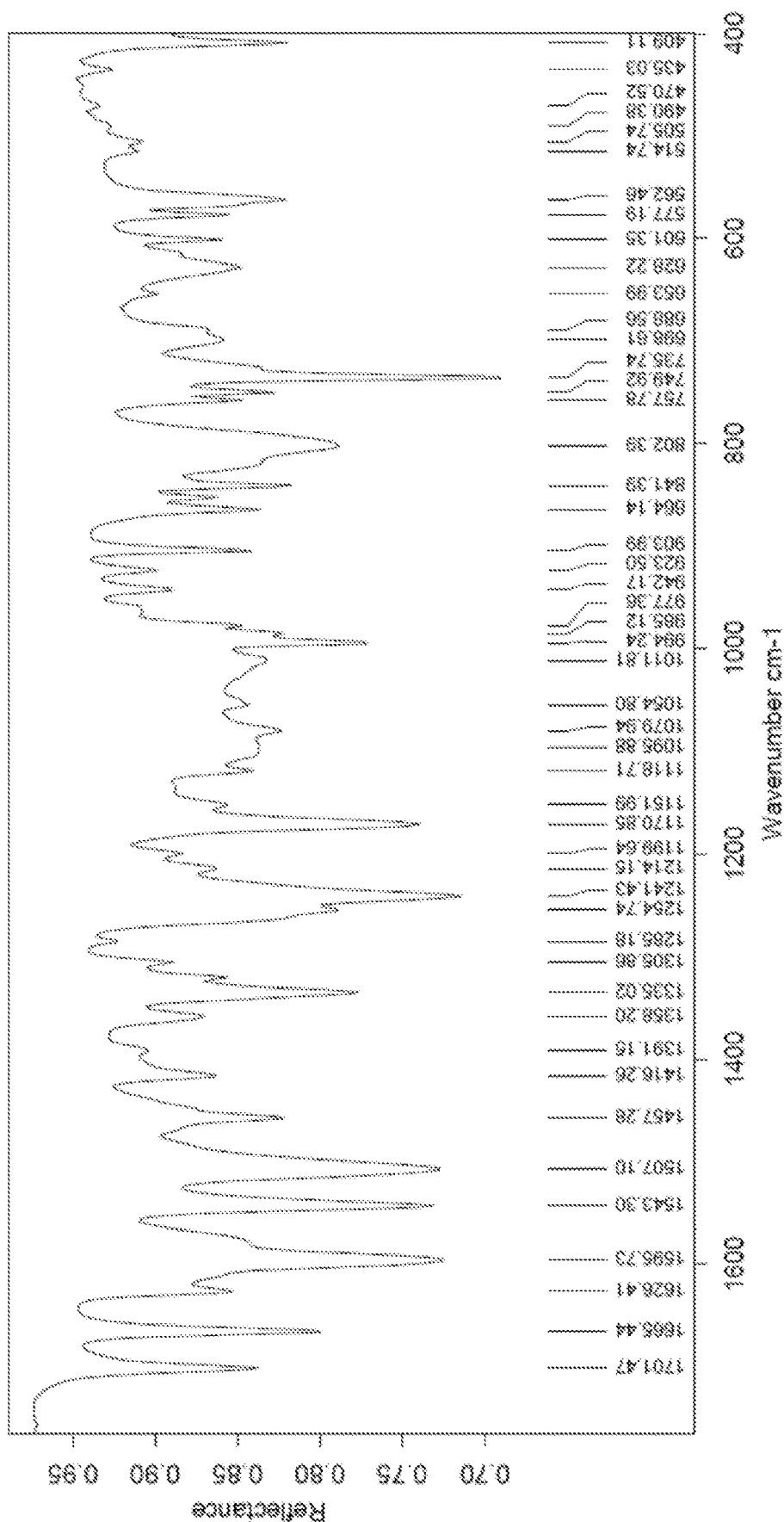
FIG. 9

The FTIR analysis confirmed the structure of the compound of formula I as detailed in Table 4 and depicted in FIG. 8 and in the zoom between ca. 1800 cm-1 and 400 cm-1 as FIG. 9. Characteristic IR vibrations of the crystalline form of the dichloride salt of the compound of formula I have been identified to be 1701, 1665, 1335, 1241, 1171, 942, 924, 864, 699, 628 cm-1 (±2 cm-1).

TABLE 4

Main IR vibrations of the crystalline form of the dichloride salt of the compound of formula I

| IR vibration (in cm-1) and its assignment according to literature [1] | | Observed vibration [cm$^{-1}$] |
|---|---|---|
| 3500-3100 | N—H (amide) stretching | 3282,3183,3093* |
| 3080-2840 | C—H (aromatic and aliphatic) stretching | 3093*, 3056, 3024, 2936 |
| 3000-2000 | NH$_3^+$ stretching | 2630, 2574, 2505 |
| 2260-2240 | CN stretching | 2250 |
| 1740-1630 | C═O stretching | 1701,1665 |
| 1630-1510 | N—H deformation and N—C═O stretching asymmetric | 1626*, 1596*, 1543*, 1507* |
| 1690-1520 | C═N stretching | 1626*, 1596*, 1543*, 1507* |
| 1625-1575 | C—C (aromatic) skeletal vibrations | 1626*, 1596* |
| 1525-1450 | | 1507*, 1457 |

*Several possible assignments.
[1] E. Pretsch, P. Bühlmann, M. Badertscher; Structure Determination of Organic Compounds, Tables of Spectral Data; Fourth, Revised and Enlarged Edition; Springer 2009.—Spectroscopic methods in organic chemistry Hesse, Meier and Zeeh 2$^{nd}$ Ed Thieme 2008 Stuttgart and New York.

Example 5e: Characterization by Solid State 13C {1 H} MAS-NMR

Magic angle spinning solid state carbon 13 nuclear magnetic resonance (13C {1H} MAS-NMR) (see FIG. 10) was performed on a Bruker Avance III 400 MHz solid-state NMR instrument equipped with a wide bore (89 mm room temperature bore) 9.4 Tesla magnet. A double resonance magic angle sample spinning (MAS) probe was used for a rotor size of 4.0 mm outer diameter. The probe was doubly tuned to the observe nucleus frequency-13C at 100.61 MHz in this study- and 1H at 400.13 MHz. The homogeneity of the magnetic field was set by shimming on an adamantane sample in a 4 mm ZrO$_2$ spinner, the 13C line width (full width at half maximum height) was less than 2 Hz. Chemical shift referencing was done by the substitution method using the 1H signal of tetramethylsilane (<1% v/v in CDCl$_3$) whose chemical shift was set to 0 ppm. This is the procedure recommended by the IUPAC. All measurements were performed with an additional flow of nitrogen gas (1200 L/h at 5° C.) blown laterally on the MAS spinner for temperature control. The true sample temperature was about 15° C. above this due to frictional heating in the MAS air bearings. For magic angle sample spinning the spinning frequency was set to 14 kHz. The number of scans was 1024, the recycle delay was 5 s, the contact time was 2 ms, the acquisition time was 33 ms, the processing parameters were tdeff=0 and 1b=5 Hz.

The carbon 13 chemical shifts for the investigated crystalline form of the dichloride salt of the compound of formula I are listed in Table 5. The atom numbers for the NMR assignment of the carbon 13 chemical shifts is depicted in FIG. 1.

TABLE 5

$^{13}$C{$^1$H} MAS-NMR shifts (±0.2 ppm for 13C chemical shifts) of Form E referenced by the substitution method using the $^1$H signal of tetramethylsilane (TMS <1% v/v in CDCl$_3$) whose chemical shift was set to 0 ppm. Also shown are the $^{13}$C{$^1$H} NMR shifts in liquid [D6]-DMSO referenced to [D6]-DMSO whose chemical shift was set to 39.52 ppm*.

| # | Group | $^{13}$C chemical shifts High resolution (liquid) in [D$_6$]-DMSO | $^{13}$C chemical shifts CP MAS 14 kHz |
|---|---|---|---|
| 1 | N | — | — |
| 2 | C | 140.9 | 137.4 [a] |

TABLE 5-continued $^{13}$C{$^1$H} MAS-NMR shifts (±0.2 ppm for 13C chemical shifts) of Form E referenced by the substitution method using the $^1$H signal of tetramethylsilane (TMS <1% v/v in CDCl$_3$) whose chemical shift was set to 0 ppm. Also shown are the $^{13}$C{$^1$H} NMR shifts in liquid [D6]-DMSO referenced to [D6]-DMSO whose chemical shift was set to 39.52 ppm*.

| # | Group | $^{13}$C chemical shifts High resolution (liquid) in [D$_6$]-DMSO | $^{13}$C chemical shifts CP MAS 14 kHz |
|---|---|---|---|
| 3 | N | — | — |
| 4 | C | 141.5 | 141.4 [a] |

TABLE 5-continued $^{13}C\{^1H\}$ MAS-NMR shifts (±0.2 ppm for 13C chemical shifts) of Form E referenced by the substitution method using the $^1H$ signal of tetramethylsilane (TMS <1% v/v in $CDCl_3$) whose chemical shift was set to 0 ppm. Also shown are the $^{13}C\{^1H\}$ NMR shifts in liquid [D6]-DMSO referenced to [D6]-DMSO whose chemical shift was set to 39.52 ppm*.

| # | Group | $^{13}$C chemical shifts High resolution (liquid) in [D$_6$]-DMSO | $^{13}$C chemical shifts CP MAS 14 kHz |
|---|---|---|---|
| 5 | CH ar | 119.9 | 118.8 [b] |
| 6 | CH ar | 123.3 | 121.8 [b] |
| 7 | CH ar | 124.8 | 124.2 [b] |
| 8 | CH ar | 111.2 | 109.5 |
| 9 | C ar | 136.1 | 134.8 [a] |
| 10 | C | 137.7 | 137.4 [a] |
| 11 | N | — | — |
| 13 | N | — | — |
| 14 | C | 155.8 | 156.2 |
| 15 | NH | — | — |
| 16 | CH$_2$ | 40.1 | 40.3 |
| 17 | CH$_2$ | 16.7 | 19.0 |
| 18 | CN | 119.1 | 119.6 |
| 19 | CN | — | — |
| 20 | CH2 | 51.8 | 49.1 |
| 21 | C=O | 191.3 | 196.2 |
| 22 | C ar | 129.6 | 128.1 |
| 23 | CH ar | 129.6 | 131.2 [c] |
| 24 | CH ar | 119.0 | 121.2 |
| 25 | C ar | 143.6 | 144.0 [a] |
| 26 | CH ar | 119.0 | 121.2 |
| 27 | CH ar | 129.6 | 128.9 [c] |
| 28 | NH | — | — |
| 29 | C=O | 168.3 | 167.1 |
| 30 | CH | 52.7 | 55.2 |
| 31 | CH$_2$ | 30.3 | 34.6 [d] |
| 32 | CH$_2$ | 21.1 | 25.0 [d] |
| 33 | CH$_2$ | 26.2 | 26.6 [d] |
| 34 | CH$_2$ | 38.1 | 39.5 |
| 35 | NH$_3^+$ | — | — |
| 36 | NH$_3^+$ | — | — |

[a], [b], [c], [d] Signals with the same superscript might be exchanged.
*H. E. Gottlieb, V. Kotlyar, A. Nudelman J. Org. Chem, Vol 62, 1997, 7512-7515

Example 5f: Characterization by DVS

Differences in hygroscopicity of the various forms of a solid material provided a measure of their relative stability at increasing relative humidity. Moisture sorption isotherms were obtained using a DVS-1 system from Surface Measurement Systems (London, UK). The relative humidity was varied during sorption-desorption (see specific experiment) at a constant temperature of ca. 25° C. At the end of the DVS experiment the sample was measured by XRPD.

Figure 11:
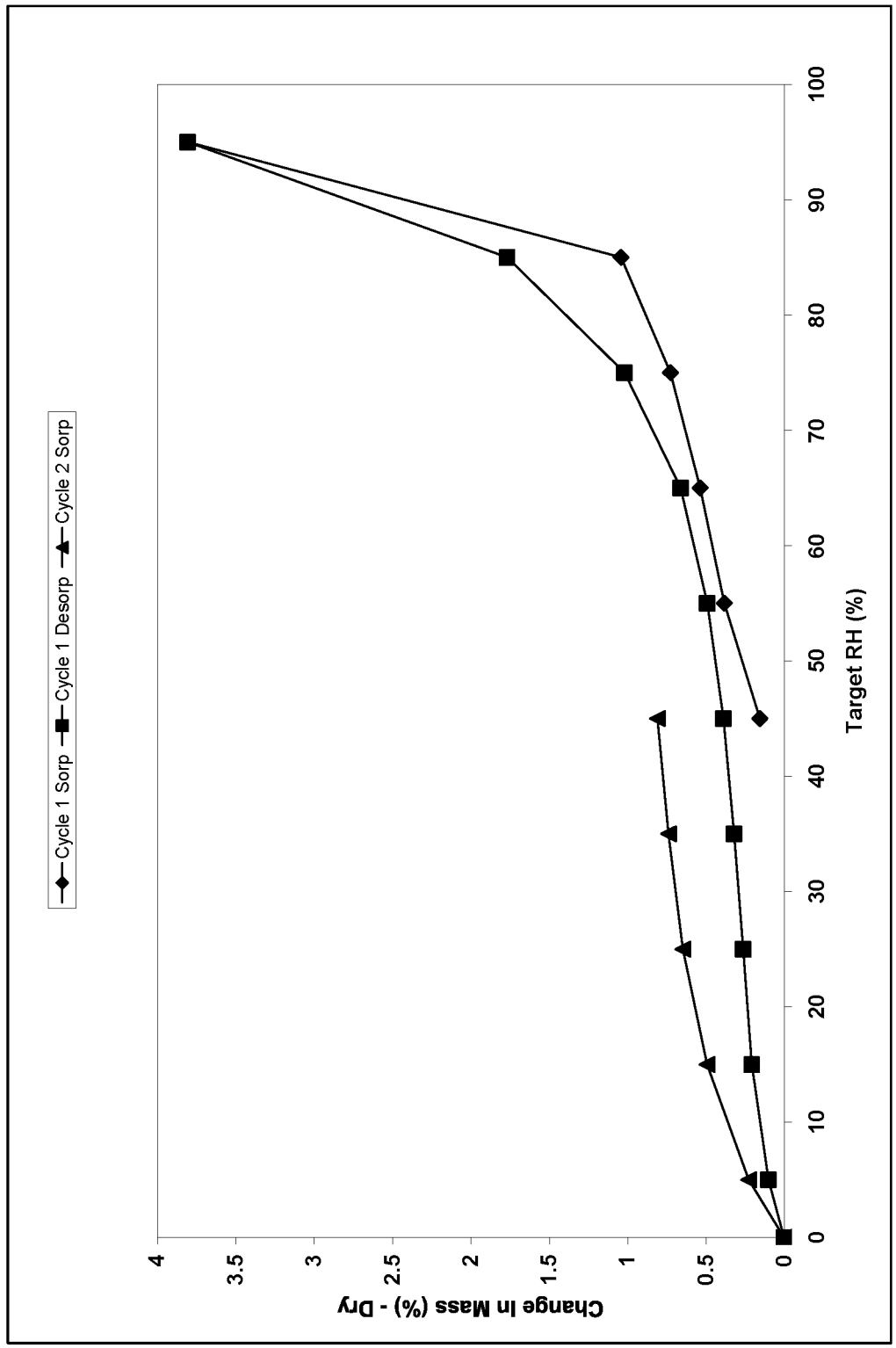
FIG. 11

The dynamic vapor sorption (DVS) analysis for the crystalline Form E of the dichloride salt of the compound of formula I is depicted in FIG. 11. It shows a 1% water absorption for the compound up to 85% RH and ca. 4% water absorption up to 95% RH.

Example 5g: Solubility

The thermodynamic pH-dependent solubility was performed in unbuffered water as well as using standard Merck Titriplex® buffers (Merck Titrisol® buffer pH 3 with citrate and HCl; Merck Titrisol® buffer pH 4 with citrate and HCl; Merck Titrisol® buffer pH 5 with citrate and NaOH; Merck Titrisol® buffer pH 6 with citrate and NaOH; Merck Titrisol® buffer pH 7 with phosphate; for buffering at pH 4.5 a 50/50 mixture of buffers for pH 4 and 5 was used; for buffering at pH 5.5 a 50/50 mixture of buffers for pH 5 and 6 was used).

For each experiment, an 8 mL screw cap vial was prepared with the polymorphic material, the buffer solvent according to the target pH and a magnetic stirring bar. Each pH data point was determined in triplicate with a target pH of 3, 4, 4.5, 5, 5.5 and 7. The pH was measured (Fisherbrand pH meter Hydrus 400, a three point calibration was performed prior to measurement) and adjusted with 1M NaOH solution. The mixtures were left to equilibrate for 24 h at room temperature while stirring. After 24 h the pH was monitored and the slurries were centrifuged for 10 min at 3000 rpm to separate the solids and liquids and filtered (0.45 micron disk filter). If necessary, the isolated filtrates were diluted in the sample solvent to fall within the calibration curve of the HPLC testing. Concentrations of the compound of formula I were determined by High Performance Liquid Chromatography with Diode Array Detection analysis (HPLC-DAD). The calibration curves were obtained from two independently prepared stock solutions of the compound of formula I in a sample solution of water/THF/TFA (50/50/0.05 v/v/v).

HPLC testing was performed on Agilent 1100 with DAD detector at 280 nm wavelength. A LOQ of 11 μg/mL was determined, linearity is given up to ca. 0.7 mg/mL. Each sample was diluted to ca. 0.5 mg/mL or measured as neat if the concentration was below or equal ca. 0.5 mg/mL.

Example 6-Preparation of the Crystalline Dichloride Salt (A+M) of the Compound of Formula I Example 6a: Crude Dichloride Salt of the Compound of Formula I 111.6 g (156 mmol) of the compound of formula II ($R^3$ is tert-butyl) prepared according to the procedure provided in Example 2 was suspended in 738 mL of THF and heated to ca. 33° C. 160 g of 30% aqueous HCl was added and the mixture was stirred for ca. 18 h. The mixture was cooled to ca. 10° C. and 738 mL of THF was added. The suspension was filtered, the cake washed with 120 mL of THF and dried at ca. 40° C. under vacuum, providing 90 g of compound of formula I.

Example 6b: Purification and Crystallization

Crude compound of formula I (2.6 kg) was dissolved in water (2.7 L) and tetrahydrofuran (5.5 L) at ca. 40-50° C. Tetrahydrofuran (90 L) was slowly added at ca. 40-50° C. The resulting suspension was stirred, then cooled to ca. 10° C. and further stirred. The suspension was filtered, the cake was washed with THF and dried. The resulting solid (2.4 kg) was dissolved in 7.3 L water, the solution was filtered and the filter was washed with 2.3 L of water. The filtered solution and wash were evaporated to dryness at ca. 30° C. under reduced pressure. The residue was further dried at 50° C. under reduced pressure, providing 2.2 kg of compound of formula I as Mixture A1+M1.

Figure 14:
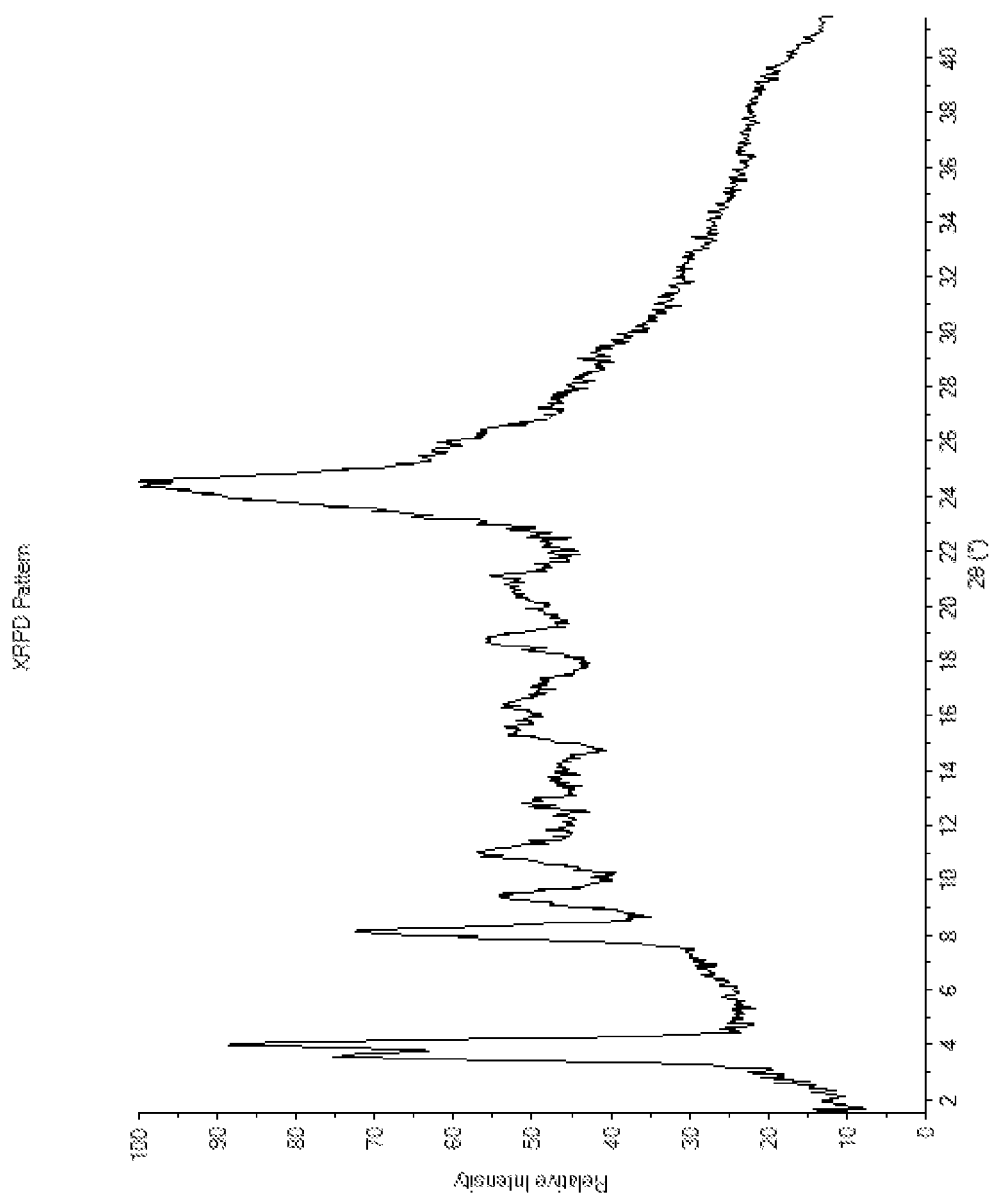
FIG. 14
Figure 15:
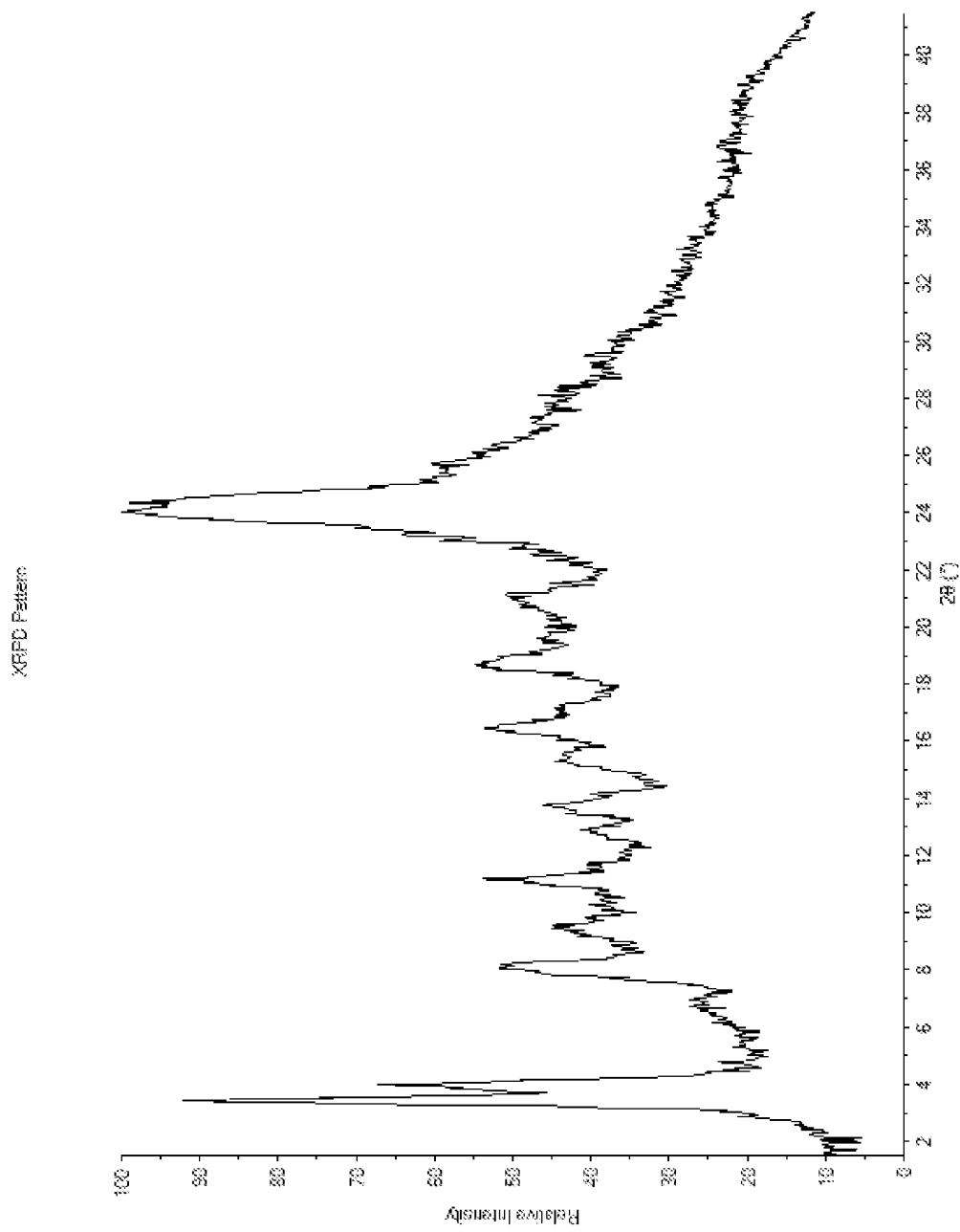
FIG. 15
Figure 19:
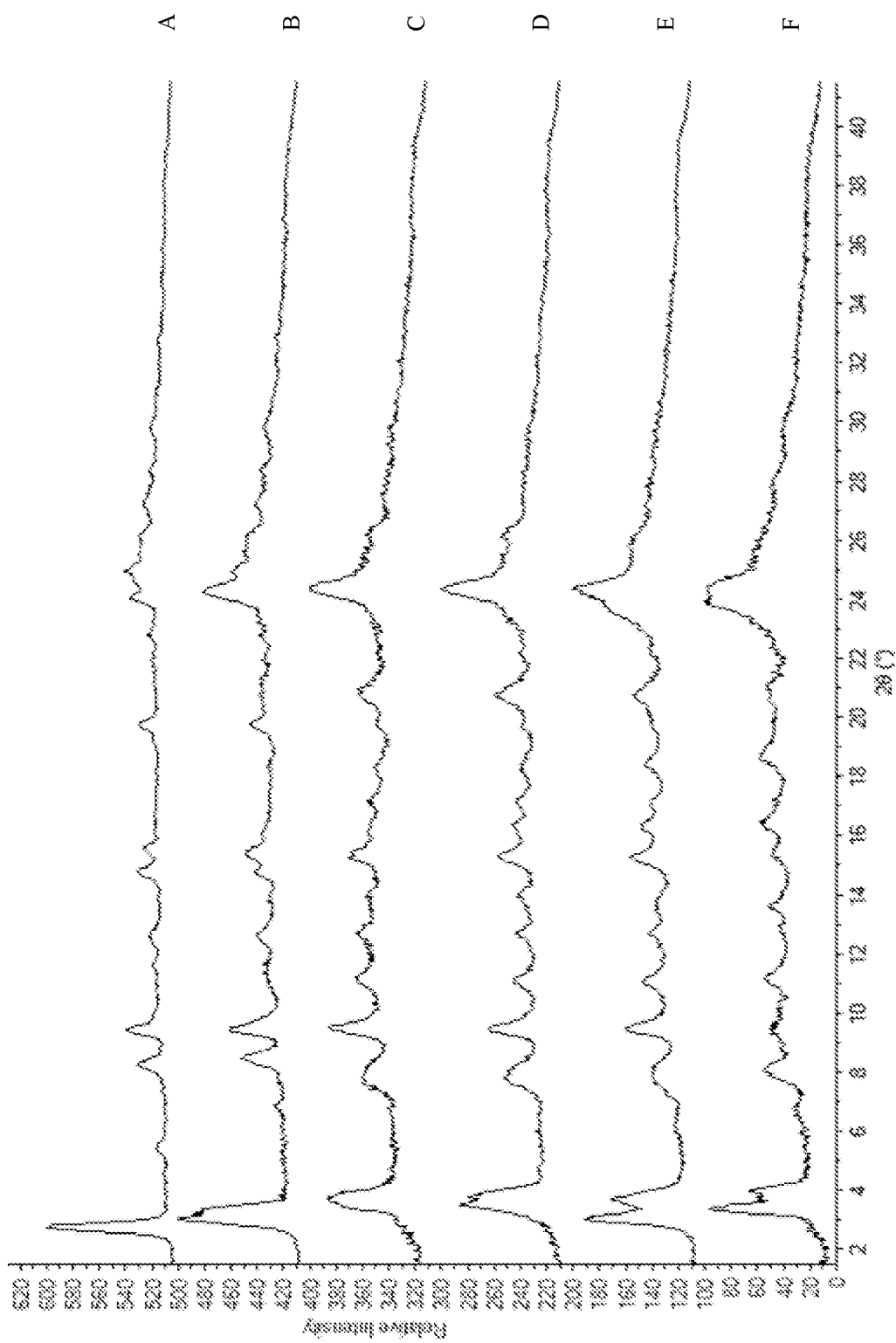
FIG. 19
Figure 24:
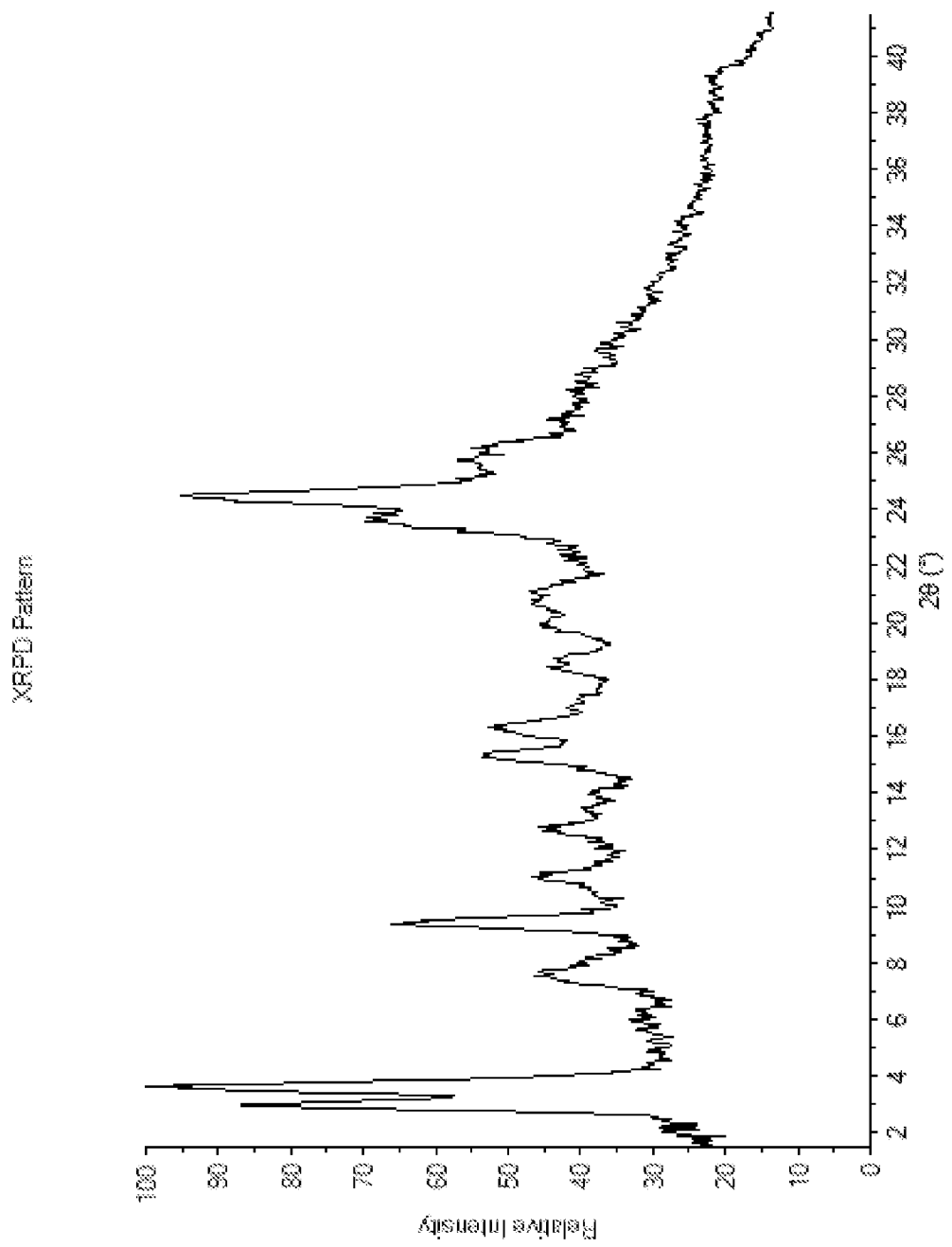
FIG. 24
Figure 26:
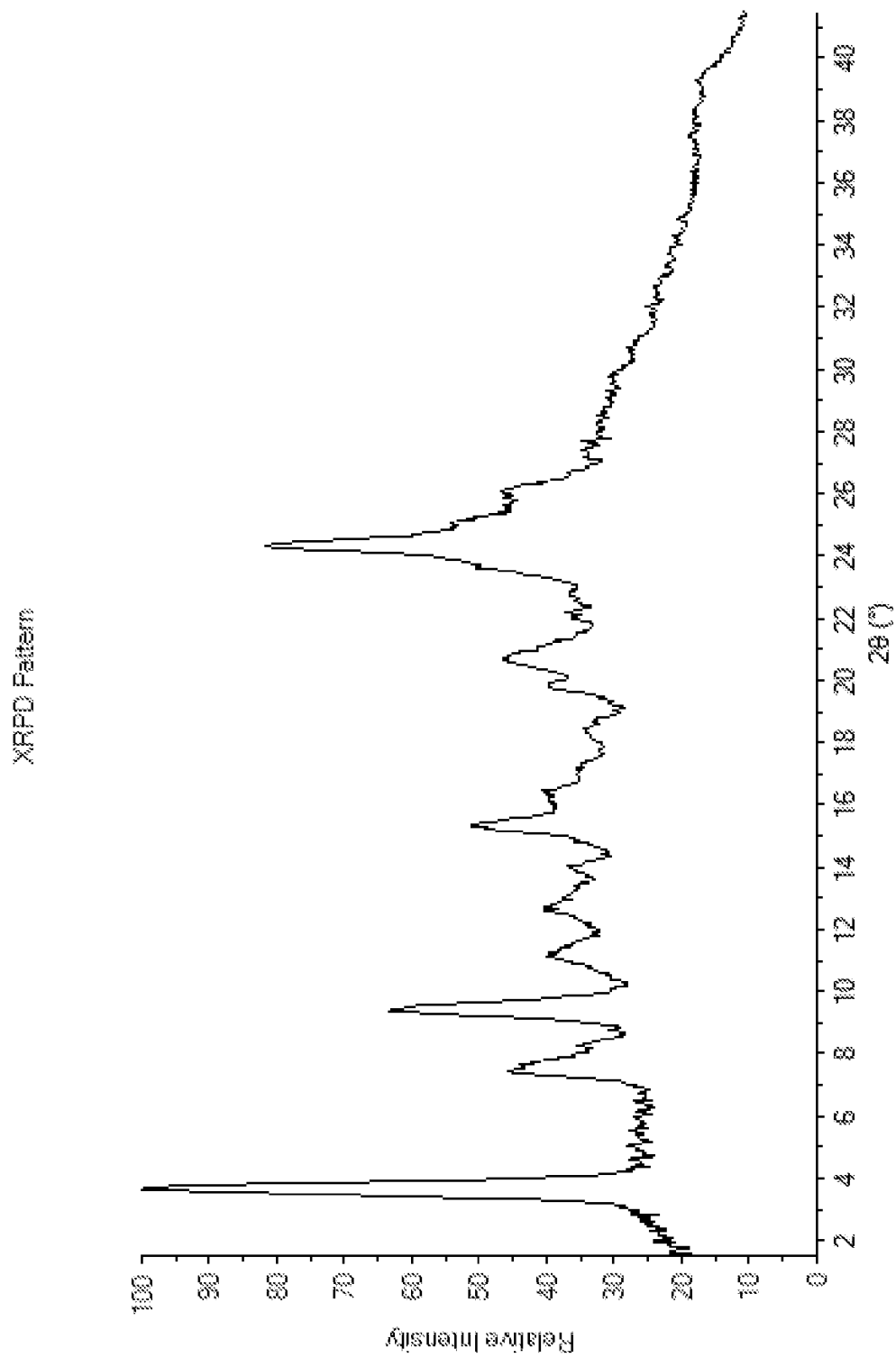
FIG. 26

Typically the starting point for generation of other crystal forms within System A+M was Mixture A1+M1 (FIG. 14) and Mixture A1+M4 (FIG. 15). FIG. 19 gives an overlay of XRPD patterns that were observed when Mixture A1+M4 was exposed to climate chamber conditions. Mixture M3+M5 (FIG. 24) was observed after 1 week and also after 2.5 weeks at 40° C./75% RH. Form M5 was observed after 4 weeks of treating Mixture A1+M4 at 40° C./75% RH (FIG. 26). After 4 weeks at 40° C./75% RH and 2 days 25° C./95%

Figure 17:
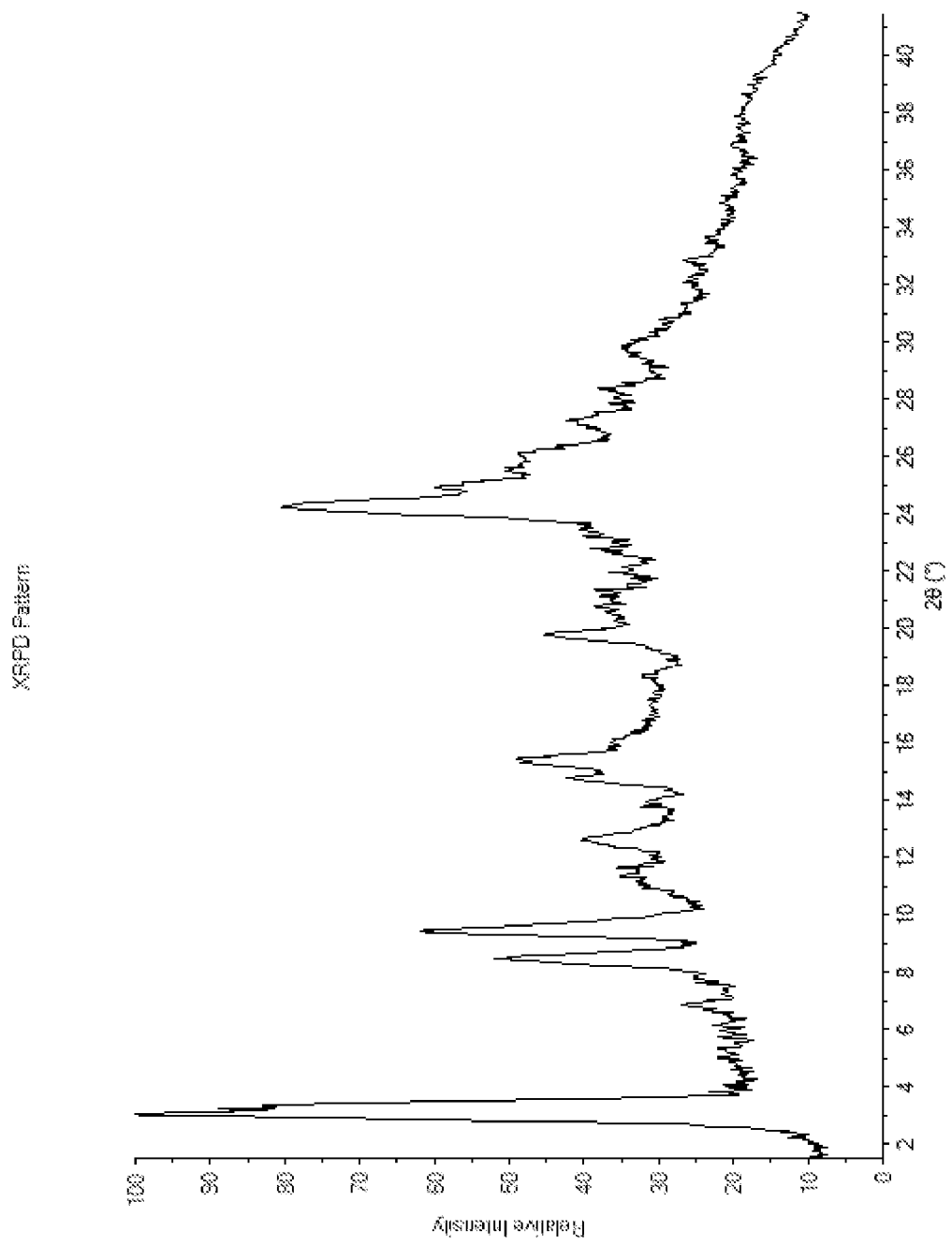
FIG. 17
Figure 18:
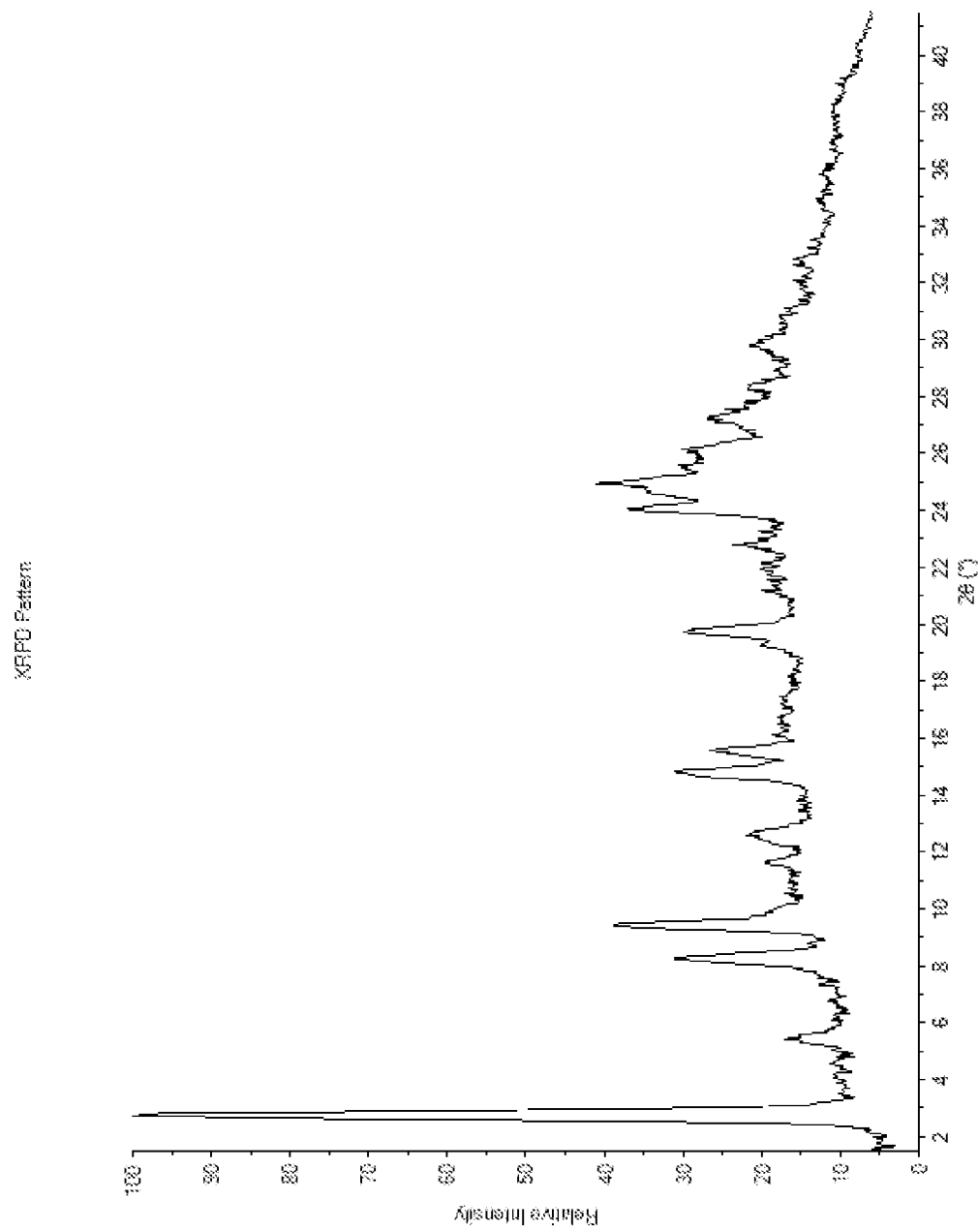
FIG. 18

RH Mixture A2+M4 was obtained (FIG. 17). After 4 weeks at 40° C./75% RH and 1 week at 25° C./95% RH Mixture A2+M11 was obtained (FIG. 18).

Example 7-Preparation of Specific Forms of the Crystalline Dichloride Salt within System A+M of the Compound of Formula I Preparation of Form A0

Example 7a

Figure 12:
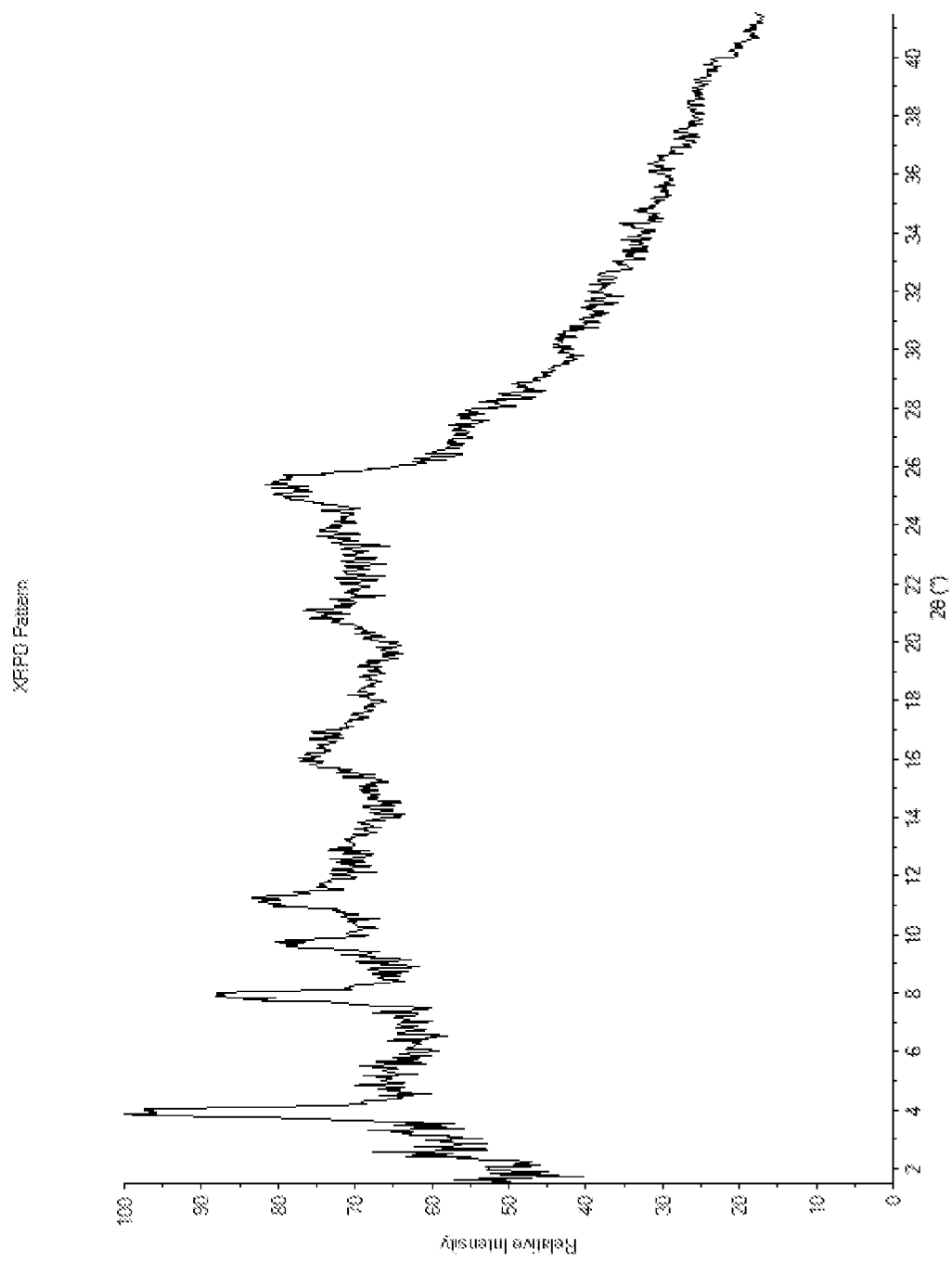
FIG. 12

Form A0 (FIG. 12, Table 6) was obtained by heating Mixture A1+M1 for 2.5 h to 195° C.

Example 7b

Form A0 was obtained by heating Form M1 for 4 h to 195° C.

Preparation of Form A1

Example 7c

Figure 13:
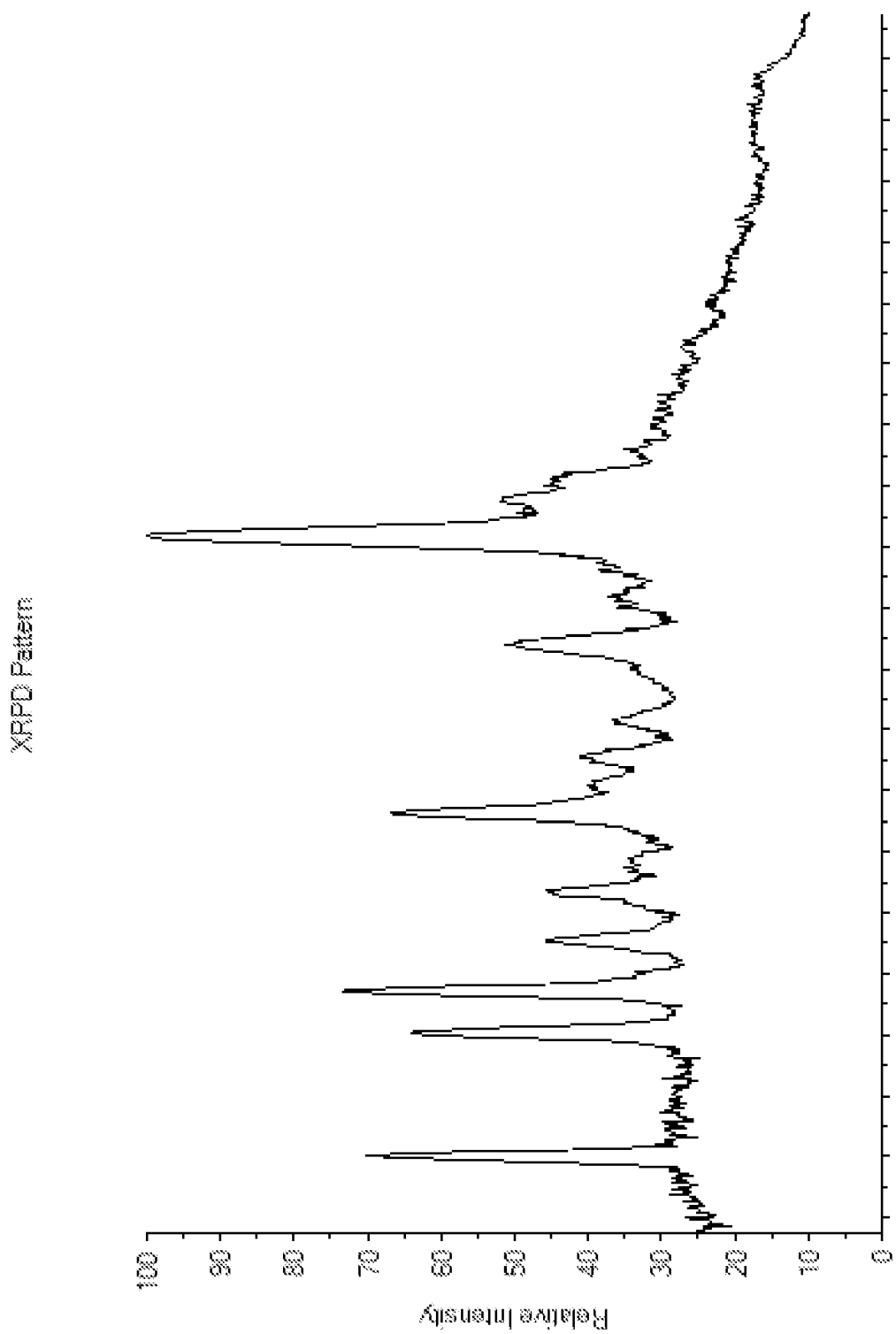
FIG. 13

Form A1 (FIG. 13, Table 7) was obtained by allowing form A0 to stand at ambient conditions for ca. 11 days.

Example 7d

Form A1 was obtained by cooling crystallization of Mixture A1+M1 in the following solvent systems: water and methanol/water (50:50). 80 µL of the respective solvent were added to ca. 4 mg of Mixture A1+M1. The temperature was increased to 60° C. and was kept for 60 min at 60° C. After cooling to 20° C. with a cooling rate of 20° C./min, the mixture was allowed to remain at 20° C. under stirring for 24 h. Form F was obtained by solvent evaporation under vacuum (5 mbar). Form F was exposed to climate chamber conditions of 40° C./75% RH for 67 h resulting in Form A1.

Example 7e

Form A1 was obtained by cooling crystallization of Mixture A1+M1 in methanol. 80 µL of the methanol were added to ca. 4 mg of Mixture A1+M1. The temperature was increased to 60° C. and was kept for 60 min at 60° C. After cooling to 2° C. with a cooling rate of 20° C./min, the mixture was allowed to remain at 2° C. under stirring for 24 h. Form F was obtained by solvent evaporation under vacuum (5 mbar). Form F was exposed to climate chamber conditions of 40° C./75% RH for 67 h resulting in Form A1.

Preparation of Mixture A1+M1

The XRPD diffractogram is depicted in FIG. 14 and Table 19.

Example 7f 23.2 mg of the compound of formula I mixture A1+M4 were added in 0.60 mL of diethyl ether resulting in a slurry which was stirred at 20° C. for two weeks. Afterwards the sample was centrifuged, the liquid separated by filtration and the solid part was dried under vacuum (5 mbar). The solid was analyzed and found to be Mixture A1+M1.

Example 7g 22.7 mg of the compound of formula I mixture A1+M4 were added in 0.60 mL of tert-butyl methyl ether resulting in a slurry which was stirred at 20° C. for two weeks. Afterwards the sample was centrifuged, the liquid separated by filtration and the solid part was dried under vacuum (5 mbar). The solid was analyzed and found to be Mixture A1+M1.

Preparation of Mixture A1+M4

The XRPD diffractorgam is depicted in FIG. 15 and Table 20.

Example 7h

Mixture A1+M4 was formed by exposing 20 mg Mixture A1+M1 for at least 3 min to 40% RH.

Example 7i 23.2 mg of the Mixture A1+M1 were slurried in 0.60 mL of diethyl ether at 20° C. for two weeks. The resulting wet solid was separated by centrifugation and filtration and was analyzed and found to be Mixture A1+M4.

Example 7j 22.7 mg of the Mixture A1+M1 were slurried in 0.60 mL of tert-butyl methyl ether at 20° C. for two weeks. The resulting wet solid was separated by centrifugation and filtration and was analyzed and found to be Mixture A1+M4.

Example 7k 24.2 mg of the Mixture A1+M1 were slurried in 0.60 mL of n-heptane at 20° C. for two weeks. The resulting wet solid was separated by centrifugation and filtration and was analyzed and found to be Mixture A1+M4.

Example 7l 18.9 mg of the Mixture A1+M1 were slurried in 0.60 mL of toluene at 20° C. for two weeks. The resulting wet solid was separated by centrifugation and filtration and was analyzed and found to be Mixture A1+M4.

Example 7m 18.9 mg of the Mixture A1+M1 were slurried in 0.40 mL of diisopropylether at 50° C. for two weeks. The resulting wet solid was separated by centrifugation and filtration and was analyzed and found to be Mixture A1+M4.

Example 7n 22.8 mg of the Mixture A1+M1 were slurried in 0.40 mL of n heptane at 50° C. for two weeks. The resulting wet solid was separated by centrifugation and filtration and was analyzed and found to be Mixture A1+M4.

Example 7o 24.9 mg of the Mixture A1+M1 were slurried in 0.40 mL of toluene at 50° C. for two weeks. The resulting wet solid was separated by centrifugation and filtration and was analyzed and found to be Mixture A1+M4.

Preparation of Mixture A1+M4+M5

Example 7p

Mixture A1+M4+M5 was formed by exposing Mixture A1+M4 for ca. 3 min to 60% to 80% RH.

Preparation of Mixture A2+M4
The XRPD diffractogram is depicted in FIG. 17 and Table 21.

Example 7q

Figure 16:
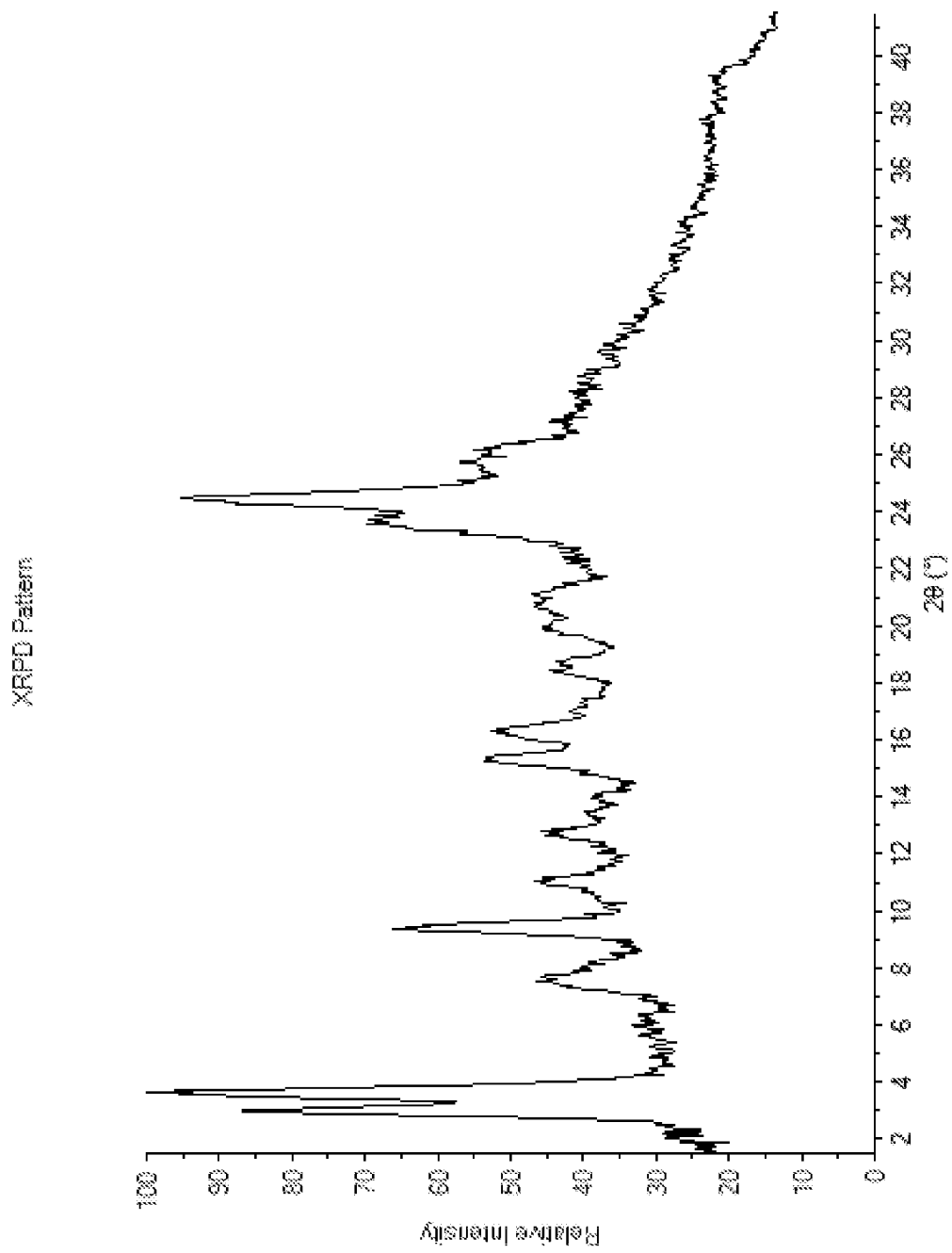
FIG. 16

After storing Mixture A1+M4 for 4 weeks at 40° C./75% RH and 2 days at 25° C./95% RH Mixture A2+M4 was obtained.
Preparation of Mixture M3+M5
The XRPD diffractogram is depicted in FIG. 16 and Table 11.

Example 7r

Mixture M3+M5 is observed after storing Mixture A1+M4 for between 1 week and 2.5 weeks at 40° C./75% RH.
Preparation of Mixture A2+M11
The XRPD diffractogram is depicted in FIG. 18 and Table 22.

Example 7s

Figure 20:
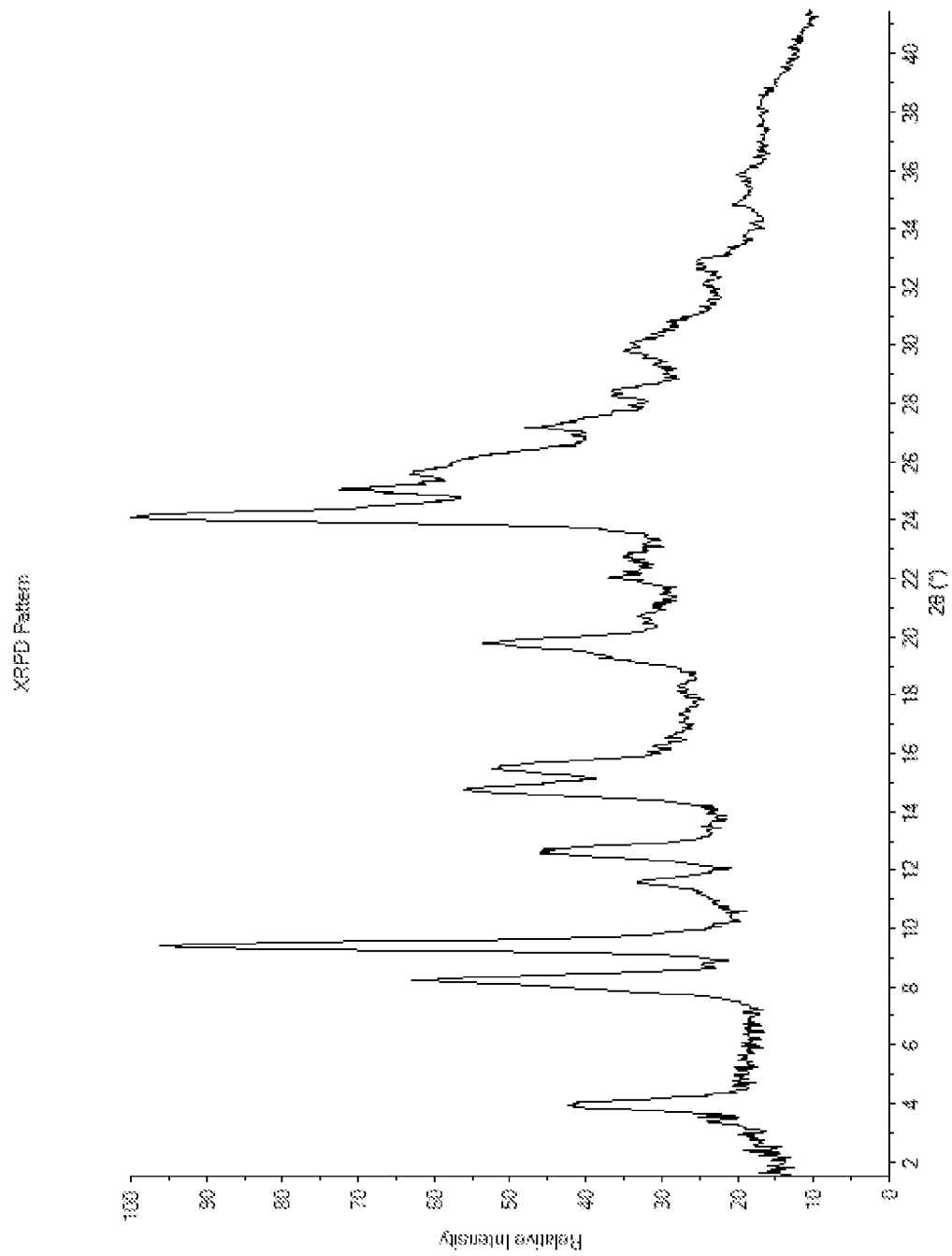
FIG. 20
Figure 21:
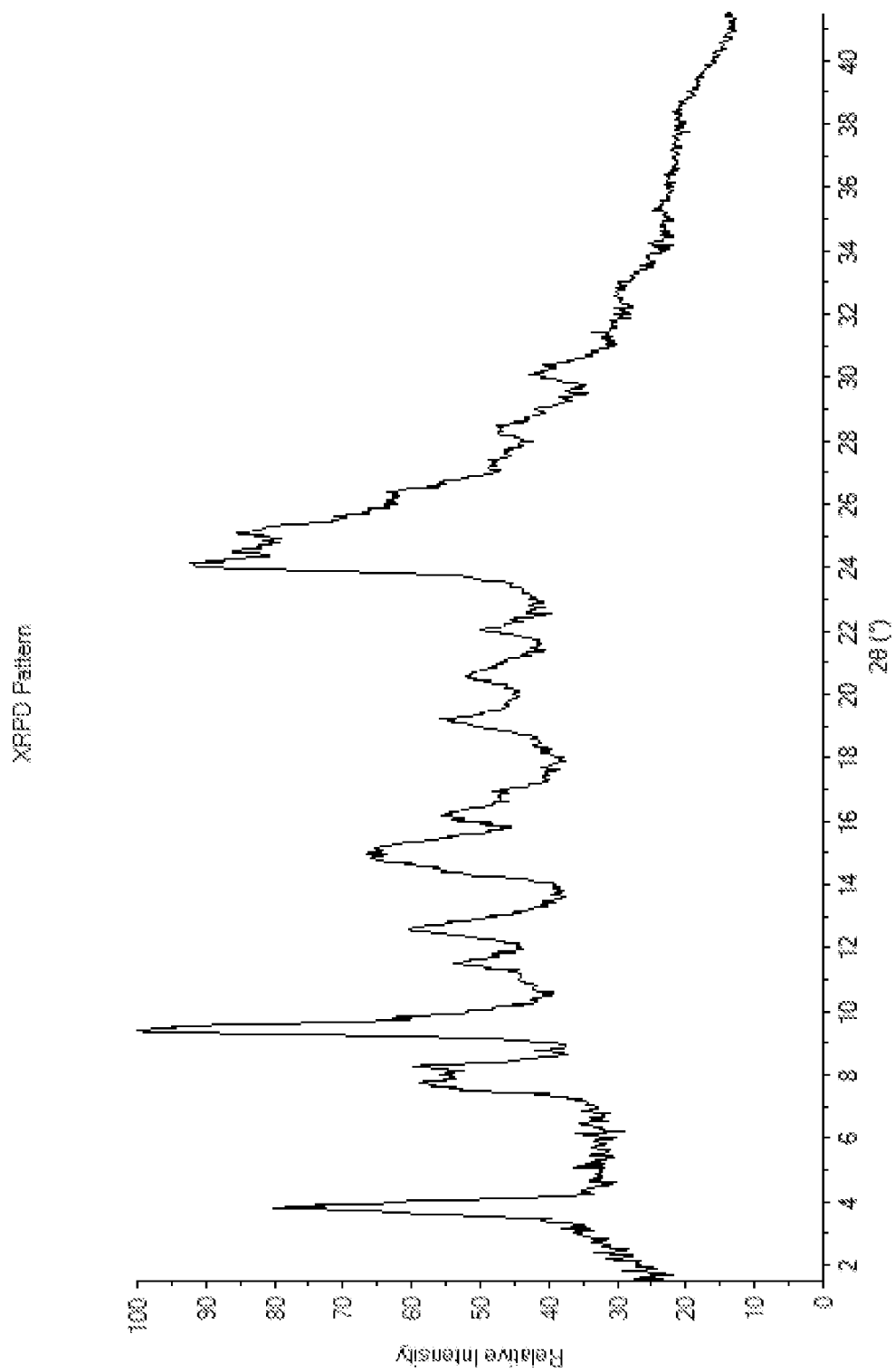
FIG. 21

Mixture A2+M11 was obtained after storage of Mixture A1+M4 for 4 weeks at 40° C. 75% RH and 1 week at 25° C./95% RH (FIG. 19).
Preparation of Form A2
The XRPD diffractogram is depicted in FIG. 20 and Table 20.

Example 7t

Form A2 was obtained by cooling crystallization of Mixture A1+M1 in all of the following different solvent systems: 1,4-dioxane/water (50:50), isopropanol/water (50:50), acetonitrile/water (50:50), ethanol/water (50:50), isopropanol, and acetone/water (50:50). 80 µL of the respective solvent were added to ca. 4 mg of Mixture A1+M1. The temperature was increased to 60° C. and was kept for 60 min at 60° C. After cooling to 20° C. with a cooling rate of 20° C./min, the mixture was allowed to remain at 20° C. under stirring for 24 h. Form F was obtained by solvent evaporation under vacuum (5 mbar). Form F was exposed to climate chamber conditions of 40° C./75% RH for 67 h resulting in Form A2.

Example 7u

Figure 22:
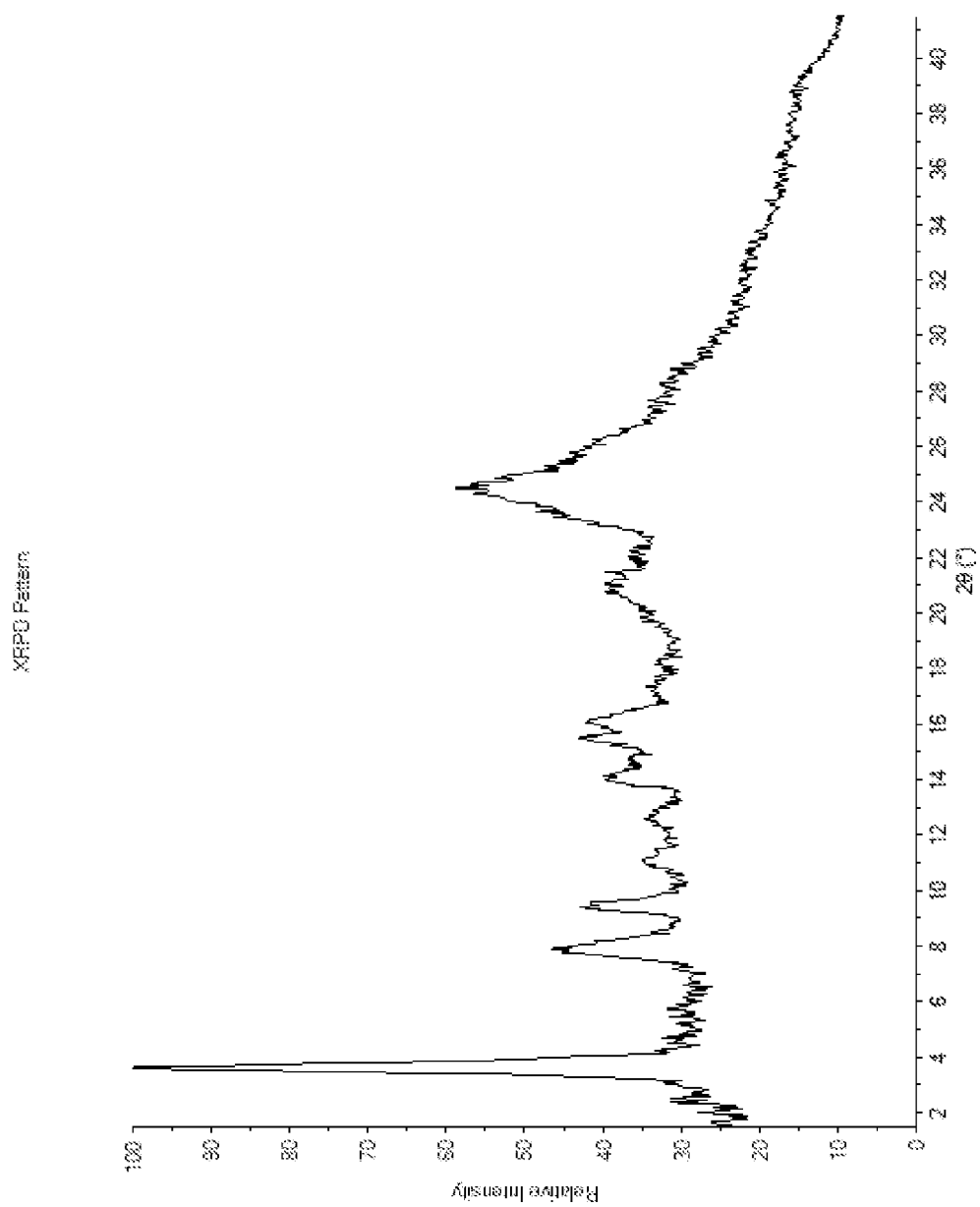
FIG. 22

Form A2 was obtained by cooling crystallization of Mixture A1+M1 in the following solvent systems: Methanol and ethanol. 80 µL of the respective solvent were added to ca. 4 mg of Mixture A1+M1. The temperature was increased to 60° C. and was kept for 60 min at 60° C. After cooling to 20° C. with a cooling rate of 20° C./min, the mixture was allowed to remain at 20° C. under stirring for 24 h. Form G was obtained by solvent evaporation under vacuum (5 mbar). Form G was exposed to climate chamber conditions of 40° C./75% RH for 67 h resulting in Form A2.
Preparation of Form M1
The XRPD diffractogram is depicted in FIG. 22 and Table 9.

Example 7v

Form M1 was obtained by cooling crystallization of Mixture A1+M1 in all of the following different solvent systems: water, 1,4-dioxane/water (50:50), ethyl acetate/dimethylsulfoxide (50:50), isopropanol/water (50:50), acetonitrile/water (50:50), ethanol/water (50:50), and tetrahydrofuran/water (50:50). 80 µL of the respective solvent were added to ca. 4 mg of Mixture A1+M1. The temperature was increased to 60° C. and was kept for 60 min at 60° C. After cooling to 2° C. with a cooling rate of 2° C./min, the mixture was allowed to remain at 2° C. under stirring for 24 h. Form F was obtained by solvent evaporation under vacuum (5 mbar). Form F was exposed to climate chamber conditions of 40° C./75% RH for 67 h resulting in Form M1.

Example 7w

Form M1 was obtained by cooling crystallization of Mixture A1+M1 in the following different solvent systems: p-xylene/methanol (50:50) and 2-butanone/methanol (50:50). 80 µL of the respective solvent were added to ca. 4 mg of Mixture A1+M1. The temperature was increased to 60° C. and was kept for 60 min at 60° C. After cooling to 2° C. with a cooling rate of 2° C./min, the mixture was allowed to remain at 2° C. under stirring for 24 h. Form G was obtained by solvent evaporation under vacuum (5 mbar). Form G was exposed to climate chamber conditions of 40° C./75% RH for 67 h resulting in Form M1.

Example 7x

Form M1 was obtained by cooling crystallization of Mixture A1+M1 in the following different solvent systems: tetrahydrofuran/methanol (50:50) and 2 tetrahydrofuran/ethyl acetate (50:50). 80 µL of the respective solvent were added to ca. 4 mg of Mixture A1+M1. The temperature was increased to 60° C. and was kept for 60 min at 60° C. After cooling to 20° C. with a cooling rate of 20° C./min, the mixture was allowed to remain at 20° C. under stirring for 24 h. Form G was obtained by solvent evaporation under vacuum (5 mbar). Form G was exposed to climate chamber conditions of 40° C./75% RH for 67 h resulting in Form M1.

Example 7y

Figure 23:
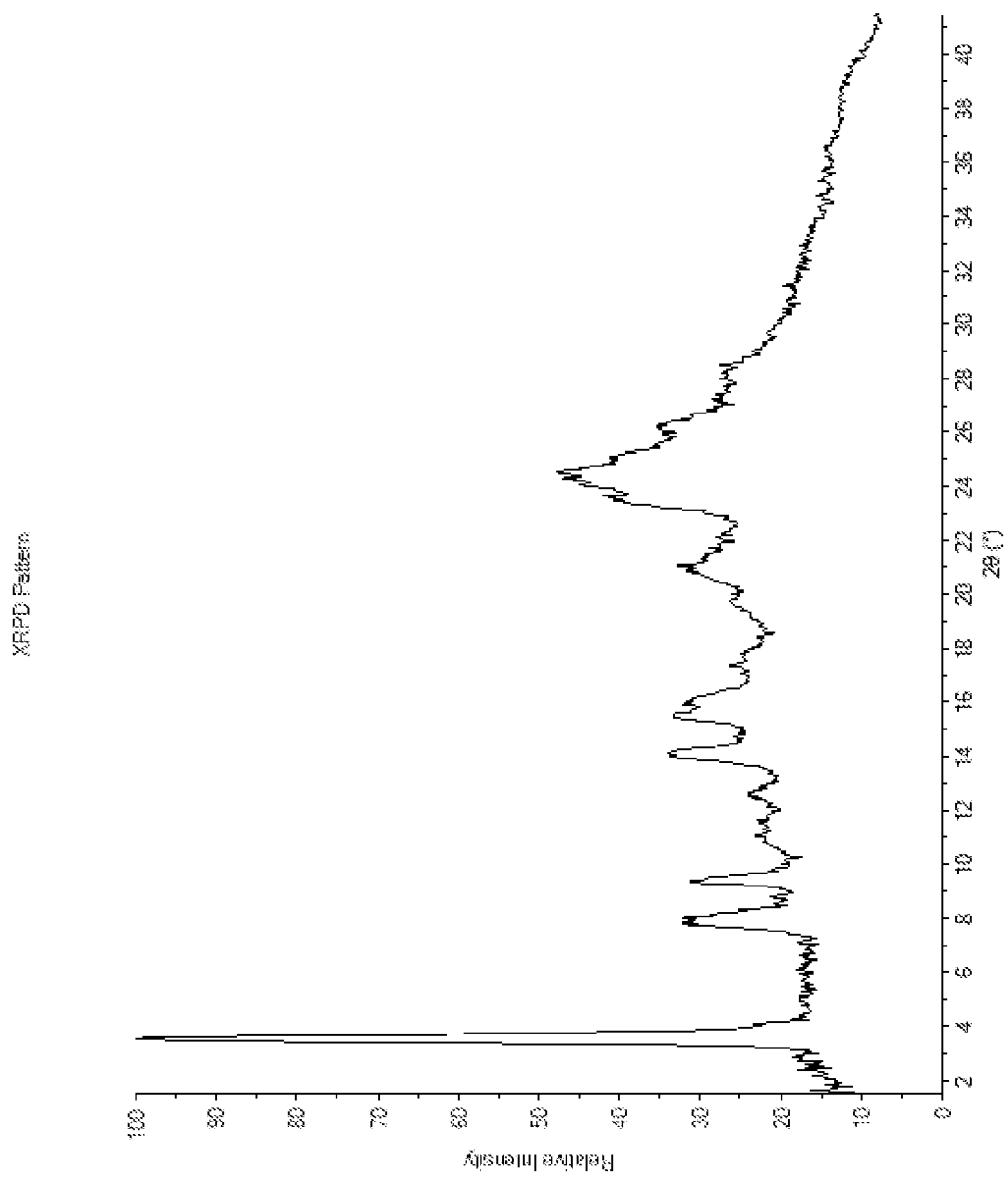
FIG. 23

Form M1 was obtained by cooling crystallization of Mixture A1+M1 in all of the following different solvent systems: acetonitrile/water (50:50), tetrahydrofuran/water (50:50), methanol/water (50:50), acetone/water (50:50), 2 butanone/water (50:50), ethyl acetate/methanol (50:50), and tetrahydrofuran/methanol (50:50). 80 µL of the respective solvent were added to ca. 4 mg of Mixture A1+M1. The temperature was increased to 60° C. and was kept for 60 min at 60° C. After cooling to 2° C. with a cooling rate of 20° C./min, the mixture was allowed to remain at 2° C. under stirring for 24 h. Form F was obtained by solvent evaporation under vacuum (5 mbar). Form F was exposed to climate chamber conditions of 40° C./75% RH for 67 h resulting in Form M1.
Preparation of Form M2
Form M2 (FIG. 23, Table 10) was obtained by crash-crystallisation with anti-solvent addition from Mixture A1+M4.

Example 7z

Form M2 was obtained by crash-crystallisation with anti-solvent addition of Mixture A1+M1 in all of the following different solvent systems: solvent: 1-butanol/water (9.6:90.4v/v) with each anti-solvent: acetonitrile, 2-butanone, tetrahydrofuran or ethyl acetate. A stock solution was prepared in 200 μL solvent, the concentration of of the compound of formula I being that attained at saturation at ambient temperature after equilibration for 24 h before filtering or with a cut off concentration of 170 mg/mL.

For each experiment, the anti-solvent was added to each solvent vial, with a solvent to anti-solvent ratio of 1:0.25. In the cases where no precipitation occurred, this ratio was increased to 1:1, and if again no precipitation occurred the ratio was increased to 1:4 (for all Form M2 preparations), with a waiting time of 60 min between the additions (up to the third addition). Since not enough solids precipitated for separation, samples were kept at 5° C. for three days. No precipitation occurred. The solvents were evaporated at 200 mbar until dry.

Using different solvent systems, different intermediate polymorphic forms, i.e. amorphous (from anti-solvent acetonitrile, 2-butanone), Form M1 (tetrahydrofuran) and Mixture F+M1 (ethyl acetate) were obtained. After storage of the measuring plate at accelerated ageing conditions (40° C./75% RH) for 65 h all these samples transformed to polymorphic form M2.

Preparation of Form M4

Figure 25:
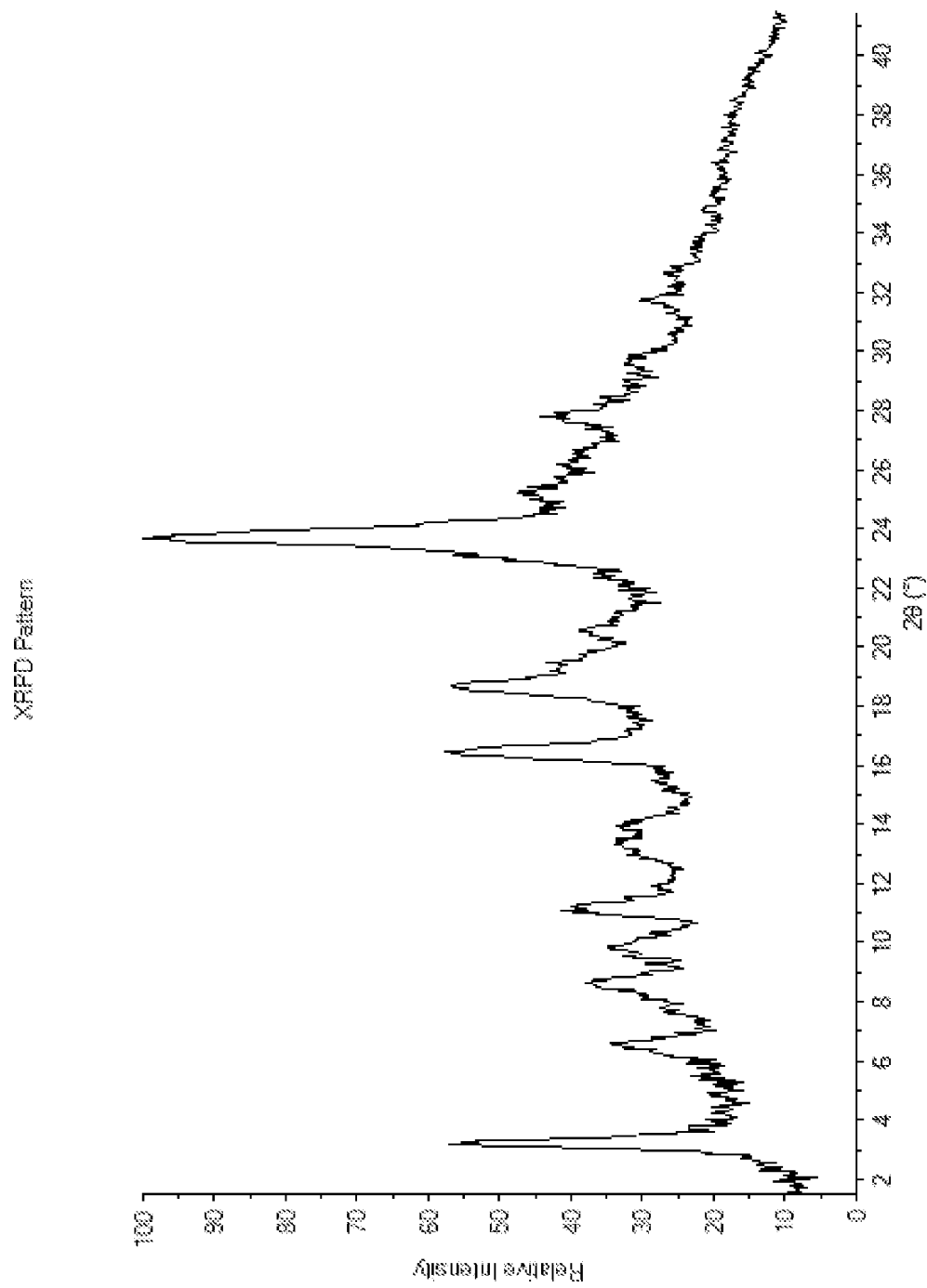
FIG. 25

Form M4 (FIG. 25, Table 12) was mainly obtained by slurry experiments at pH of 4 from Mixture A1+M4.

Example 7aa 151.4 mg of the compound of formula I (Mixture A1+M4) were suspended in 600 μL of pH4 buffer (Merck Titrisol® buffer pH4, with Citrate and HCl). The initial pH was ca. 3.2. After 15 min. the pH was adjusted with 25 μL 0.1M NaOH to ca. 4.1. After 2-4 h the pH was adjusted to 3.8. 10 μL 0.1M NaOH and 200 μL of the pH4 buffer were added. The slurry was stirred at RT for 24 h (including addition times). The slurry obtained showed ca. pH4.0. Filtration was performed using a 1 micron disk filter. Form M4 was obtained as the filter cake.

Example 7bb 198.3 mg of Mixture A1+M4 were suspended in 1000 μL of pH4 buffer (Merck Titrisol® buffer pH4, with Citrate and HCl). The initial pH was ca. 2.9. After 15 min the pH was adjusted with 50 μL 0.1M NaOH to ca. 3.8. The slurry was stirred at RT for 24 h (including addition times). A hazy solution is obtained with ca. pH3.8. Filtration was performed using a 1 micron disk filter. Form M4 was obtained as the filter cake.

Example 7cc 245.4 mg of Mixture A1+M4 were suspended in 1000 μL of pH4 buffer (Merck Titrisol® buffer pH4, with Citrate and HCl). The initial pH was ca. 3.1. After 15 min the pH was adjusted with 50 μL 0.1M NaOH to ca. 3.9. The slurry was stirred for 30-45 min and the pH was adjusted to ca. 3.9. 10 μL of 0.1M NaOH were added to result in ca. pH4.1. The slurry was stirred at RT for 24 h (including addition times). The slurry obtained showed ca. pH4.0. Filtration was performed using a 0.2 μm centrifugal filter. Form M4 was obtained as the filter cake.

Preparation of Form M5

The XRPD diffractogram is depicted in FIG. 26 and Table 13.

Example 7dd

Form M5 was obtained by storage of the compound of formula I Mixture A1+M1 or A1+M4 for 4 weeks at 40° C./75% RH.

Preparation of Form M8

Figure 27:
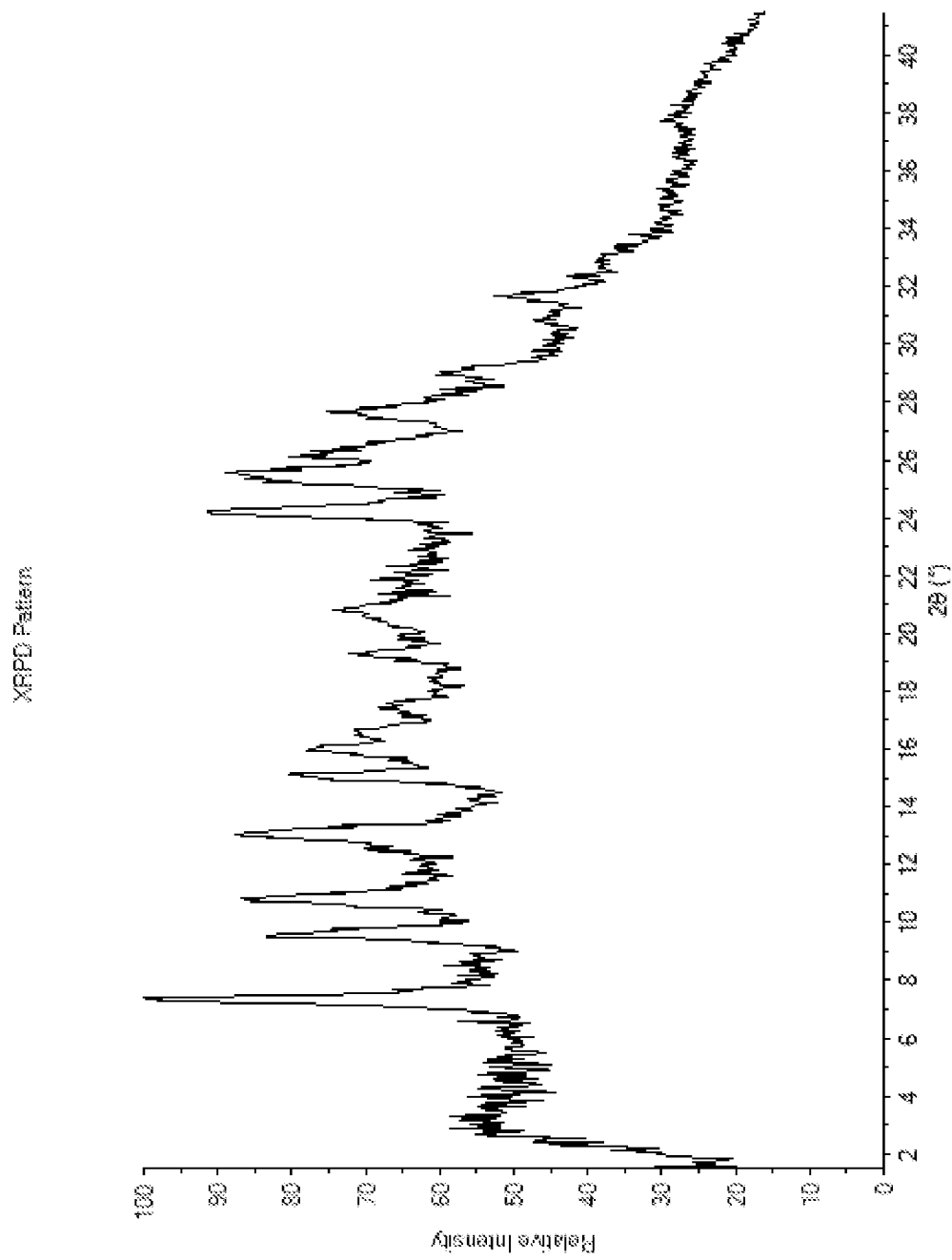
FIG. 27

Form M8 (FIG. 27, Table 14) was mainly obtained by slurry experiments at the pH of 7.5 from Mixture A1+M4. Note that these experiments used buffers containing alternative counter ions. Although it cannot be entirely discounted that traces of the counter ions were present in the polymorph, no diffraction peaks that could be attributable to these inorganic substances were visible in the XRPD diffractograms (inorganic substances are usually clearly visible at high 2θ angles and are usually very sharp peaks).

Example 7ee

Merck Titrisol® buffer pH7, with phosphate and Merck Titrisol® buffer pH8, with Borate and HCl were mixed in a ratio 1:1 (v/v) to give a buffer having a pH of 7.5. A suspension was prepared by adding 26.9 mg of Mixture A1+M4 to 5.0 mL of the above mentioned pH7.5 buffer. The resulting pH was ca. 7.3. After 15 min the pH was adjusted with 10 μL 0.1M NaOH to ca. pH7.4. The mixture was stirred at RT for 24 h (including addition times). A slurry was obtained with pH of ca. 7.5. Filtration was performed using a 1 micron disk filter. Form M8 was obtained as the filter cake.

Example 7ff

A suspension of 16.4 mg of Mixture A1+M4 in 5.0 mL of the above mentioned pH7.5 buffer was prepared. The initial pH was ca. 7.5. The resulting mixture was stirred at RT for 24 h. A slurry was obtained with ca. pH7.4. Filtration was performed using a 1 micron disk filter. Form M8 was obtained as the filter cake.

Preparation of Form M9

Figure 28:
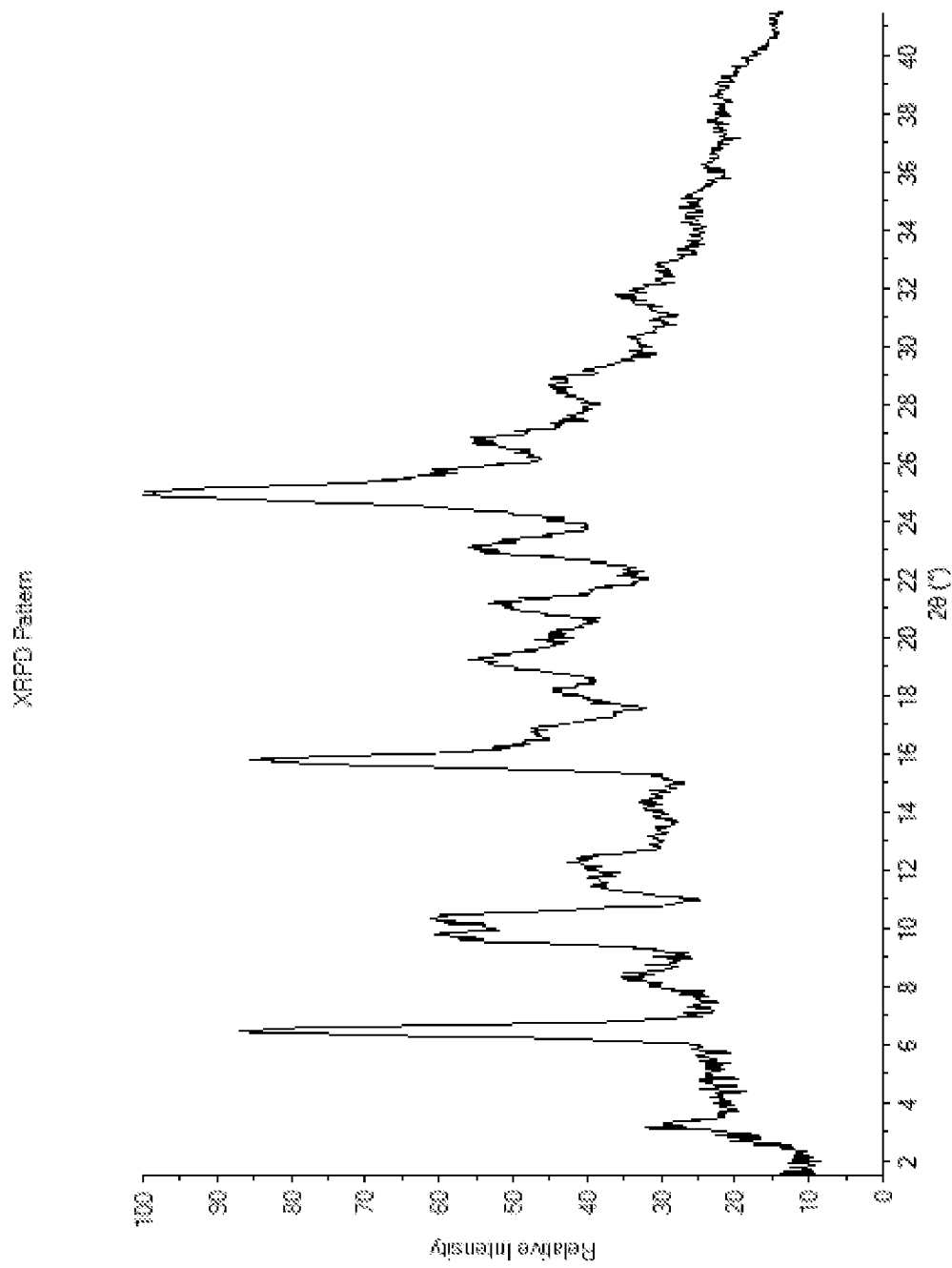
FIG. 28
Figure 29:
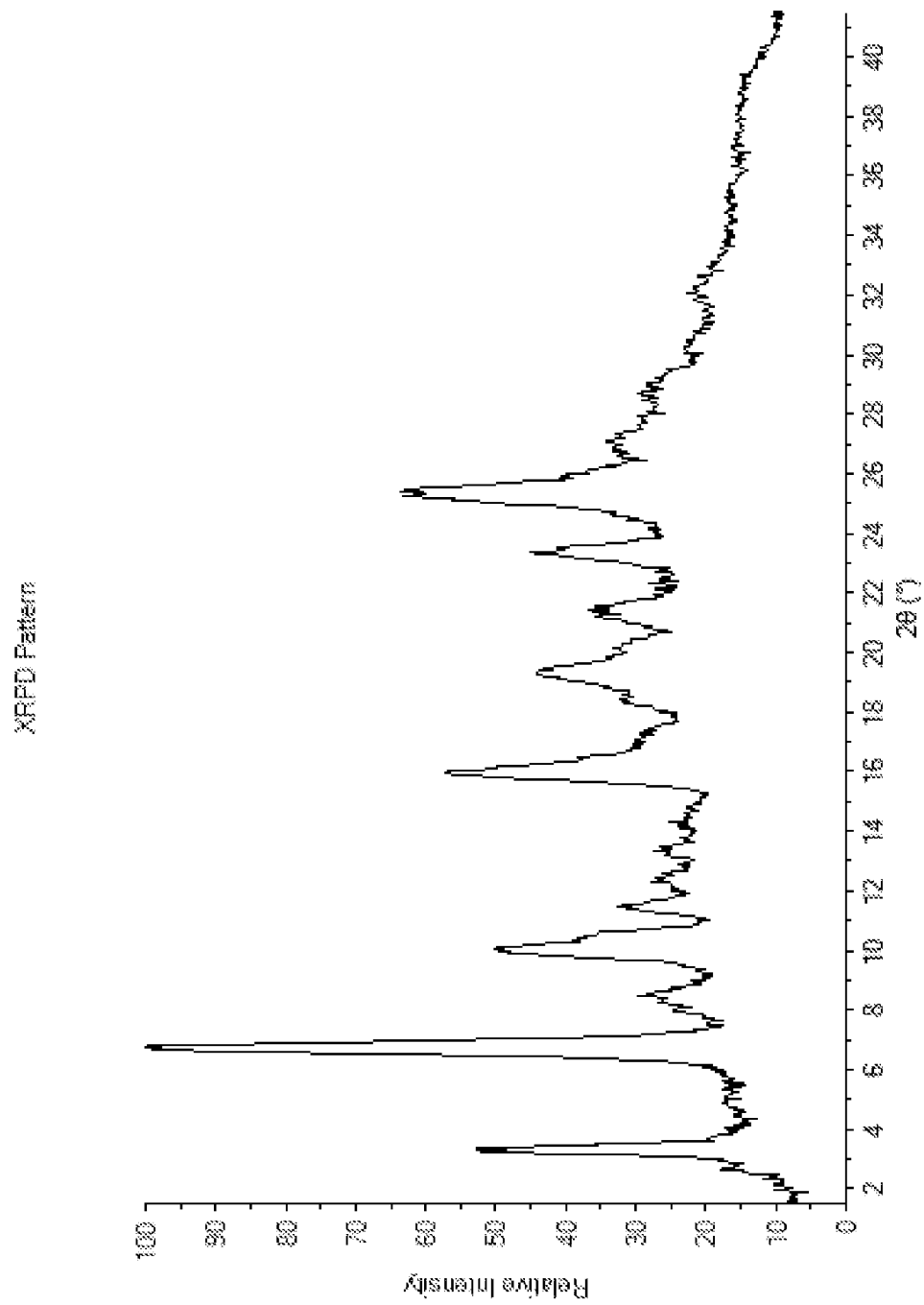
FIG. 29

Form M9 (FIG. 28, Table 15) was mainly obtained by slurry experiments in the pH range 4.5 to 5.5 from Mixture A1+M4. Note that these experiments used buffers containing alternative counter ions. Although it cannot be entirely discounted that traces of the counter ions were present in the polymorph, no diffraction peaks that could be attributable to these inorganic substances were visible in the XRPD diffractograms (inorganic substances are usually clearly visible at high 2θ angles and are usually very sharp peaks).

Example 7gg 150.5 mg of Mixture A1+M4 was suspended in 5.0 mL of Merck Titrisol® buffer (pH5, containing Citrate and NaOH). The initial pH was ca. 4.2. After 15 min. the pH was adjust with 70 μL 0.1M NaOH to ca. pH4.9. The mixture was stirred at RT for 24 h (including addition times). A slurry was obtained with ca. pH5.1. Filtration was performed using a 1 micron disk filter. Form M9 was obtained as the filter cake.

Example 7hh 32 mg of Mixture A1+M4 was suspended in 5.0 mL of Merck Titrisol® buffer (pH5, containing Citrate and NaOH). The initial pH was ca. 5.0. The mixture was stirred at RT for 24 h (including addition times). A slurry was obtained with ca. pH5.0. Filtration was performed using a 1 micron disk filter. Form M9 was obtained as the filter cake.

Example 7ii

Merck Titrisol® buffer pH5 (containing Citrate and NaOH) was mixed with Merck Titrisol® buffer pH6 (containing Citrate and NaOH) in a ratio 1:1 (v/v) to result in a buffer of pH5.5. 34 mg of the compound of formula I (Mixture A1+M4) were suspended in 5.0 mL of the above mentioned pH5.5 buffer. The initial pH was ca. 5.6. The mixture was stirred at RT for 24 h (including addition times). A slurry was obtained with ca. pH5.5. Filtration was performed using a 1 micron disk filter. Form M9 was obtained as the filter cake.
Preparation of Form M11

Figure 30:
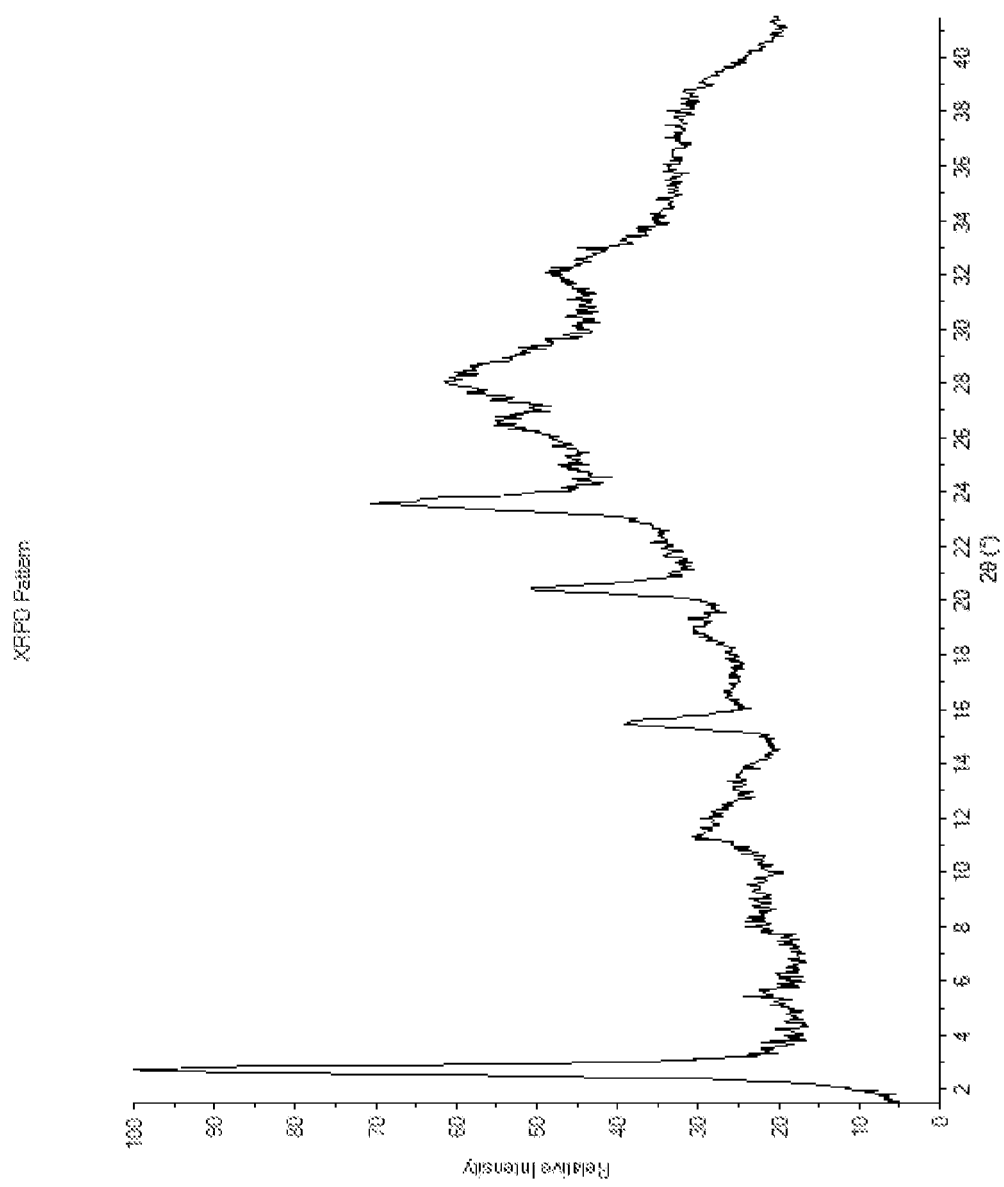
FIG. 30

Form M11 (FIG. 30, Table 16) was obtained in supersaturation experiments by changing the pH from 3 to 7 from Mixture A1+M4 and Form E. Note that these experiments used buffers containing alternative counter ions. Although it cannot be entirely discounted that traces of the counter ions were present in the polymorph, no diffraction peaks that could be attributable to these inorganic substances were visible in the XRPD diffractograms (inorganic substances are usually clearly visible at high 2θ angles and are usually very sharp peaks).

Example 7kk

Ca. 210 mg of Form E were suspended in 1.00 mL Merck Titrisol® buffer pH3 (containing Citrate and HCl) and 20 µL 0.1M NaOH were added. The saturated solution was filtered (0.2 µm centrifugal filter). The solution was kept at RT for 24 h prior to adjustment to pH7 by addition of 270 µL of 0.1M NaOH. Precipitation of solids occurred. The suspensions were filtered with 0.2 µm centrifugal filter and Form M11 was obtained as the filter cake. The same result was obtained using the unfiltered solution when using 350 µL of 0.1M NaOH for the pH adjustment to pH7.

Example 7ll

Ca. 420 mg of Mixture A1+M4 were suspended in 1.00 mL pH3 buffer and 40 µL of 0.1M NaOH were added. The saturated solution was filtered (0.2 µm centrifugal filter) and kept at RT for 24 h prior to adjustment to pH7 by addition of 300 µL of 0.1M NaOH. Precipitation of solids occurred. The suspension was filtered with 0.2 µm centrifugal filter and Form M11 was obtained as the filter cake. The same result was obtained using the unfiltered solution when using 350 µL of 0.1M NaOH for the pH adjustment to pH7.
Preparation of Form M12

Figure 31:
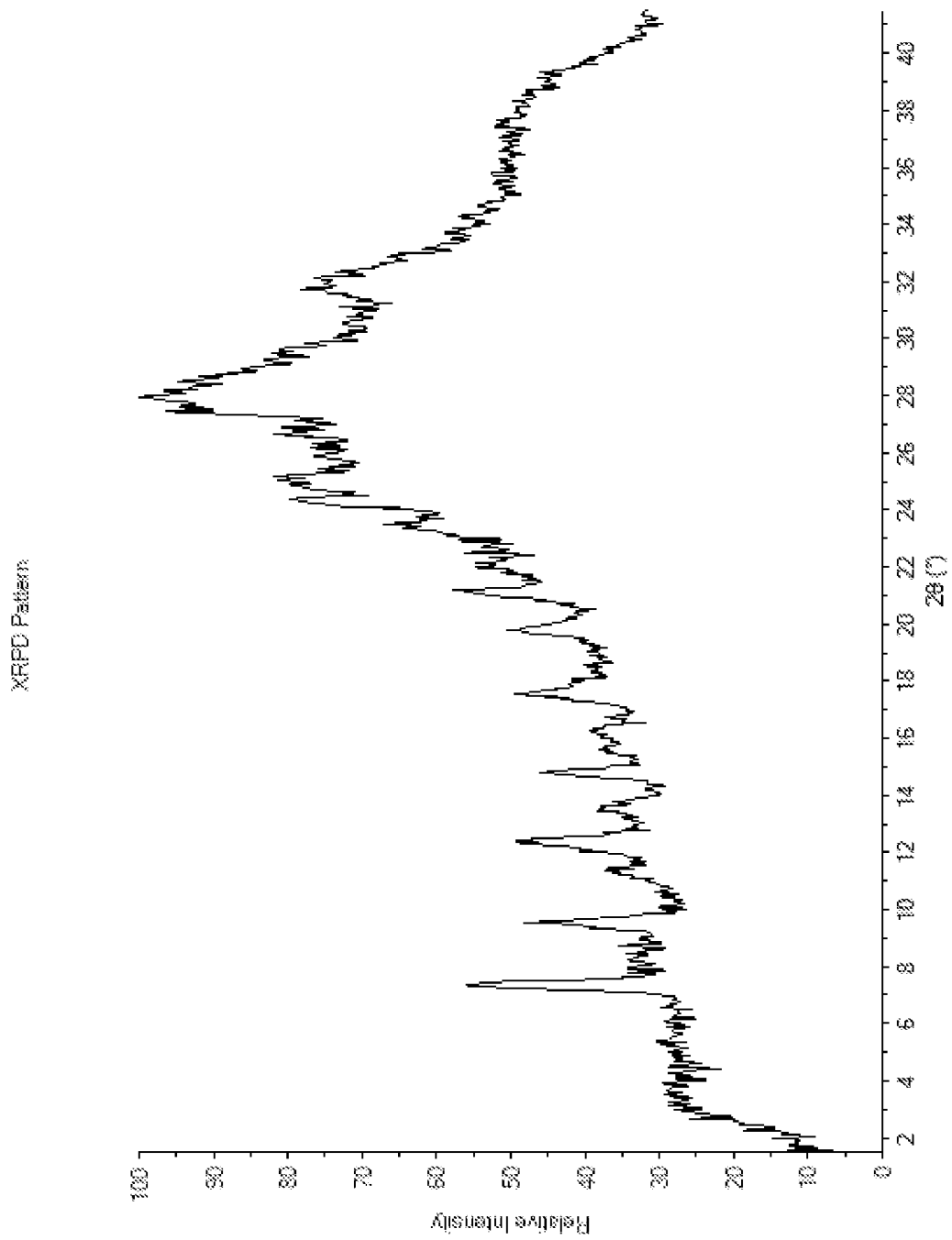
FIG. 31

Form M12 (FIG. 31, Table 17) was observed in different slurry experiments at ca. pH7 from Mixture A1+M4 and Form E. Note that these experiments used buffers containing alternative counter ions. Although it cannot be entirely discounted that traces of the counter ions were present in the polymorph, no diffraction peaks that could be attributable to these inorganic substances were visible in the XRPD diffractograms (inorganic substances are usually clearly visible at high 2θ angles and are usually very sharp peaks).

Example 7 mm

Ca. 30 mg of Mixture A1+M4 or Form E were suspended in 5.0 mL of Merck Titrisol® buffer pH7 (containing phosphate). The initial pH was ca. 6.9. After stirring for 15 min the pH was adjust with 10 µL 0.1M NaOH to ca. 7.0. The mixture was stirred at RT for 24 h (including addition times). A slurry was obtained with ca. pH7.0. Filtration was performed using a 0.45 micron disk filter. Form M12 was obtained as the filter cake.
Preparation of Form M13

Figure 32:
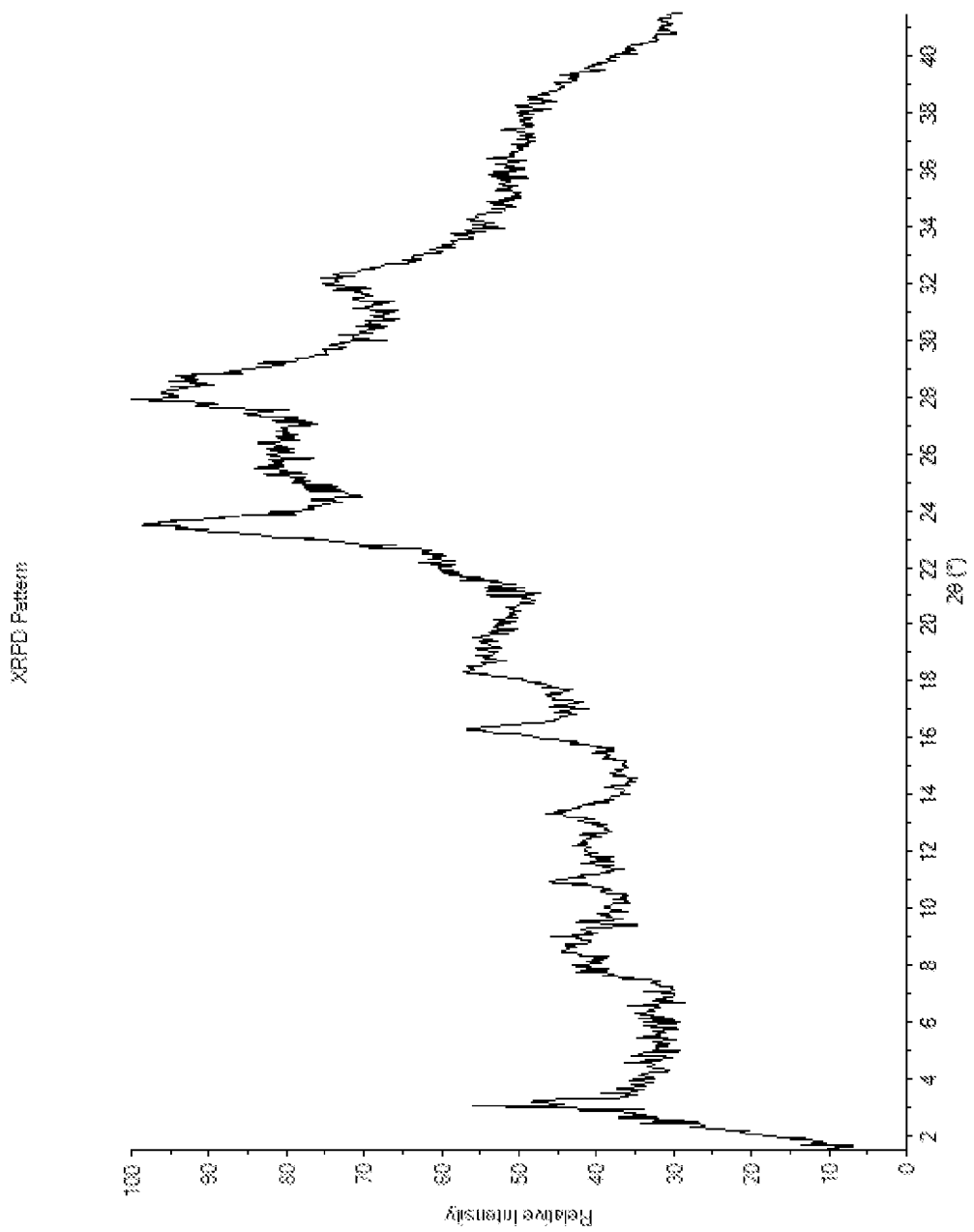
FIG. 32
Figure 33:
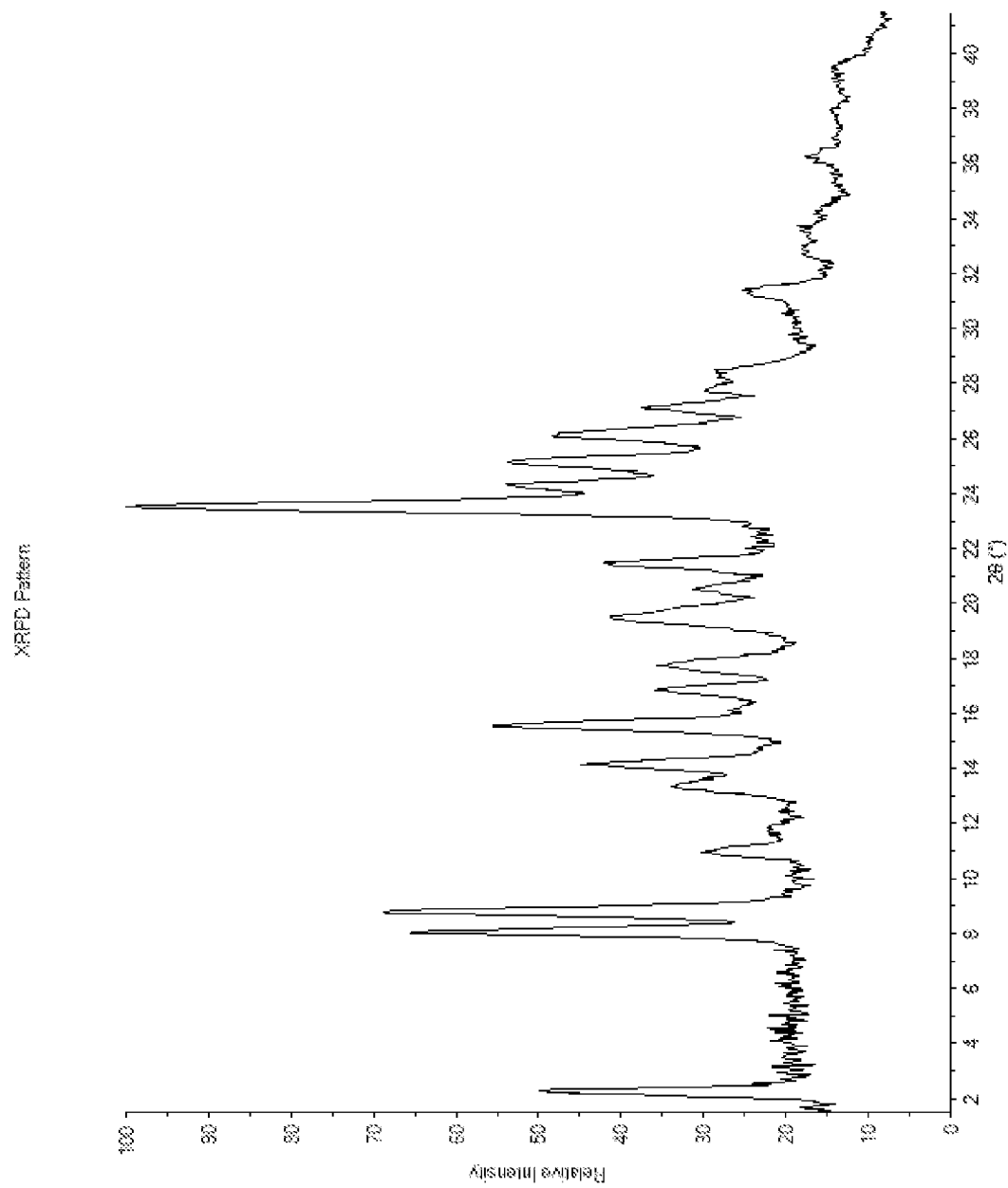
FIG. 33
Figure 34:
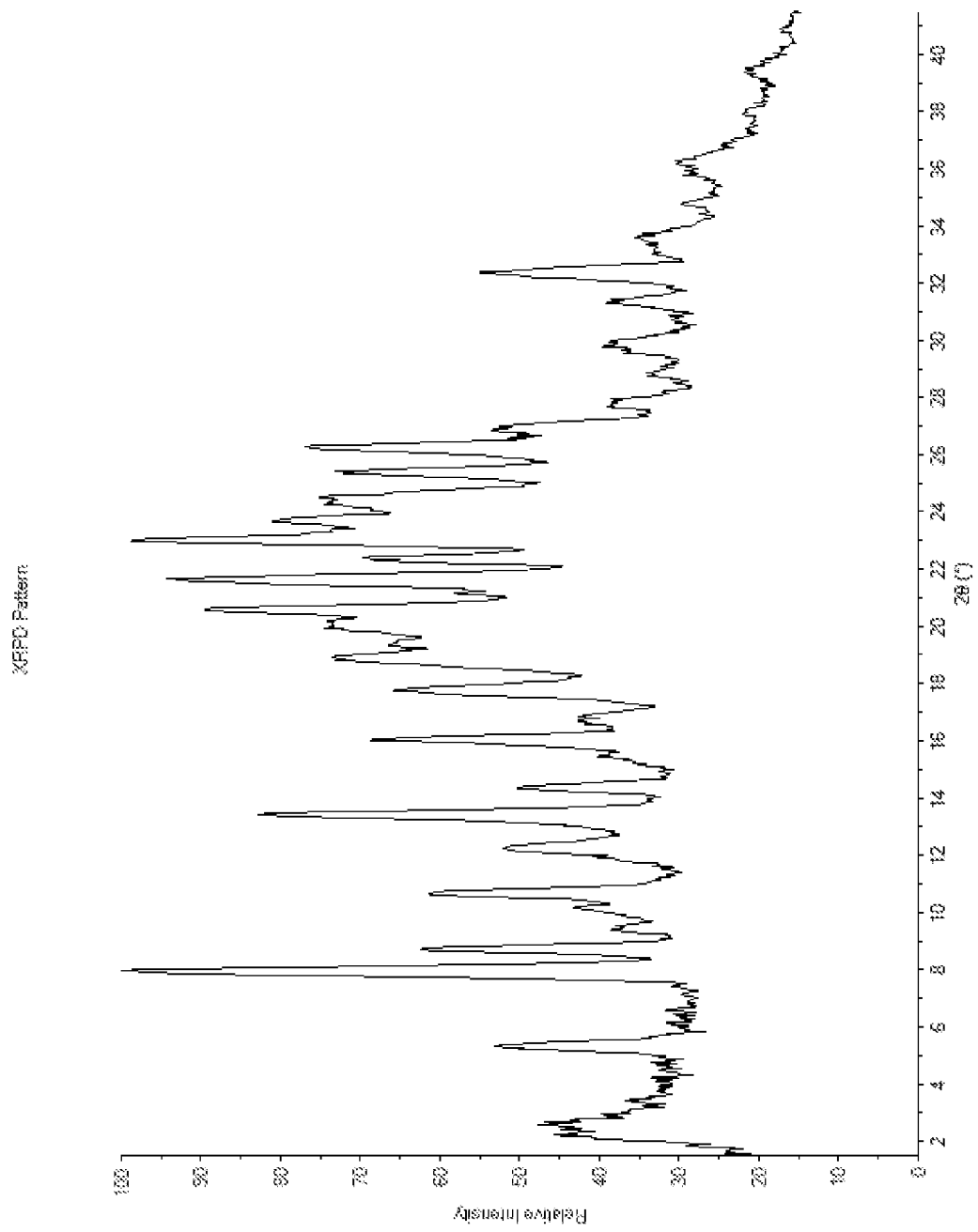
FIG. 34

Form M13 (FIG. 32, Table 18) was obtained in supersaturation experiments by changing the pH from 3 to 5 from Mixture A1+M4 and Form E. Note that these experiments used buffers containing alternative counter ions. Although it cannot be entirely discounted that traces of the counter ions were present in the polymorph, no diffraction peaks that could be attributable to these inorganic substances were visible in the XRPD diffractograms (inorganic substances are usually clearly visible at high 2θ angles and are usually very sharp peaks).

Example 7nn

Ca. 210 mg of Form E were suspended in 1.0 mL Merck Titrisol® buffer pH3 (containing Citrate and HCl) and 20 µL 0.1M NaOH were added. The saturated solution was filtered (0.2 µm centrifugal filter) and was kept at RT for 24 h prior to an adjustment to pH5 by addition of ca. 50 µL 0.1M NaOH.

Precipitation of solids occurred. The suspensions were filtered with 0.2 µm centrifugal filter and form M13 was obtained as the filter cake. The same result was obtained using the unfiltered solution when using 70 µL of 0.1M NaOH for the pH adjustment to pH5.

Example 7oo

Ca. 410 mg of Mixture A1+M4 were suspended in 1.00 mL Merck Titrisol® buffer pH3 (containing Citrate and HCl) and 40 µL 0.1M NaOH were added. The saturated solution was filtered (0.2 µm centrifugal filter) and was kept at RT for 24 h prior to an adjustment to pH5 by addition of 60 µL of 0.1M NaOH. Precipitation of solids occurred. The suspensions were filtered with 0.2 µm centrifugal filter and form M13 was obtained as the filter cake. The same result was obtained using the unfiltered solution when using 80 µL of a 0.1M NaOH for the pH adjustment to pH5.

Note: Although Forms F and G are described above as intermediate forms in the preparation of some polymorphic forms within the A+M System in the Examples above, the solvent appears to play an important role in their physical stability. Forms F and G may be solvated or anhydrous forms that occur depending on the solvent used.

Example 8-Characterization of the Crystalline Dichloride Salt (A+M) of the Compound of Formula I Example 8a: Characterization by XRPD XRPD analysis was performed as described under Example 5a. These include XRPD peaks for mixtures that arise naturally in the A+M system, as well as specific A or M polymorphs, isolated as described. Data is included for polymorphs A0, A1, A2, M1, M2, M3+M5, M4, M5, M8, M9, M10+M4, M11, M12, M13 as well as the commonly observed mixtures of A1+M4, A2+M4 and A2+M11. Forms M6 and M7 were also observed but only as mixtures with other polymorphic forms not part of the A+M System.

TABLE 6

List of XRPD peak positions of Form A0.

| Angle [2θ] | d-Spacing [Å] | Intensity [rel. %] |
|---|---|---|
| 3.9 | 22.40 | 100 |
| 7.9 | 11.18 | 91 |
| 9.7 | 9.11 | 79 |
| 11.2 | 7.90 | 82 |
| 23.9 | 3.72 | 75 |
| 25.0 | 3.55 | 83 |
| 25.5 | 3.48 | 82 |

TABLE 7

List of XRPD peak positions of Forms A1.

| Angle [2θ] | d-Spacing [Å] | Intensity [rel. %] |
|---|---|---|
| 4.0 | 21.95 | 58 |
| 8.1 | 10.96 | 52 |
| 9.4 | 9.38 | 65 |
| 11.1 | 7.99 | 24 |
| 12.7 | 6.98 | 23 |
| 15.3 | 5.80 | 53 |
| 18.3 | 4.84 | 11 |
| 20.8 | 4.26 | 31 |
| 24.3 | 3.65 | 100 |
| 25.5 | 3.48 | 30 |

TABLE 8

List of XRPD peak positions of Form A2.

| Angle [2θ] | d-Spacing [Å] | Intensity [rel. %] |
|---|---|---|
| 3.9 | 22.4 | 35 |
| 8.2 | 10.74 | 54 |
| 9.4 | 9.38 | 100 |
| 11.6 | 7.63 | 15 |
| 12.7 | 6.98 | 31 |
| 14.7 | 6.00 | 43 |
| 15.5 | 5.71 | 37 |
| 19.8 | 4.48 | 34 |
| 24.1 | 3.68 | 92 |
| 25.1 | 3.55 | 50 |
| 25.6 | 3.47 | 41 |

TABLE 9

List of XRPD peak positions of Forms M1.

| Angle [2θ] | d-Spacing [Å] | Intensity [rel. %] |
|---|---|---|
| 3.6 | 24.38 | 100 |
| 7.9 | 11.23 | 25 |
| 9.5 | 9.34 | 19 |
| 15.5 | 5.72 | 17 |
| 24.5 | 3.62 | 34 |

TABLE 10

List of XRPD peak positions of Form M2.

| Angle [2θ] | d-Spacing [Å] | Intensity [rel. %] |
|---|---|---|
| 3.5 | 24.93 | 100 |
| 9.4 | 9.42 | 15 |

TABLE 11

List of XRPD peak positions of Mixture M3 + M5.

| Angle [2θ] | d-Spacing [Å] | Intensity [rel %] |
|---|---|---|
| 3.0 | 29.61 | 92 |
| 3.6 | 24.38 | 99 |
| 9.4 | 9.38 | 66 |
| 11.1 | 7.99 | 48 |
| 12.7 | 6.96 | 46 |
| 15.3 | 5.77 | 56 |
| 23.6 | 3.76 | 70 |
| 24.5 | 3.63 | 100 |

TABLE 12

List of XRPD peak positions of Form M4.

| Angle [2θ] | d-Spacing [Å] | Intensity [rel %] |
|---|---|---|
| 3.2 | 27.41 | 55 |
| 6.5 | 13.5 | 34 |
| 8.6 | 10.25 | 38 |
| 9.8 | 9.00 | 34 |
| 11.2 | 7.90 | 40 |
| 11.9 | 7.43 | 29 |
| 13.3 | 6.63 | 34 |
| 16.5 | 5.38 | 58 |
| 18.7 | 4.75 | 57 |
| 20.5 | 4.32 | 39 |
| 23.7 | 3.76 | 100 |
| 25.2 | 3.53 | 45 |
| 27.8 | 3.20 | 41 |
| 31.7 | 2.82 | 31 |

TABLE 13

List of XRPD peak positions of Form M5.

| Angle [2θ] | d-Spacing [Å] | Intensity [rel %] |
|---|---|---|
| 3.7 | 24.11 | 100 |
| 7.5 | 11.77 | 25 |
| 9.4 | 9.38 | 46 |
| 15.3 | 5.77 | 27 |
| 19.8 | 4.47 | 14 |
| 24.3 | 3.65 | 65 |

TABLE 14

List of XRPD peak positions of Form M8.

| Angle [2θ] | d-Spacing [Å] | Intensity [rel %] |
|---|---|---|
| 7.3 | 12.03 | 100 |
| 9.6 | 9.22 | 60 |
| 10.8 | 8.17 | 69 |
| 13.1 | 6.77 | 70 |

TABLE 14-continued

List of XRPD peak positions of Form M8.

| Angle [2θ] | d-Spacing [Å] | Intensity [rel %] |
|---|---|---|
| 15.1 | 5.88 | 51 |
| 16.0 | 5.53 | 47 |
| 16.5 | 5.35 | 34 |
| 19.3 | 4.59 | 27 |
| 20.8 | 4.26 | 28 |
| 24.2 | 3.67 | 66 |
| 25.5 | 3.49 | 60 |
| 26.2 | 3.40 | 43 |
| 27.7 | 3.22 | 43 |
| 31.7 | 2.82 | 30 |

TABLE 15

List of XRPD peak positions of Form M9.

| Angle [2θ] | d-Spacing [Å] | Intensity [rel %] |
|---|---|---|
| 3.2 | 27.75 | 27 |
| 6.5 | 13.67 | 88 |
| 9.7 | 9.07 | 59 |
| 10.3 | 8.55 | 62 |
| 15.8 | 5.61 | 87 |
| 18.1 | 4.88 | 45 |
| 19.2 | 4.62 | 54 |
| 21.1 | 4.21 | 51 |
| 23.1 | 3.85 | 57 |
| 25.0 | 3.56 | 100 |
| 26.8 | 3.33 | 56 |

TABLE 16

List of XRPD peak positions of Form M11.

| Angle [2θ] | d-Spacing [Å] | Intensity [rel %] |
|---|---|---|
| 2.7 | 32.21 | 100 |
| 15.5 | 5.71 | 21 |
| 20.4 | 4.34 | 25 |
| 23.6 | 3.76 | 35 |

TABLE 17

List of XRPD peak positions of Form M12.

| Angle [2θ] | d-Spacing [Å] | Intensity [rel %] |
|---|---|---|
| 7.3 | 12.03 | 100 |
| 9.5 | 9.26 | 56 |
| 11.3 | 7.79 | 25 |
| 12.4 | 7.14 | 66 |
| 13.5 | 6.55 | 28 |
| 14.8 | 5.99 | 50 |
| 15.6 | 5.68 | 24 |
| 17.6 | 5.04 | 51 |
| 19.8 | 4.48 | 37 |
| 21.1 | 4.21 | 41 |
| 23.4 | 3.79 | 29 |
| 24.3 | 3.66 | 63 |
| 25.9 | 3.44 | 27 |
| 26.7 | 3.34 | 31 |
| 27.5 | 3.24 | 73 |
| 27.9 | 3.19 | 87 |
| 29.6 | 3.02 | 32 |
| 32.1 | 2.79 | 42 |

TABLE 18

List of XRPD peak positions of Form M13.

| Angle [2θ] | d-Spacing [Å] | Intensity [rel %] |
|---|---|---|
| 3.1 | 28.1 | 73 |
| 8.6 | 10.29 | 36 |
| 11.0 | 8.05 | 32 |
| 13.3 | 6.63 | 28 |
| 16.3 | 5.43 | 53 |
| 17.5 | 5.07 | 20 |
| 18.4 | 4.82 | 44 |
| 23.5 | 3.77 | 100 |
| 25.5 | 3.49 | 34 |
| 28.0 | 3.18 | 63 |
| 28.6 | 3.12 | 57 |

TABLE 19

List of XRPD peak positions of Mixture A1 + M1.

| Angle [2θ] | d-Spacing [Å] | Intensity [rel %] |
|---|---|---|
| 3.6 | 24.65 | 76 |
| 4.0 | 22.17 | 91 |
| 8.1 | 10.9 | 73 |
| 9.4 | 9.42 | 56 |
| 11.0 | 8.05 | 57 |
| 21.1 | 4.21 | 56 |
| 24.5 | 3.63 | 100 |

TABLE 20

List of XRPD peak positions of Mixture A1 + M4.

| Angle [2θ] | d-Spacing [Å] | Intensity [rel %] |
|---|---|---|
| 3.4 | 25.8 | 92 |
| 4.0 | 22.17 | 67 |
| 8.1 | 10.85 | 50 |
| 11.1 | 7.93 | 50 |
| 16.5 | 5.38 | 54 |
| 24.0 | 3.7 | 100 |

TABLE 21

List of XRPD peak positions of Mixture A2 + M4.

| Angle [2θ] | d-Spacing [Å] | Intensity [rel %] |
|---|---|---|
| 3.01 | 28.84 | 100 |
| 6.9 | 12.87 | 27 |
| 8.5 | 10.44 | 52 |
| 9.4 | 9.38 | 62 |
| 12.6 | 7.01 | 40 |
| 14.8 | 5.99 | 42 |
| 15.4 | 5.74 | 48 |
| 19.8 | 4.48 | 45 |
| 22.7 | 3.91 | 35 |
| 24.3 | 3.66 | 80 |
| 24.9 | 3.57 | 60 |

TABLE 22

List of XRPD peak positions of Mixture A2 + M11.

| Angle [2θ] | d-Spacing [Å] | Rel. Intensity [%] |
|---|---|---|
| 2.7 | 32.21 | 100 |
| 8.3 | 10.69 | 31 |
| 9.4 | 9.38 | 39 |
| 14.8 | 5.99 | 31 |
| 19.7 | 4.49 | 30 |
| 24.1 | 3.69 | 37 |

TABLE 23

List of XRPD peak positions of Form F.

| Angle [2θ] | d-Spacing [Å] | Rel. Intensity [%] |
|---|---|---|
| 2.3 | 39.0 | 45 |
| 8.0 | 11.0 | 58 |
| 8.8 | 10.1 | 65 |
| 11.0 | 8.1 | 15 |
| 13.4 | 6.6 | 20 |
| 14.1 | 6.3 | 32 |
| 15.6 | 5.7 | 47 |
| 16.9 | 5.3 | 21 |
| 17.7 | 5.0 | 19 |
| 19.5 | 4.6 | 27 |
| 20.5 | 4.3 | 12 |
| 21.5 | 4.1 | 26 |
| 23.5 | 3.8 | 100 |
| 24.3 | 3.7 | 41 |
| 25.1 | 3.5 | 41 |
| 26.1 | 3.4 | 35 |
| 27.1 | 3.3 | 21 |

TABLE 24

List of XRPD peak positions of Form G.

| Angle [2θ] | d-Spacing [Å] | Rel. Intensity [%] |
|---|---|---|
| 2.3 | 39.04 | 42 |
| 2.5 | 34.74 | 44 |
| 5.3 | 16.53 | 37 |
| 7.9 | 11.12 | 100 |
| 8.7 | 10.11 | 49 |
| 9.4 | 9.38 | 18 |
| 10.1 | 8.71 | 25 |
| 10.7 | 8.29 | 54 |
| 12.3 | 7.21 | 42 |
| 13.4 | 6.59 | 82 |
| 14.3 | 6.17 | 35 |
| 16.1 | 5.51 | 50 |
| 17.7 | 4.99 | 40 |
| 18.9 | 4.70 | 47 |
| 19.4 | 4.57 | 34 |
| 20.0 | 4.43 | 43 |
| 20.6 | 4.31 | 63 |
| 21.6 | 4.11 | 65 |
| 22.3 | 3.97 | 33 |
| 23.0 | 3.86 | 74 |
| 23.7 | 3.75 | 51 |
| 24.4 | 3.64 | 45 |
| 25.4 | 3.51 | 45 |
| 26.3 | 3.39 | 55 |
| 26.9 | 3.31 | 26 |
| 31.3 | 2.85 | 22 |
| 32.3 | 2.76 | 44 |

Example 8b: Experimental High-Resolution X-Ray Powder Diffraction (Including Variable Humidity and Variable Temperature XRPD Experiments)

For variable humidity (VH) and variable temperature (VT) experiments a ANSYCO HT chamber was used, installed within a D8 Advance system diffractometer (Bruker) designed with Bragg-Brentano geometry and equipped with LynxEye solid state detector. The radiation used for collecting the data was CuKα1 (2=1.54056 Å) monochromatized by germanium crystal. The material was placed on a fixed sample holder that was mounted inside the chamber.

VH-XRPD: The humidity was applied locally and varied from 10 to 70% (dew point). The patterns were collected in the range 4-30° (2θ), with a step of 0.0145° (2θ) for the VH-XRPD and measuring time per step of 1.2 sec. Data collection was initiated 60 sec following stabilization of humidity at each step (data collection time per RH value about 40 min). All patterns were taken at Room Temperature, ca. 295 K.

VT-XRPD: The temperature variation rate was 10° C./min and the equilibration time, prior to starting the data collection at each temperature, was 8 min. The patterns were collected in the range 4-34.5° (2θ), with a step of 0.0107° (2θ) and measuring time per step of 1 sec (for T=25, 50, 80, 100 and 110° C.) or 1.5 sec (for T=40, 60, 115-180° C.). The data collection time, per temperature, was 48 or 70 min, depending on the measuring time per step.

Form A1+M4 was put to a climate chamber experiment at 40° C./75% RH for 4 weeks followed by storage at 25° C./95% RH for two weeks. During this study the initial Form A1+M4 changed after one week into M3+M5, after 4 weeks into form M5 and after 4 weeks and two days into Form A2+M4 before eventually transforming into Form A2+M11 (FIG. 19).

Example 8c: Characterization by DVS

Figure 35:
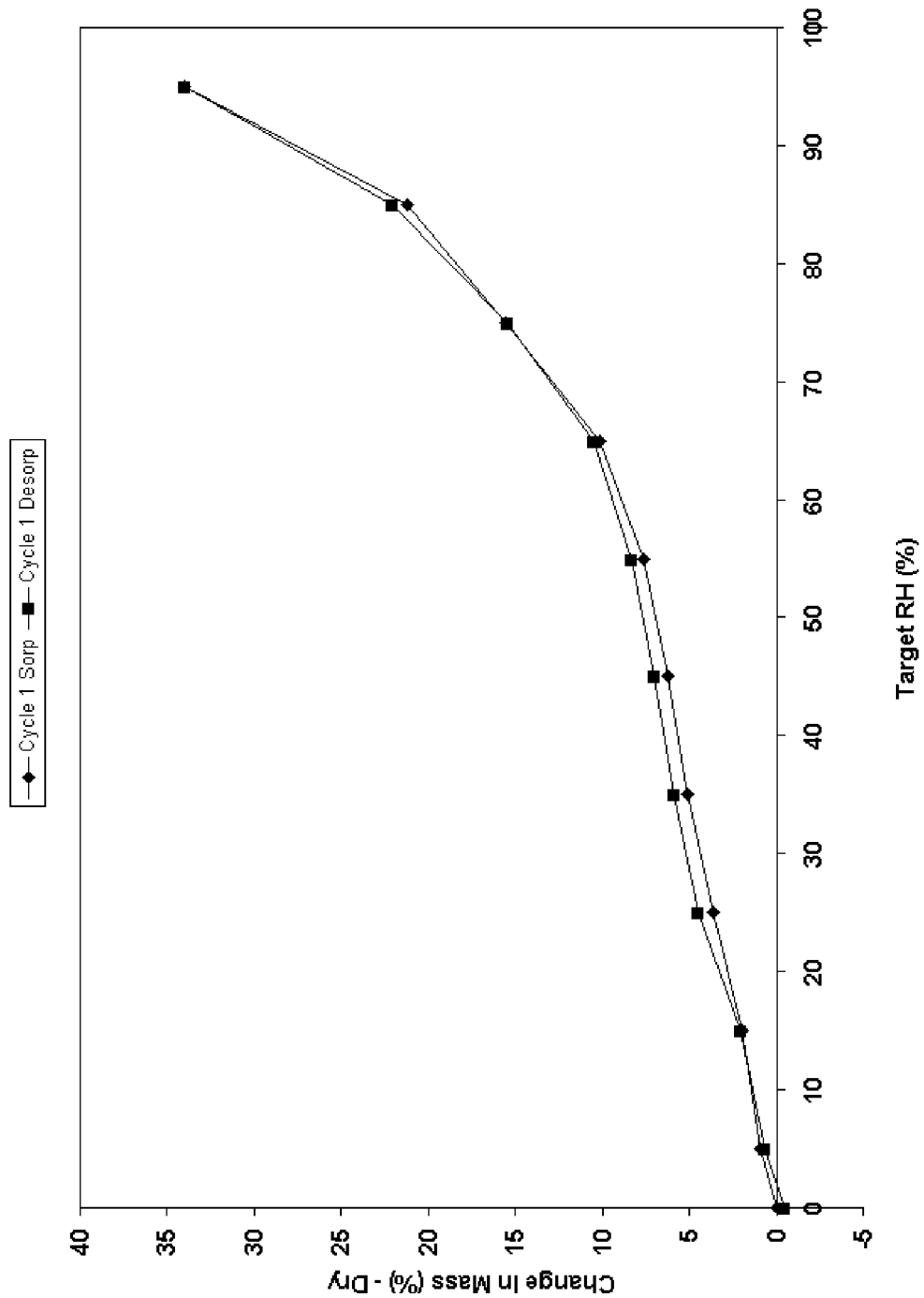
FIG. 35
Figure 36:
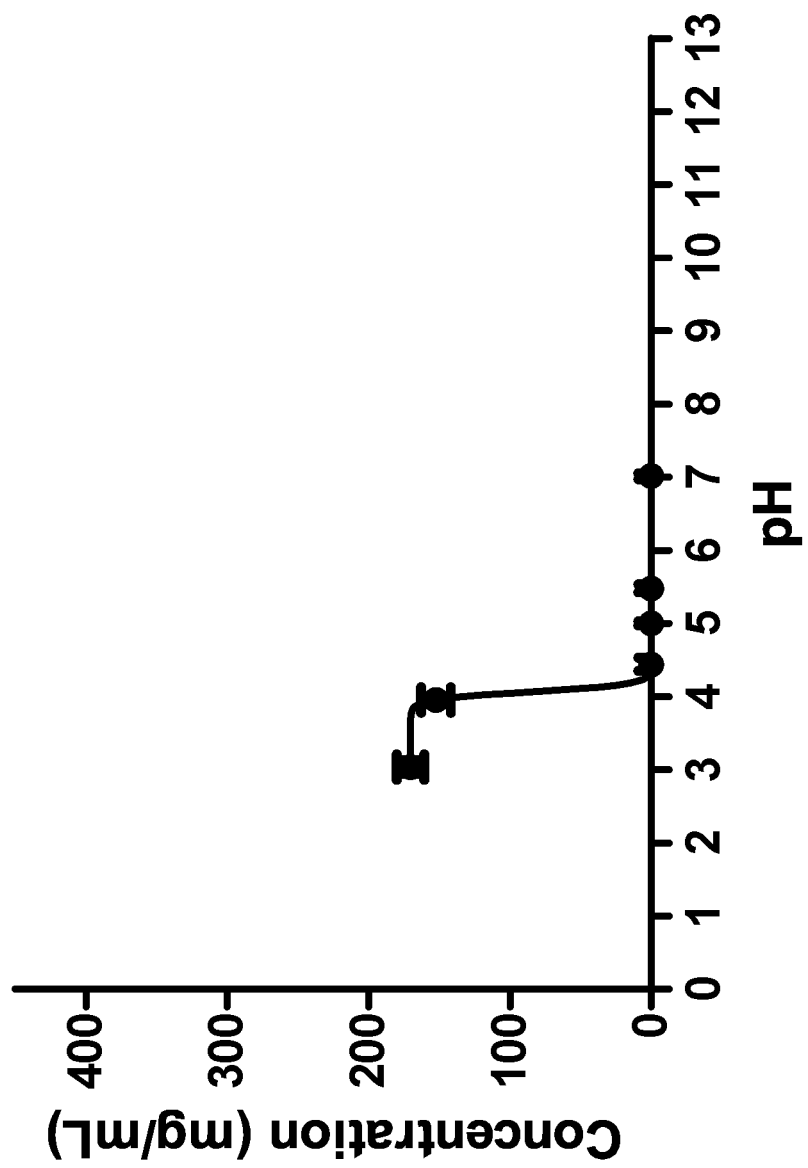
FIG. 36
Figure 37B:
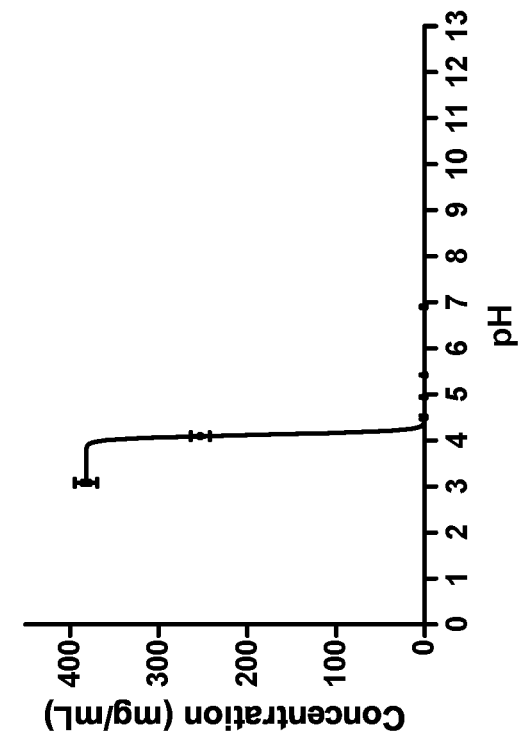
FIGS. 37A and 37B
Figure 37A:
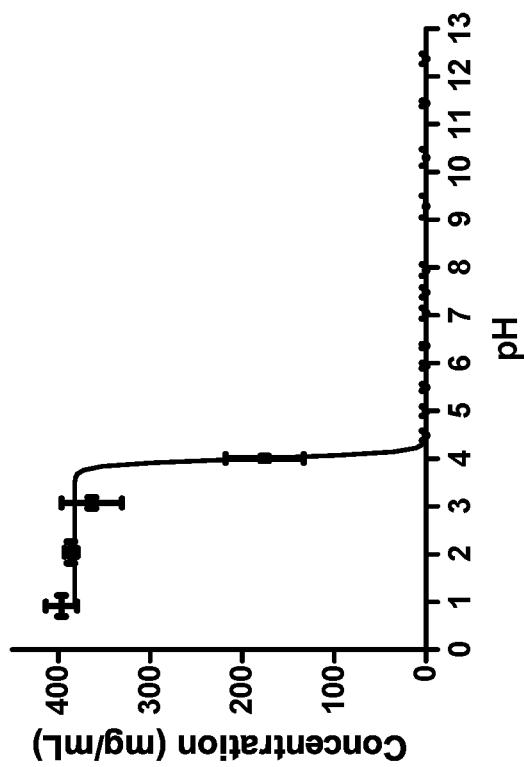
Figure 38:
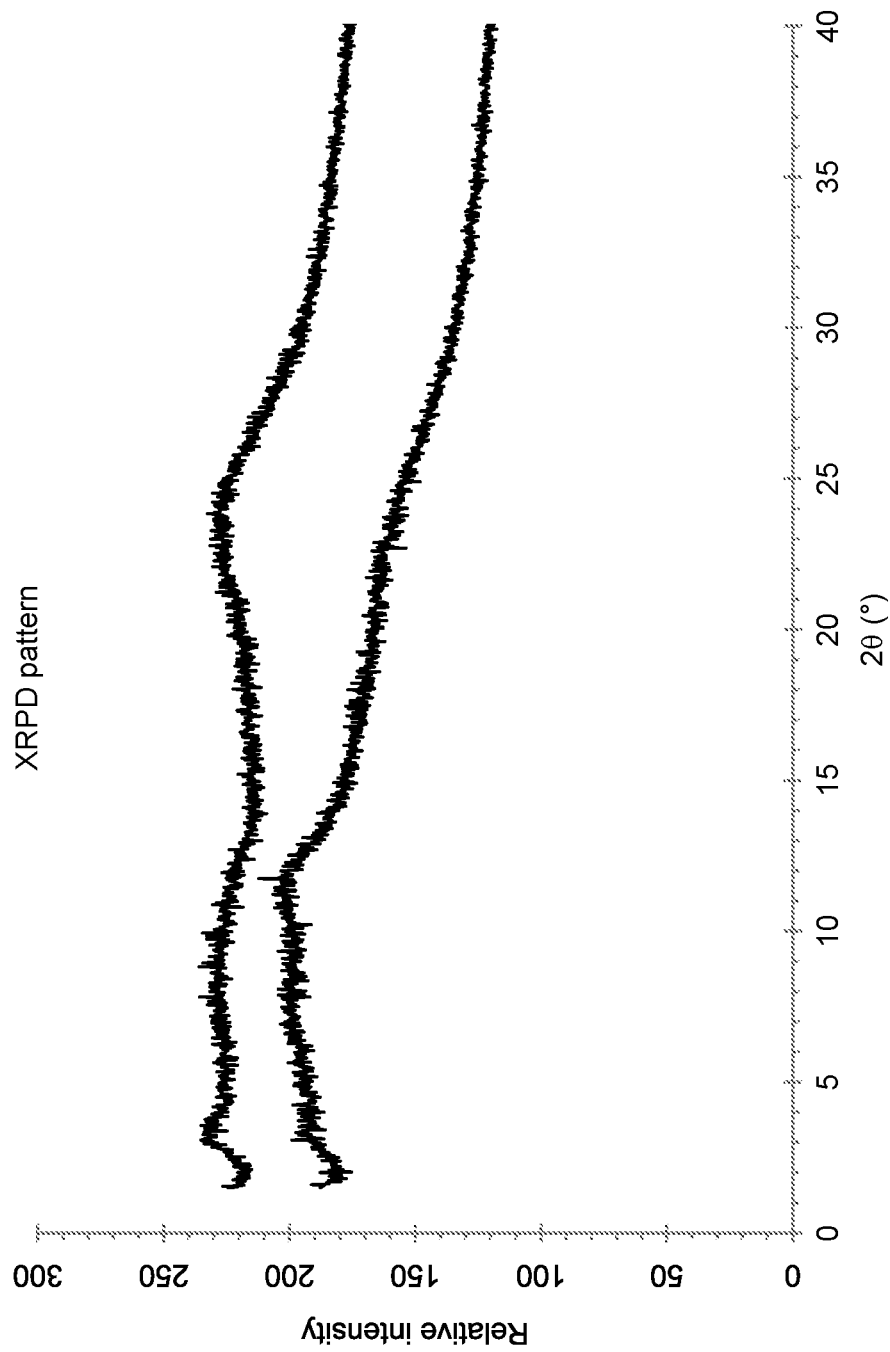
FIG. 38

See Example 5f for experimental details. The DVS analysis for the crystalline System A+M of the dichloride salt of the compound of formula I is depicted in FIG. 35. It shows ca. 22% water absorption for the compound up to 85% RH and below ca. 34% water absorption up to 95% RH.

Example 8d: Solubility

The thermodynamic pH-dependent solubility of Form A1+M4 was determined as described in Example 5g for Form E, except that the target pHs were 1, 2, 3 (two different buffers), 4, 4.5, 5, 5.5, 6, 6.5, 7.5, 8, 9.5, 10.5, 11.5 and 12.5. The additionally used buffers were Merck Titrisol® buffer pH 1 with glycin and HCl; Merck Titrisol® buffer pH 2 with citrate and HCl; Merck Titrisol® buffer pH 8 with borate and HCl; Merck Titrisol® buffer pH 9 with boric acid, KCl and NaOH; Merck Titrisol® buffer pH 10 with boric acid, KCl and NaOH; Merck Titrisol® buffer pH 11 with boric acid, KCl and NaOH; Merck Titrisol® buffer pH 12 with phosphate and NaOH; Merck Titrisol® buffer pH 13 with KCl and NaOH; for a second buffer at pH 3 without HCl 80.3 mL of citric acid (21.01 g citric acid monohydrate in 1 L deionized water) were mixed with 19.7 mL of 0.2M disodiumhydrogenphosphate (35.6 g in 1 L deionized water). For buffering at pH 6.5 a 50/50 mixture of buffers for pH 6 and 7 was used; for buffering at pH 7.5 a 50/50 mixture of buffers for pH 7 and 8 was used; for buffering at pH 9.5 a 50/50 mixture of buffers for pH 9 and 10 was used; for buffering at pH 10.5 a 50/50 mixture of buffers for pH 10 and 11 was used; for buffering at pH 11.5 a 50/50 mixture of buffers for pH 11 and 12 was used; for buffering at pH 12.5 a 50/50 mixture of buffers for pH 12 and 13 was used). A LOQ of ca. 8 μg/mL was determined.

The thermodynamic pH-dependent solubility of Form A2+M11 was determined as described in Example 5g for Form E except that an LOQ of 18 μg/mL was determined.

The invention claimed is:

1. A crystalline dichloride salt of the compound of formula (I)

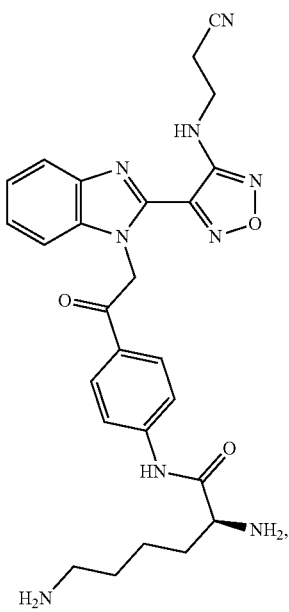

(I)

having an X-ray powder diffraction pattern comprising a peak at 6.0 degrees 2θ (±0.2 degrees 2θ) when measured using CuKα radiation.

2. The crystalline dichloride salt according to claim 1, having an X-ray powder diffraction pattern comprising peaks at 6.0, 9.4 and 9.9 degrees 2θ (±0.2 degrees 2θ) when measured using CuKα radiation.

3. The crystalline dichloride salt according to claim 1, having an X-ray powder diffraction pattern comprising peaks at 6.0, 9.4, 9.9, 10.7, 17.4, 21.4, 25.8 and 28.4, degrees 2θ (±0.2 degrees 2θ) when measured using CuKα radiation.

4. The crystalline dichloride salt according to claim 1, having an X-ray powder diffraction pattern comprising peaks at 6.0, 9.4, 9.9, 10.7, 11.6, 11.9, 17.4, 21.4, 22.4, 23.0, 24.2, 24.6, 25.8 and 28.4 degrees 2θ (±0.2 degrees 2θ) when measured using CuKα radiation.

5. The crystalline dichloride salt according to claim 1, wherein the orthorhombic primitive cell parameters are a=4.813±0.001 Å, b=20.02±0.01 Å, c=59.40±0.02 Å, V=5724±5 Å$^3$.

6. The crystalline dichloride salt according to claim 1, having an IR spectrum comprising peaks at 1701, 1665, 1335, 1241, 1170, 942, 924, 864, 699 and 628 cm$^{-1}$ (±2 cm$^{-1}$) and/or having a $^{13}$C CP MAS (14 kHz) NMR spectrum referenced to TMS and/or a 13C NMR spectrum in [D6]-DMSO comprising the peaks in the following table:

| [D$_6$]-DMSO | CP MAS 14 kHz |
|---|---|
| — | — |
| 140.9 | 137.4[a] |
| — | — |
| 141.5 | 141.4[a] |
| 119.9 | 118.8[b] |
| 123.3 | 121.8[b] |
| 124.8 | 124.2[b] |
| 111.2 | 109.5 |
| 136.1 | 134.8[a] |
| 137.7 | 137.4[a] |
| — | — |
| 155.8 | 156.2 |
| — | — |
| 40.1 | 40.3 |
| 16.7 | 19.0 |
| 119.1 | 119.6 |
| — | — |
| 51.8 | 49.1 |
| 191.3 | 196.2 |
| 129.6 | 128.1 |
| 129.6 | 131.2[c] |
| 119.0 | 121.2 |
| 143.6 | 144.0[a] |
| 119.0 | 121.2 |
| 129.6 | 128.9[c] |
| — | — |
| 168.3 | 167.1 |
| 52.7 | 55.2 |
| 30.3 | 34.6[d] |
| 21.1 | 25.0[d] |
| 26.2 | 26.6[d] |
| 38.1 | 39.5 |
| — | — |
| — | — |

[a], [b], [c], [d] Signals with the same superscript might be exchanged.

7. A process for preparing the crystalline dichloride salt of a compound of formula (I)

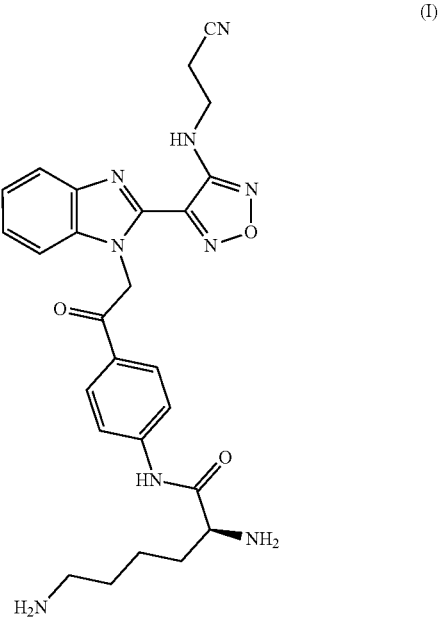 [SMILES: N#CCCNc1nonc1-c1nc2ccccc2n1CC(=O)c1ccc(NC(=O)[C@@H](N)CCCCN)cc1]

(I)

wherein the dichloride salt of the compound of formula (I) has an X-ray powder diffraction pattern comprising a peak at 6.0 degrees 2θ (±0.2 degrees 2θ) when measured using CuKα radiation, comprising the step of crystallizing the dichloride salt of the compound of formula (I) from acetonitrile, methanol, ethanol, ethylacetate, or isopropanol or mixture thereof, or a solvent mixture comprising acetonitrile, methanol, ethanol, ethylacetate and/or isopropanol.

8. The process according to claim 7, wherein the process comprises the step of crystallizing the dichloride salt of the compound of formula (I) from acetonitrile, methanol or ethanol or mixture thereof, or a solvent mixture comprising acetonitrile, methanol and/or ethanol.

9. A pharmaceutical composition comprising a pharmaceutically effective amount of a crystalline dichloride salt of the compound of formula (I)

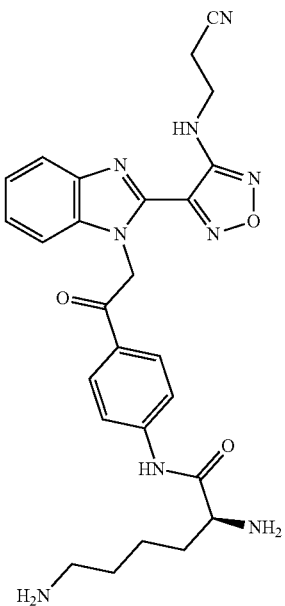

(I)

wherein the dichloride salt of the compound of formula (I) has an X-ray powder diffraction pattern comprising a peak at 6.0 degrees 2θ (±0.2 degrees 2θ) when measured using CuKα radiation, in combination with a pharmaceutically acceptable carrier, diluent or excipient.

10. A method of treating a proliferative disorder or disease comprising administering a therapeutically effective amount of a crystalline dichloride salt of the compound of formula (I)

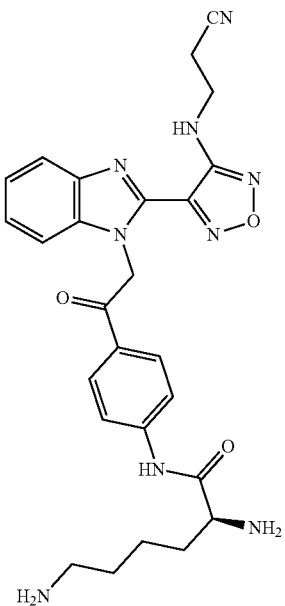

(I)

wherein the dichloride salt of the compound of formula (I) has an X-ray powder diffraction pattern comprising a peak at 6.0 degrees 2θ (±0.2 degrees 2θ) when measured using CuKα radiation, to a patient in need thereof.

11. The method of treating a proliferative disorder or disease according to claim 10, wherein the proliferative disorder or disease is a neoplastic disease selected from epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and *glomus* tumors, naevi and melanomas, soft tissue tumors and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, odontogenic tumors, gliomas, neuroepitheliomatous neoplasms, meningiomas, nerve sheath tumors, granular cell tumors and alveolar soft part sarcomas, Hodgkin's and non-Hodgkin's lymphomas, other lymphoreticular neoplasms, plasma cell tumors, mast cell tumors, immunoproliferative diseases, leukemias, miscellaneous myeloproliferative disorders, lymphoproliferative disorders and myelodysplastic syndromes.

12. The method of treating a proliferative disorder or disease according to claim 10, wherein the proliferative disorder or disease is cancer.

13. The method of treating a proliferative disorder or disease according to claim 10, wherein the proliferative disorder or disease is cancer, wherein the cancer in terms of the organs and parts of the body affected is selected from the brain, breast, cervix, ovaries, colon, rectum, lung, endocrine system, bone, adrenal gland, thymus, liver, stomach, intestine, pancreas, bone marrow, hematological malignancies, bladder, urinary tract, kidneys, skin, thyroid, brain, head, neck, prostate and testis.

14. The method of treating a proliferative disorder or disease according to claim 10, wherein the proliferative disorder or disease is cancer selected from the group consisting of brain cancer, breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas.

15. The method of treating a proliferative disorder or disease according to claim 10, wherein the proliferative disorder or disease is a neoplastic disease, which neoplastic disease is a brain neoplasm selected from glial- and non-glial-tumors, astrocytomas, oligodendrogliomas, ependydomas, menigiomas, haemangioblastomas, acoustic neuromas, craniopharyngiomas, primary central nervous system lymphoma, germ cell tumors, pituitary tumors, pineal region tumors, primitive neuroectodermal tumors (PNET's), medullablastomas, haemangiopericytomas, spinal cord tumors and genetically-driven brain neoplasms.

16. The method of treating a proliferative disorder or disease according to claim 10, wherein the proliferative disorder or disease is a neoplastic disease, which neoplastic disease is glioblastoma multiforme.

17. The method of treating a proliferative disorder or disease according to claim 12, wherein the cancer to be treated is a solid tumor.

18. The method of treating a proliferative disorder or disease according to claim 10, wherein the treatment of a proliferative disorder or disease is treatment of a proliferative disorder or disease in a human.

19. The method according to claim 13, wherein the proliferative disorder or disease is colorectal cancer, small cell lung cancer, non-small cell lung cancer, large cell lung cancer, mesothelioma, gastric cancer, lymphoma, leukemia, myeloma or lymphoid malignancies.

20. The method according to claim 15, wherein the proliferative disorder or disease is glioblastoma multiforme, unspecified gliomas, chordomas, meningiomas, neurofibromatosis, peripheral nerve sheath tumors or tuberous sclerosis.

* * * * *